US012767985B2

(12) United States Patent
Hill et al.

(10) Patent No.: US 12,767,985 B2
(45) Date of Patent: Oct. 20, 2026

(54) METHODS OF DIAGNOSING A DISEASE STATE

(71) Applicant: La Trobe University, Bundoora (AU)

(72) Inventors: Andrew Francis Hill, Greensborough (AU); Lesley Cheng Sim, Murrumbeena (AU)

(73) Assignee: La Trobe University, Bundoora (AU)

( * ) Notice: Subject to any disclaimer, the term of this patent is extended or adjusted under 35 U.S.C. 154(b) by 1001 days.

(21) Appl. No.: 17/299,615

(22) PCT Filed: Dec. 4, 2019

(86) PCT No.: PCT/AU2019/051326
§ 371 (c)(1),
(2) Date: Jun. 3, 2021

(87) PCT Pub. No.: WO2020/113271
PCT Pub. Date: Jun. 11, 2020

(65) Prior Publication Data

US 2022/0017962 A1 Jan. 20, 2022

(30) Foreign Application Priority Data

Dec. 4, 2018 (AU) ................................ 2018904605

(51) Int. Cl.
*C12Q 1/6883* (2018.01)

(52) U.S. Cl.
CPC ...... *C12Q 1/6883* (2013.01); *C12Q 2600/112* (2013.01); *C12Q 2600/118* (2013.01); *C12Q 2600/178* (2013.01)

(58) Field of Classification Search
None
See application file for complete search history.

(56) References Cited

U.S. PATENT DOCUMENTS

| | | | | |
|---|---|---|---|---|
| 2001/0051344 | A1* | 12/2001 | Shalon | B82Y 30/00 422/68.1 |
| 2015/0024961 | A1* | 1/2015 | Klass | G01N 33/57434 435/7.1 |
| 2019/0249250 | A1 | 8/2019 | Bianco et al. | |

FOREIGN PATENT DOCUMENTS

| | | | |
|---|---|---|---|
| CN | 103025890 | A | 4/2013 |
| CN | 105617382 | A | 6/2016 |
| CN | 108463561 | A | 8/2018 |
| WO | WO 2011/032155 | A2 | 3/2011 |
| WO | WO 2013/036936 | A1 | 3/2013 |
| WO | WO 2014/018650 | A1 | 1/2014 |
| WO | WO 2017/084770 | A1 | 5/2017 |
| WO | WO 2018/236590 | A1 | 12/2018 |
| WO | WO 2020/113271 | A1 | 6/2020 |

OTHER PUBLICATIONS

Lucentini (The Scientist, 2004, vol. 18, p. 20) (Year: 2004).*
International Search Report and Written Opinion, mailed Feb. 12, 2020, in connection with Application No. PCT/AU2019/051326.
International Preliminary Report on Patentability, mailed Jun. 17, 2021, in connection with Application No. PCT/AU2019/051326.
Cao et al., MicroRNA biomarkers of Parkinson's disease in serum exosome-like microvesicles. Neurosci Lett. Mar. 22, 2017;644:94-99. doi: 10.1016/j.neulet.2017.02.045. Epub Feb. 20, 2017.
Chatterjee et al., Studying the system-level involvement of microRNAs in Parkinson's disease. PLOS One. Apr. 1, 2014;9(4):e93751. doi: 10.1371/journal.pone.0093751. 15 pages.
Chen et al., Identification of aberrant circulating miRNAs in Parkinson's disease plasma samples. Brain Behav. Feb. 19, 2018;8(4):e00941. doi: 10.1002/brb3.941. 9 pages.
Cheng et al., Prognostic serum miRNA biomarkers associated with Alzheimer's disease shows concordance with neuropsychological and neuroimaging assessment. Mol Psychiatry. Oct. 2015;20(10):1188-96. doi: 10.1038/mp.2014.127. Epub Oct. 28, 2014.
Li, Profiling of Plasma/Serum Circulating MicroRNAs in Parkinson's Disease. Doctoral Dissertation. The Chinese University of Hong Kong. Mar. 2016. 166 pages.
Schwienbacher et al., Plasma and White Blood Cells Show Different miRNA Expression Profiles in Parkinson's Disease. J Mol Neurosci. Jun. 2017;62(2):244-254. doi: 10.1007/s12031-017-0926-9. Epub May 24, 2017. Accepted Manuscript.24 pages.
Xie et al., MicroRNA profiling in kidney disease: Plasma versus plasma-derived exosomes. Gene. Sep. 5, 2017;627:1-8. doi: 10.1016/j.gene.2017.06.003. Epub Jun. 3, 2017.
EP 19893378.0, Nov. 8, 2022, Extended European Search Report.
Extended European Search Report, mailed Nov. 8, 2022 for European Application No. 19893378.0.
Khoo et al., Plasma-based circulating MicroRNA biomarkers for Parkinson's disease. Parkinsons Dis. 2012;2(4):321-31. doi: 10.3233/JPD-012144.
Lugli et al., Plasma Exosomal miRNAs in Persons with and without Alzheimer Disease: Altered Expression and Prospects for Biomarkers. PLoS One. Oct. 1, 2015;10(10):e0139233. doi: 10.1371/journal.pone.0139233.

(Continued)

*Primary Examiner* — Katherine D Salmon
(74) *Attorney, Agent, or Firm* — Wolf, Greenfield & Sacks, P.C.

(57) ABSTRACT

The present invention relates to microRNA biomarkers for the diagnosis, monitoring and therapy of neurodegenerative disorders including Parkinson's Disease, Alzheimer's Disease and prion diseases.

5 Claims, 25 Drawing Sheets

Specification includes a Sequence Listing.

(56) References Cited

OTHER PUBLICATIONS

Ma et al., Serum miR-221 serves as a biomarker for Parkinson's disease. Cell Biochem Funct. Oct. 2016;34(7):511-515. doi: 10.1002/cbf.3224.

Konski, A., USPTO Update on Patent-Eligibility for Life Science Inventions. Foley & Lardner LLP. Sep. 25, 2017. Accessed Jan. 7, 2025 from <https://www.foley.com/insights/publications/2017/09/USPTO-update-on-patenteligibility-for-life- science/>. 2 pages.

No Author Listed, Total Exosome Isolation (from other body fluids). Catalog No. 4484453. Invitrogen by Life Technologies. Jun. 28, 2013. 2 pages.

* cited by examiner

METHODS OF DIAGNOSING A DISEASE STATE

RELATED APPLICATIONS

This application is a national stage filing under 35 U.S.C. § 371 of international application number PCT/AU2019/051326, filed Dec. 4, 2019, which claims the benefit of Australian application number 2018904605, filed Dec. 4, 2018, each of which is herein incorporated by reference in its entirety.

FIELD OF THE INVENTION

The field of the invention relates to biomarkers for the diagnosis, monitoring and therapy of neurodegenerative disorders including Parkinson's Disease and prion diseases.

BACKGROUND

Neurodegenerative disorders are diseases or conditions associated with the progressive loss of structure or function of the brain, including death of neurons. Many neurodegenerative diseases including Parkinson's disease (PD), frontotemporal dementia, prion's disease, Alzheimer's disease (AD), tauopathies, Amyotrophic lateral sclerosis and Huntington's disease, occur as a result of neurodegenerative processes and dementia.

The confirmation of diagnosis of neurodegenerative disorders upon dementia related symptoms such as PD and prion diseases typically involve neuropsychological and memory assessment, brain biopsy or autopsy, thereby making such confirmation, monitoring and intervention, problematic.

Prion diseases (or transmissible spongiform encephalopathies) are an invariably fatal class of progressive neurodegenerative disorders, including Creutzfeldt-Jakob disease (CJD) or sporadic Creutzfeldt-Jakob disease (sCJD) and Gerstmann-Straüssler-Scheinker (GSS) syndrome in humans, and bovine spongiform encephalopathy and scrapie in animals. Due to the prolonged asymptomatic and chronic nature of prion diseases, there is no current treatment or effective ante-mortem diagnostic method. Although the disease pathology is contributed by the conformational conversion of normal cellular $PrP^{C}$ to the disease-associated isoform $PrP^{Sc}$, the characteristic spongiform vacuolation in the brain and progressive loss of neurons have been observed prior to the manifestation of clinical symptoms of prion diseases. The gradual pathological changes are often accompanied by neuronal dysfunction (such as abnormal neuritic sprouting and synaptic deficits) prior to the onset of clinical signs in which the loss of neurons have already occurred. In humans, sporadic CJD commonly presents as a dementing encephalopathy with myoclonus, cerebellar ataxia, and (typically) a duration of illness with a median survival of four months. Clinical diagnosis of prion diseases is performed in an advanced stage of neurological decline, where affected individuals are often immobile and non-communicable. It is therefore difficult to reach a successful therapeutic intervention at this late stage because of the high PrP concentration and neuronal loss. As indicated above, confirmation of a diagnosis of prion diseases is either by undertaking a brain biopsy or autopsy. Little is known about the pathogenesis of prion diseases and the key regulators of the molecular processes during infection that drive the prion infectivity and disease spreading.

PD is the second most common form of neurodegenerative disease. It is characterized by α-synuclein aggregation (α-syn), increased reactive oxygen species (ROS) emission, and the degeneration of dopaminergic neurons in the substantia nigra (SN). Over time, neurological dysfunction leads to the loss of dopamine, which is involved in smooth muscle control, followed by the appearance of clinical symptoms. The clinical manifestation of PD include muscle rigidly, tremors, bradykinesia, postural instability, unilateral movement and persistent asymmetry. Early diagnosis of PD is the most difficult and relies on a series of neurological and physical examinations, laboratory tests and brain imaging. Progression of the disease heavily relies on the appearance of clinical symptoms and subjective clinical assessment. Improvement in early diagnosis and monitoring disease progression will assist in patient care such as prescribing, and monitoring of current therapeutic protocols used to manage symptoms.

Cognitive impairment is frequently used to assess all types of dementia and neurodegenerative diseases. Impairment in memory, thinking and/or language abilities affect the majority of patients diagnosed with AD, however cognitive impairment affects less than 30% of PD patients. Various cognitive tests are used across clinics such as the Parkinson's Disease-Cognitive Rating Scale (PD-CRS) and the SCales for Outcomes of PArkinson's disease—cognition (SCOPA-Cog), with higher scores reflecting better cognitive performance. Current cognitive tests used to assess memory and brain function can provide varying levels of sensitivity and accuracy, making these assessments highly subjective. Furthermore, diagnosis of neurodegenerative disorders, including dementia, is often based on analysis of a patient's cognitive function. Due to effective compensatory mechanisms in the brain, a decrease of cognitive function is usually only diagnosed when a disease is in its later stages and fewer treatments are available.

Some PD patients do not experience any problems with cognition, while other may have dementia-associated PD, and if they do is often in the later stages of Parkinson's disease. Clinical phenotyping is performed to assess movement function and impairment into defined categories of the Hoeyn and Yahr (HY) scale (range 1 to 5). A HY score of 1 indicates that the patient displays unilateral movement only and on the top end of the scale, a HY of 5, indicates the patient is wheelchair bound or bedridden. The mean HY score of patients clinically diagnosed with PD at the time of death was found to be an average of 4.8 and displayed severe nigral cell loss on autopsy. Further understanding of the pathological changes that proceeds nigral loss before the appearance of symptoms need to be investigated.

There is a need for less-invasive diagnostic tests, for example for improved population-based screening for dementia related conditions and patient care in order to refer patients for further examination, diagnosis and treatment to alleviate symptoms. There is a need in the field for less-invasive diagnostic tests with the ability to differentiate between neurodegenerative diseases and dementia related conditions, and/or to assist with pre-clinical monitoring of subjects, such as aging people. Furthermore, there is a need for less-invasive tests for monitoring a neurodegenerative disease state or a stage of neurodegenerative disease, for example in response to therapy.

SUMMARY OF THE INVENTION

The present inventors have demonstrated that the levels of expression of one or more small non-coding RNA associated with exosomes in a sample from a subject can be used to diagnose a neurodegenerative disease state or a stage of development of a neurodegenerative disease state, such as dementia, AD, PD and/or a prion disease.

Accordingly, in one aspect the present invention provides a method of diagnosing a disease state of a human subject, said method comprising the steps of: a) measuring the level of expression of at least one small non-coding RNA comprising a nucleotide sequence selected from the group consisting of SEQ ID NOs: 1 to 79, in a sample from the subject, wherein the sample comprises extracellular vesicles; and b) comparing the level of expression of the at least one small non-coding RNA to a reference level of expression of the at least one small non-coding RNA, wherein an increased or decreased level of expression of the at least one small non-coding RNA compared to the reference level is indicative of a disease state or a stage of development of a disease state.

In another aspect, the reference level of expression of the at least one small non-coding RNA is the level of expression of the at least one small non-coding RNA in sample from a normal subject. In another aspect, the reference level of expression of the at least one small non-coding RNA is a threshold level of expression. In one aspect, the threshold level of expression is a cut-off value.

In one aspect, the at least one small non-coding RNA is a microRNA (miRNA).

In another aspect, the extracellular vesicles in the sample are microvesicles. In another aspect, the sample comprising microvesicles is a sample enriched for microvesicles.

The present inventors have demonstrated that blood samples and brain derived tissue comprises exosomes comprising miRNA that are deregulated in disease states. Accordingly, in one aspect the sample is blood, serum or plasma. In a further aspect, the extracellular vesicles are exosomes.

The present inventors have demonstrated that the levels of expression of one or more small non-coding RNA associated with exosomes in a sample from a subject can be used to diagnose a neurodegenerative disease state or a stage of development of a number of neurodegenerative disease states, such as dementia, AD, PD and/or a prion disease.

Accordingly, in one embodiment the disease is a neurodegenerative disease. In a preferred aspect, the disease state is PD or a predisposition to PD, a prion disease or a predisposition to a prion disease, CJD or a predisposition to CJD, AD or a predisposition to AD, or dementia or a predisposition to dementia.

In one embodiment, the present invention provides a method wherein an increased or decreased level of expression of at least one small non-coding RNA selected from the group consisting of SEQ ID NOs: 1 to 28 compared to the reference level(s) is indicative of PD or a predisposition to PD. In one embodiment, the present invention provides a method wherein an increased or decreased level of expression of at least three small non-coding RNA selected from the group consisting of SEQ ID NOs: 1 to 28 compared to the reference levels is indicative of Parkinson's disease or a predisposition to Parkinson's disease. In one embodiment, the present invention provides a method wherein an increased or decreased level of expression of at least three small non-coding RNA selected from the group consisting of SEQ ID NOs: 1, 5, 7 and 22, and at least five small non-coding RNA selected from the group consisting of SEQ ID NOs: 2 to 4, 6, 8 to 21 and 23 to 28, compared to the reference levels is indicative of Parkinson's disease or a predisposition to Parkinson's disease. In one embodiment, the present invention provides a method wherein an increased or decreased level of expression of SEQ ID NO: 22, and at least three small non-coding RNA selected from the group consisting of SEQ ID NOs: 7, 10, 23 and 3, and at least five small non-coding RNA selected from the group consisting of SEQ ID NOs: 61 and 71-79, compared to the reference levels is indicative of Parkinson's disease or a predisposition to Parkinson's disease.

In one embodiment, the present invention provides a method wherein an increased or decreased level of expression of at least one small non-coding RNA selected from the group consisting of SEQ ID NOs: 54 through 70, compared to the reference level(s) is indicative of CJD or a predisposition to CJD. In one embodiment, the present invention provides a method wherein an increased or decreased level of expression of at least three small non-coding RNA selected from the group consisting of SEQ ID NOs: 54 through 70 compared to the reference levels is indicative of CJD or a predisposition to CJD. In one embodiment, the present invention provides a method wherein an increased or decreased level of expression of at least three small non-coding RNA selected from the group consisting of SEQ ID NOs: 1, 5, 7 and 22, and at least five small non-coding RNA selected from the group consisting of SEQ ID NOs: 54, 56 to 58, 60 to 64, and 67 to 70, compared to the reference levels is indicative of CJD or a predisposition to CJD. In one embodiment, the present invention provides a method wherein an increased or decreased level of expression of SEQ ID NO: 22, and at least three small non-coding RNA selected from the group consisting of SEQ ID NOs: 56, 58, 60, 62 and 70, and at least five small non-coding RNA selected from the group consisting of SEQ ID NOs: 61 and 71 to 79, compared to the reference levels is indicative of CJD or a predisposition to CJD.

In another embodiment, the present invention provides a method further comprising a psychological, behavioural, physiological and/or genetic assessment of the subject. In another embodiment, the psychological assessment determines the presence and/or level of cognitive impairment.

In another embodiment, the present invention provides a method further comprising selecting a treatment or modifying a treatment for the disease state or the predisposition to the disease state, based on the diagnosis of disease state.

In another embodiment, the present invention provides a method further comprising administering to the subject a therapeutically effective amount of an anti-disease state therapy.

In another embodiment, the present invention provides a method wherein the disease state is Alzheimer's Disease or a predisposition to Alzheimer's Disease.

In another embodiment, the present invention provides a method wherein an increased or decreased level of expression of at least one small non-coding RNA selected from the group consisting of SEQ ID NO: 22, SEQ ID NO: 79, SEQ ID NO: 71, SEQ ID NO: 72, ID NO: 73, SEQ ID NO: 74, SEQ ID NO: 75, SEQ ID NO: 61, SEQ ID NO: 76, SEQ ID NO: 77, and SEQ ID NO: 79, compared to the reference level(s) is indicative of Alzheimer's Disease or a predisposition to Alzheimer's Disease.

In another embodiment, the present invention provides a method wherein an increased or decreased level of expression of at least five small non-coding RNA selected from the group consisting of SEQ ID NO: 22, SEQ ID NO: 79, SEQ ID NO: 71, SEQ ID NO: 72, ID NO: 73, SEQ ID NO: 74, SEQ ID NO: 75, SEQ ID NO: 61, SEQ ID NO: 76, SEQ ID NO: 77, and SEQ ID NO: 79, compared to the reference level(s) is indicative of Alzheimer's Disease or a predisposition to Alzheimer's Disease.

DETAILED DESCRIPTION

Figure 1:
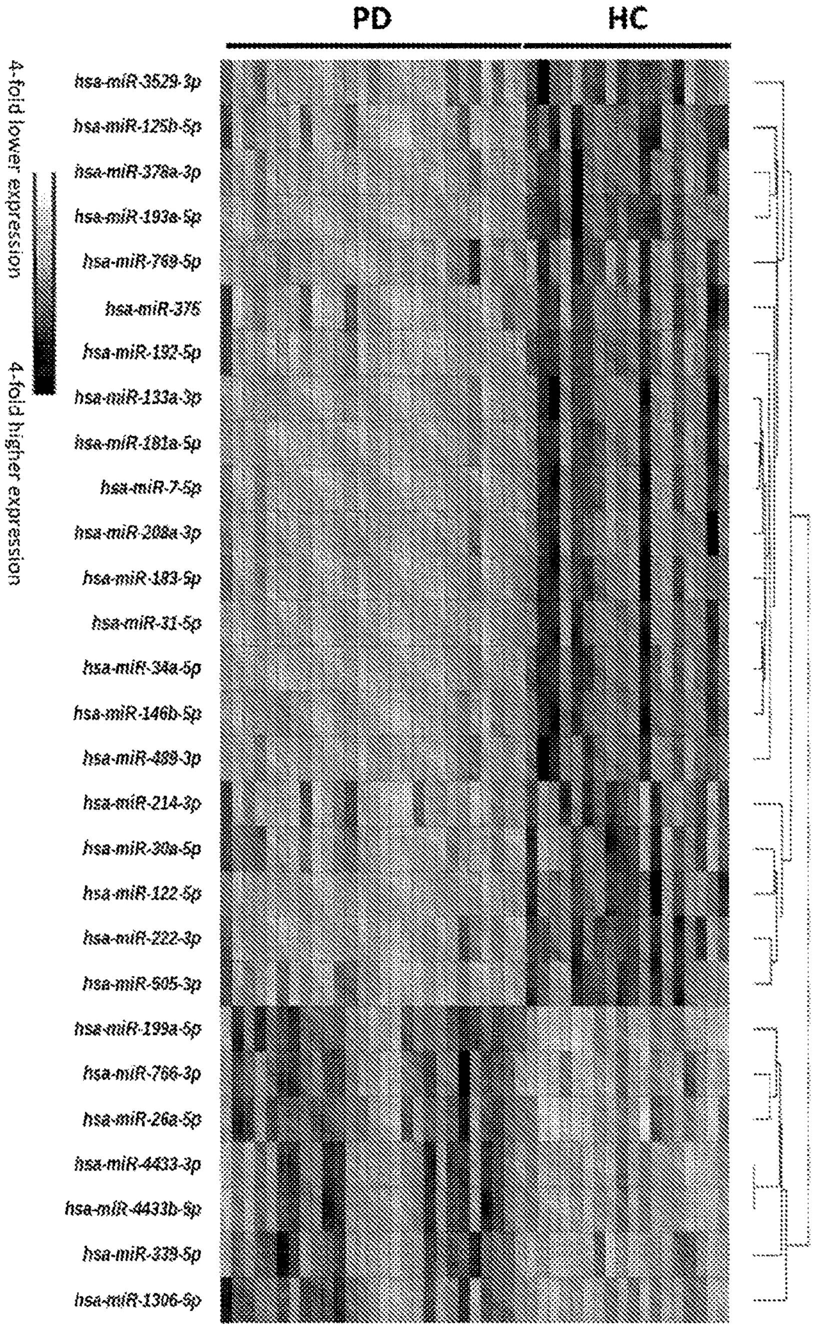
FIG. 1: Hierarchical clustering of differentially expressed serum exosomal miRNA biomarkers obtained from serum of healthy controls and participants with Parkinson's disease Using the small RNA deep sequencing data obtained from the discovery set, hierarchical clustering was performed using Partek Genomics Suite on significantly differentially expressed miRNA using Euclidean average linkage by miRNA. 28 miRNA were found to be significantly deregulated (FDR (PD Vs HC)≤0.05 and ±2 fold change); There are three major nodes of the dendrogram. Node 1 contains 16 miRNA and node 2 which contains 5 miRNAs which are both found to be up-regulated. Node 3 contains 7 miRNA which were found to be down-regulated. The darker the shade of grey, the higher the expression of miRNA compared to HC. Patient samples were arranged by attribute. HC, n=18 and PD, n=27.

The present inventors have demonstrated that the levels of expression of one or more small non-coding RNA associated with exosomes in a sample from a subject can be used to diagnose a neurodegenerative disease state or a stage of development of a neurodegenerative disease state, such as dementia, AD, PD or a prion disease.

For example, the present inventors have established neurodegenerative disease-specific exosomal miRNA signatures associated with dementia, AD, PD and CJD that are present in the blood of diseased subjects. As it is not possible to isolate brain material from live patients, the detection of such miRNA signatures in blood (e.g. serum) is intended to provide, in one aspect, a less-invasive method of diagnosing neurodegenerative disease(s).

Accordingly, in one aspect the present invention provides a method of diagnosing a disease state of a human subject, said method comprising the steps of: a) measuring the level of expression of at least one small non-coding RNA comprising a nucleotide sequence selected from the group consisting of SEQ ID NOs:1 to 79, in a sample from the subject, wherein the sample comprises extracellular vesicles; and b) comparing the level of expression of the at least one small non-coding RNA to a reference level of expression of the at least one small non-coding RNA, wherein an increased or decreased level of expression of the at least one small non-coding RNA compared to the reference level is indicative of a disease state or a stage of development of a disease state.

Any combination of one or more of the small non coding RNA (e.g. miRNA) described herein can be used in any of the methods described herein, e.g., used in methods for diagnosing a neurodegenerative disorder in a subject, identifying a subject at risk (e.g., increased or decreased risk) of developing a neurodegenerative disorder, predicting the rate of disease progression in a subject having a neurodegenerative disorder, selecting a subject for treatment of a neurodegenerative disorder, or determining the efficacy of treatment in a subject having a neurodegenerative disorder. Importantly, the present inventors have associated particular small non-coding RNAs (e.g. miRNAs) with particular neurodegenerative disorders. Accordingly, specific small non coding RNAs (e.g. miRNAs) can be used in methods for diagnosing a particular neurodegenerative disorder in a subject, identifying a subject at risk (e.g., increased or decreased risk) of developing a particular neurodegenerative disorder, predicting the rate of disease progression in a subject having a particular neurodegenerative disorder, selecting a subject for treatment of a particular neurodegenerative disorder, or determining the efficacy of treatment in a subject having a particular neurodegenerative disorder.

Neurodegenerative disorders are a class of neurological diseases that are characterized by the progressive loss of the structure and function of neurons and neuronal cell death. Inflammation has been implicated for a role in several neurodegenerative disorders. Progressive loss of motor and sensory neurons and the ability of the mind to refer sensory information to an external object is affected in different kinds of neurodegenerative disorders. Non-limiting examples of neurodegenerative disorders include dementia, Parkinson's disease, Alzheimer's disease, Huntington's disease, amyotrophic lateral sclerosis (ALS, e.g., familial ALS and sporadic ALS), prion diseases such as CJD and multiple sclerosis (MS).

As used herein the term "Parkinson's Disease" or "PD" refers to a progressive disorder of the central nervous system (CNS), which is caused by the degeneration of dopaminergic neurons in the substantia nigra of the midbrain. These neurons normally project to the striatum, consisting of the caudate and putamen nuclei, whose neurons bear dopamine receptors. This projection of neurons is just one component of the complex network of interconnections among the deep gray-matter structures known as the basal ganglia. Neurochemical or structural pathologic conditions affecting the basal ganglia result in diseases of motor control, classified as movement disorders.

As used herein the term "prion" refers to an infectious particle known to cause a "prion disease" (a spongiform encephalopathy) in humans and animals. The term "prion" is a contraction of the words "protein" and "infection" and the particles are comprised largely if not exclusively of $PrP^{Sc}$ molecules encoded by a PrP gene. Prions are distinct from bacteria, viruses and viroids. Known prions include those which infect animals to cause scrapie, a transmissible, degenerative disease of the nervous system of sheep and goats as well as bovine spongiform encephalopathies (BSE) or mad cow disease and feline spongiform encephalopathies of cats. Four prion diseases known to affect humans are (1) Kuru, (2) Creutzfeldt-Jakob Disease (CJD), (3) Gerstmann-Strassler-Scheinker Disease (GSS), and (4) Fatal Familial Insomnia (FFI). As used herein prion includes all forms of prions causing all or any of these diseases or others in any animals used—and in particular in humans and in domesticated farm animals.

As used herein the term "Alzheimer's disease" includes patients diagnosed with Alzheimer's disease (AD) based on the establish criteria from the National Institute of Neurological and Communicative Diseases and Stroke-Alzheimer's Disease and Related Disorders Association (NINCDA-ADRDA), and subjects with "presymptomatic AD". "Presymptomatic AD". includes a subject having no to mild cognitive impairment but having a risk factor for development of AD such as one or more ApoEε4 alleles and/or a high amyloid burden. This may also be determined by PET imaging. A "stage of AD" means from presymptomatic to early onset to from mild to severe forms of AD. It also encompasses individuals with a likelihood of developing AD. A subject being tested may undergo additional testing after being stratified as having or being at risk of developing AD. The additional testing includes a range of behavioural or psychological evaluations such as level of cognitive ability as well as genetic testing for missense mutations in the chromosome 21 gene coding for β-amyloid precursor protein, a chromosome 14q gene coding for a 467 amino acid protein with 7 putative membrane-spanning domains and inheritance of the APoEε4 allele of the gene encoding apolipoprotein E. The presence of one or 2 alleles of APoEε4 together with the miRNA signature of the present invention enables the clinician to diagnose for the presence or absence of AD or to assess the likelihood of development of AD or to assess the stage of AD. Physiological testing such as PET imaging may also be conducted.

As used herein the terms "diagnosing" and "diagnosis" refer to the identification of a disease (i.e., dementia, AD, PD or a prion disease) state at any stage of its development, and also includes the determination of predisposition of a subject to develop the disease. In a preferred embodiment of the invention, diagnosis of dementia, AD, PD or a prion disease in a subject occurs prior to the manifestation of symptoms. Subjects with a higher risk of developing the disease are of particular concern. The diagnostic methods of the invention also allows confirmation of dementia, AD, PD or a prion disease in a subject suspected of having dementia, AD, PD or a prion disease.

For example, a "diagnosis" of PD may include the early detection of the disease or a confirmation of the diagnosis of the disease from other signs and/or symptoms (e.g., based in whole or in part on expression or expression pattern of one or more non-coding RNA biomarkers). A "diagnosis" of PD may include an assessment of the degree of disease severity (e.g., "low" to "high"; "low- to "high-dependency"), current state of disease progression (e.g., "early", "middle," or "late" stages of PD), or include a comparative assessment to an earlier diagnosis (e.g., the PDs symptoms are advancing, stable, or in remission). Similarly, a "diagnosis" of a prion disease may include the early detection of the disease or a confirmation of the diagnosis of the disease from other signs and/or symptoms (e.g., based in whole or in part on expression or expression pattern of one or more non-coding RNA biomarkers). A "diagnosis" of a prion disease may include an assessment of the degree of disease severity (e.g., "low" to "high"; "low- to "high-dependency"), current state of disease progression (e.g., "early", "middle," or "late" stages of a prion disease), or include a comparative assessment to an earlier diagnosis (e.g., the prion disease's symptoms are advancing, stable, or in remission). Similarly, a "diagnosis" of AD may include the early detection of the disease or a confirmation of the diagnosis of the disease from other signs and/or symptoms (e.g., based in whole or in part on expression or expression pattern of one or more non-coding RNA biomarkers). A "diagnosis" of AD may include an assessment of the degree of disease severity (e.g., "low" to "high"; "low- to "high-dependency"), current state of disease progression (e.g., "early", "middle," or "late" stages of AD), or include a comparative assessment to an earlier diagnosis (e.g., AD symptoms are advancing, stable, or in remission). Similarly, a "diagnosis" of dementia may include the early detection of the disease or a confirmation of the diagnosis of the disease from other signs and/or symptoms (e.g., based in whole or in part on expression or expression pattern of one or more non-coding RNA biomarkers). A "diagnosis" of dementia may include an assessment of the degree of disease severity (e.g., "low" to "high"; "low- to "high-dependency"), current state of disease progression (e.g., "early", "middle," or "late" stages of dementia), or include a comparative assessment to an earlier diagnosis (e.g., dementia symptoms are advancing, stable, or in remission).

A diagnosis may include a "prognosis," that is, a future prediction of the progression of dementia, AD, PD or of a prion disease, based on the observed disease state (e.g., based in whole or in part on expression or expression pattern of one or more non-coding RNA biomarkers). A diagnosis or prognosis may be based on one or more samplings of non-coding RNA from a biological sample obtained from a subject, and may involve a prediction of disease response to a particular treatment or combination of treatments for dementia, AD, PD or a prion disease. An "increased risk" of developing dementia, AD, PD or a prion disease may be diagnosed by the presence of expression patterns characteristic of one or more miRNA biomarkers for early or late stage dementia, AD, PD or a prion disease in otherwise asymptomatic subjects.

As used herein the term "disease state" refers to the presence or absence of a symptom associated with dementia, AD, PD or a prion disease at any stage of its development, and also includes the determination of predisposition of a subject to develop the disease.

Most symptoms of PD are caused by an absence or suboptimal levels of dopamine in the brain, in some instance caused by a degeneration of dopaminergic neurons over time. PD is characterized by α-synuclein aggregation (α-syn), increased reactive oxygen species (ROS) emission, and the degeneration of dopaminergic neurons in the substantia nigra (SN). Over time, neurological dysfunction leads to the loss of dopamine, which is involved in smooth muscle control, followed by the appearance of clinical symptoms. The clinical manifestation of PD include muscle rigidly, tremors, bradykinesia, postural instability, unilateral movement and persistent asymmetry.

Symptoms of prion diseases include, behaviour problems, communication problems, memory/cognitive defects, movement problems, swallowing problems, visual/perceptive problems and seizures. In humans, sporadic CJD commonly presents as a dementing encephalopathy with myoclonus, and cerebellar ataxia.

As used herein the term "disease stage" refers to a stage of development of dementia, AD, PD or a prion disease including asymptomatic or pre-symptomatic PD or a prion disease, and/or a risk of developing dementia, AD, PD or a prion disease.

The ability to identify disease states and disease stages including asymptomatic or pre-symptomatic or early onset subjects enables early clinical, therapeutic and behavioural intervention leading to significant improvement in quality of life for the subject and surrounding social and family networks.

As used herein the term "subject" is intended to include all eukaryotic organisms shown to or expected to have nucleic acid-containing particles. In particular embodiments, the subject is a mammal, a human or nonhuman primate, a dog, a cat, a horse, a cow, other farm animals, or a rodent (e.g. mice, rats, guinea pig. etc.). A human subject may be a normal human being without any observable symptoms of a disease, such as dementia, AD, PD or a prion disease. A human subject may be a human being with observable symptoms of a disease, such as dementia, AD, PD or a prion disease. The observable symptoms may be observed by the human being himself, or by a medical professional. The term "subject," "patient," and "individual" are used interchangeably herein.

Preferably the subject is a human subject.

As used herein, the term "sample" refers to a sample that contains biological materials such as nucleic acids and protein. In some embodiments, the biological sample may suitably comprise a bodily fluid from a subject. The bodily fluids can be fluids isolated from anywhere in the body of the subject, for example, a peripheral location, including but not limited to, for example, blood, plasma, serum, urine, sputum, spinal fluid, cerebrospinal fluid (CSF), pleural fluid, nipple aspirates, lymph fluid, fluid of the respiratory, intestinal, and genitourinary tracts, tear fluid, saliva, breast milk, fluid from the lymphatic system, semen, intra-organ system fluid, ascitic fluid, tumor cyst fluid, amniotic fluid and cell culture supernatant, and combinations thereof. In some embodiments, the body fluid is plasma or serum. Suitably, a sample volume of about 0.1 ml to about 100 mL fluid may be used. The volume of fluid may depend on a few factors, e.g., the type of fluid used. In another embodiment the tissue is brain tissue.

In one embodiment, the sample is blood, serum or plasma.

As used herein the term "extracellular vesicles" refers to membranous microvesicles that may be shed by eukaryotic cells, or budded off of the plasma membrane, to the exterior of the cell. These membrane vesicles are heterogeneous in size with diameters ranging from about 10 nm to about 5000 nm. These microvesicles include microvesicles, microvesicle-like particles, prostasomes, dexosomes, texosomes, ectosomes, oncosomes, apoptotic bodies, retrovirus-like particles, and human endogenous retrovirus (HERV) particles and any other terms that refer to such extracellular structures. For example, exosomes can be purified from, or an enriched population of exosomes can be prepared from serum (e.g. "serum exosomes") or from brain tissue (e.g. brain derived exosomes; "BDE").

Small microvesicles (approximately 10 to 5000 nm, and more often 30 to 200 nm in diameter) that are released by exocytosis of vesicles are referred to as "microvesicles" or "exosomes".

In one embodiment, the extracellular vesicles are exosomes.

In one embodiment, the sample comprising microvesicles is a sample enriched for microvesicles.

A sample may be enriched for microvesicles using standard methods; a microvesicle such as an exosome may be purified or concentrated prior to analysis.

An enriched population of exosomes can be obtained from a biological sample. For example, exosomes may be concentrated or isolated from a biological sample using size exclusion chromatography, density gradient centrifugation, differential centrifugation, nanomembrane ultrafiltration, immunoabsorbent capture, affinity purification, microfluidic separation, or combinations thereof.

Methods for isolating or enriching exosomes can be performed with microfluidic devices, including optionally examining miRNA expression in the isolated exosomes. Microfluidic devices, which may also be referred to as "lab-on-a-chip" systems, biomedical micro-electro-mechanical systems (bioMEMs), or multicomponent integrated systems, can be used for isolating, and analyzing, exosomes. Such systems miniaturize and compartmentalize processes that allow for isolation (e.g. binding) of exosomes, detection of exosomal biomarkers (e.g. miRNA), and/or other processes.

A microfluidic device can also be used for isolation of an exosome through size differential or affinity selection. For example, a microfluidic device can use one more channels for isolating an exosome from a biological sample based on size, or by using one or more binding agents for isolating an exosome, from a biological sample. A biological sample such as serum can be introduced into one or more microfluidic channels, which selectively allows the passage of exosomes. The selection can be based on a property of the exosomes, for example, size, shape, deformability, biomarker profile, or bio-signature.

Alternatively, a heterogeneous population of exosomes can be introduced into a microfluidic device, and one or more different homogeneous populations of exosomes can be obtained. For example, different channels can have different size selections or binding agents to select for different exosome populations. Thus, a microfluidic device can isolate a plurality of exosomes, wherein at least a subset of the plurality of exosomes comprises a different bio-signature from another subset of said plurality of exosomes.

In some embodiments, the microfluidic device can comprise one or more channels that permit further enrichment or selection of exosomes. A population of exosomes that has been enriched after passage through a first channel can be introduced into a second channel, which allows the passage of the desired exosome population to be further enriched, such as through binding agents present in the second channel.

Array-based assays and bead-based assays can be used with microfluidic device. For example, the binding agent can be coupled to beads and the binding reaction between the beads and exosomes can be performed in a microfluidic device. Multiplexing can also be performed using a microfluidic device. Different compartments can comprise different binding agents for different populations of exosomes, where each population is of a different cell-of-origin specific exosome population or each population has a different bio-signature. The hybridization reaction between the microspheres and exosomes can be performed in a microfluidic device and the reaction mixture can be delivered to a detection device. The detection device, such as a dual or multiple laser detection system can be part of the microfluidic system and can use a laser to identify each bead or microsphere by its color-coding, and another laser can detect the hybridization signal associated with each bead.

Isolation or enrichment of exosomes from biological samples can also be enhanced by use of sonication (for example, by applying ultrasound), or the use of detergents, other membrane-active agents, or any combination thereof. For example, ultrasonic energy can be applied to a sample or tissue, and without being bound by theory, release of exosomes from the sample or tissue can be increased, allowing an enriched population of exosomes that can be analyzed or assessed from a biological sample using one or more methods disclosed herein or known in the field.

Cell free nucleic acids such as small non-coding RNA (such as microRNAs) are contained in exosomes and other extracellular vesicles.

In one embodiment, the at least one small non-coding RNA is a microRNA (miRNA).

MicroRNAs (miRNAs) are small (18 to 24 nucleotide), highly conserved, genome-encoded single-stranded RNA molecules that bind to target sequences on messenger RNAs (mRNAs), and can act as post-transcriptional regulators of gene expression. miRNAs are derived from primary miRNA transcripts through processing by the Drosha ribonuclease and the Dicer enzyme. Binding between miRNA and mRNA can repress translation and/or effect decreased mRNA stability in vivo, often by triggering the destruction of the mRNA by endogenous ribonucleases. Regulation of gene expression by miRNA has been found to be important in the normal development and function of most eukaryotic organisms.

As used herein the term "microRNA" (miRNA) includes primary miRNA transcripts (pri-miRNA) or other mRNA transcripts that code for mature miRNA (e.g., miRNA processed from introns excised from mRNA transcripts), precursor miRNAs (pre-miRNA), mature single stranded miRNAs, and variants thereof, which may be naturally occurring. The term "miRNA" includes human and miRNA from other eukaryotic organisms. In some instances, the term "miRNA" also includes primary miRNA transcripts and duplex miRNAs. The name of a specific miRNA typically refers to the mature miRNA of a precursor miRNA. Some single primary miRNA transcripts may contain more than one precursor/mature miRNA. Some mature miRNA may be derived from more than one precursor miRNA. miRNA nomenclature is discussed below.

In most eukaryotes, primary miRNA is transcribed from DNA, and is processed by cellular machinery to form precursor miRNA, which is further processed to form one or more miRNA. In some eukaryotes and for some miRNA, precursor miRNA is transcribed directly from DNA, and is further processed to form miRNA (e.g., processed from introns excised from mRNA transcripts). Unless otherwise noted, the name of a specific miRNA refers to a mature miRNA sequence. Under current nomenclature rules, human miRNA are preceded with the prefix "hsa-" (i.e., an abbreviation for *Homo sapiens*) and mice miRNA are preceded with the prefix "mmu-" (i.e., an abbreviation for *Mus musculus*). Throughout the specification and figures the hsa- and the mmu-prefixes may be dropped for purposes of abbreviation.

Each miRNA may be, for example, a single strand (monomer) or a double strand (dimer).

Following the isolation of microvesicles from a biological sample, nucleic acid may be extracted from the isolated or enriched microvesicle fraction. To achieve this, in some embodiments, the microvesicles may first be lysed. The lysis of microvesicles and extraction of nucleic acids may be achieved with various methods known in the art. Such methods may also utilize a nucleic acid-binding column to capture the nucleic acids contained within the microvesicles. Once bound, the nucleic acids can then be eluted using a buffer or solution suitable to disrupt the interaction between the nucleic acids and the binding column, thereby successfully eluting the nucleic acids.

In some embodiments, the nucleic acid extraction methods also include the step of removing or mitigating adverse factors that prevent high quality nucleic acid extraction from a biological sample. Such adverse factors are heterogeneous in that different biological samples may contain various species of adverse factors. In some biological samples, factors such as excessive DNA may affect the quality of nucleic acid extractions from such samples. In other samples, factors such as excessive endogenous RNase may affect the quality of nucleic acid extractions from such samples. Many agents and methods may be used to remove these adverse factors. These methods and agents are referred to collectively herein as an "extraction enhancement operations." In some instances, the extraction enhancement operation may involve the addition of nucleic acid extraction enhancement agents to the biological sample. To remove adverse factors such as endogenous RNases, such extraction enhancement agents as defined herein may include, but are not limited to, an RNase inhibitor such as Superase-In (commercially available from Ambion Inc.) or RNaseINplus (commercially available from Promega Corp.), or other agents that function in a similar fashion; a protease (which may function as an RNase inhibitor); DNase; a reducing agent; a decoy substrate such as a synthetic RNA and/or carrier RNA; a soluble receptor that can bind RNase; a small interfering RNA (siRNA); an RNA binding molecule, such as an anti-RNA antibody, a basic protein or a chaperone protein; an RNase denaturing substance, such as a high osmolarity solution, a detergent, or a combination thereof.

For example, the extraction enhancement operation may include the addition of an RNase inhibitor to the biological sample, and/or to the isolated microvesicle fraction, prior to extracting nucleic acid.

Such enhancement agents may exert their functions in various ways, e.g., through inhibiting RNase activity (e.g., RNase inhibitors), through a ubiquitous degradation of proteins (e.g., proteases), or through a chaperone protein (e.g., a RNA-binding protein) that binds and protects RNAs. In all instances, such extraction enhancement agents remove or at least mitigate some or all of the adverse factors in the biological sample or associated with the isolated particles that would otherwise prevent or interfere with the high quality extraction of nucleic acids from the isolated particles.

As used herein the term "measuring" refers to detecting the level of expression of a small non-coding RNA (e.g. miRNA).

The analysis of nucleic acids present in the microvesicles is quantitative and/or qualitative. For quantitative analysis, the amounts (expression levels), either relative or absolute, of specific nucleic acids of interest within the microvesicles are measured with methods known in the art. For qualitative analysis, the species of specific small non-coding RNA of interest within the isolated microvesicles, whether wild type or variants, are identified with methods known in the art.

Small non-coding RNA (e.g. miRNA) may be detected by expression screening technologies such as miRNA microarrays that may contain large numbers or a "library" of miRNA sequences. Typically, miRNAs obtained from biological samples from a population of healthy subjects and a population of individuals with a disease of interest may be run on a microarray, and the differential expression of some or all of the members of the miRNA library in each sample is assessed. Other screening/high-throughput technologies that may be used to quantify and differentiate miRNA expression include massively parallel Next Generation Sequencing (NGS) technologies, or qRT-PCR. High-throughput NGS technologies, for instance, can be used to assay entire sets of RNA transcripts within samples, and can be used to compare RNA transcription profiles between samples. Microarrays and other screening technologies such as NGS may measure the presence/absence of a miRNA in a sample; sequence changes in a particular miRNA; the number of miRNA expressed below and/or above a certain concentration threshold in a sample; or an assessment of the relative or absolute amount of a particular miRNA in a sample. Typically, microarrays and other expression screening technologies such as NGS generate large amounts of data and finding miRNA expression differences between healthy and diseased populations usually requires statistical analysis. Single mRNA biomarker candidates may be found using Significance Analysis of Microarrays (SAM) protocol, or other protocols known in the art.

Small non-coding RNA can be is reverse-transcribed into complementary DNA (cDNA) before any amplification. Such reverse transcription may be performed alone or in combination with an amplification step.

Various techniques can be used to analyse an amplification product in order to determine relative miRNA expression levels.

One example of a method combining reverse transcription and amplification steps is reverse transcription polymerase chain reaction (RT-PCR), which may be further modified to be quantitative, e.g., quantitative RT-PCR. Another example of the method comprises two separate steps: a first of reverse transcription to convert RNA into cDNA and a second step of quantifying the amount of cDNA using quantitative PCR. Quantitative PCR (qPCR) analysis determines a Ct (cycle threshold) value for each reaction. In qPCR, a positive reaction is detected by, for example, accumulation of a fluorescence signal. The Ct value is defined as the number of qPCR cycles required for the fluorescent signal to cross the threshold (i.e., exceeds background level). Ct levels are inversely proportional to the amount of target nucleic acid, or control nucleic acid, in the sample (i.e., the lower the Ct level, the greater the amount of control nucleic acid in the sample).

As used herein, Ct includes "Cp"/"crossing point" which refers to the point at which the amplification curve crosses the vertical threshold line/noise band), therefore both Ct and Cp can be used interchangeably. The methods of deriving Ct or Cp include: 1) the conventional method using the cycle value at which the (baseline-corrected) amplification curve crosses some arbitrary threshold value; 2) the second derivative maximum (SDM) method, where there's no need to define an arbitrary threshold value; and 3) "fit points" method through a linear regression fit through the points of the log-linear phase of the amplification curve. In another embodiment, the copy number of the control nucleic acid can be measured using any of a variety of art-recognized techniques, including, but not limited to, qPCR or any other PCR or PCR-free methods. Copy number of the control nucleic acid can be determined using known methods known, such as by generating and utilizing a calibration, or standard curve.

As used herein the terms "level of expression", refers to the amount of expression or concentration of a small non-coding RNA (e.g. a miRNA) in a sample from a subject.

The terms "reduced levels" or "elevated levels" refer to the amount of expression or concentration of a small non-coding RNA (e.g. a miRNA) in a sample compared to a reference level of expression. For example, in the case of PD, for certain miRNAs, elevated levels in a sample indicates the presence of or a risk for PD; at the same time, other miRNAs may be present in reduced levels in patients or subjects with PD. In either of these example situations, miRNAs are "differentially expressed" in PD subjects and healthy controls.

The term "deregulation" as used herein includes up-regulation and down-regulation. Hence, in one embodiment, the at least one small non-coding RNA (e.g. miRNA) can be categorised into one two groups based on up or down-regulation for each disease state or stage of disease. As indicated above, in one embodiment, deregulation is a greater than 1.5 or −1.5 fold change in expression level.

The term "upregulation" or "increase" as used herein refers to an observable, detectable, or significant increase in a level as compared to a reference level or a level measured at an earlier or later time point in the same subject. For example, an upregulated miRNA has a greater than 1.5 fold increase in expression level.

The term "downregulation" or "decrease" as used herein refers to an observable, detectable, or significant decrease in a level as compared to a reference level or a level measured at an earlier or later time point in the same subject. For example, a downregulated miRNA has a greater than 1.5 fold decrease in expression level.

In one embodiment, significant deregulation is a greater than 1.5 or −1.5 fold change in expression level with a P value of less than or equal to 0.05. A significantly down-regulated miRNA has a greater than 1.5 fold decrease in expression level with a P value of less than or equal to 0.05. A significantly upregulated miRNA has a greater than 1.5 fold increase in expression level with a P value of less than or equal to 0.05.

In one embodiment, the reference level of expression may be the amount of expression or concentration of a small non-coding RNA in a sample from individual(s) that do not have dementia, AD, PD or a prion disease, have dementia, AD, PD or a prion disease (or a particular severity or stage of dementia, AD, PD or a prion disease), or have other reference diseases. For example, a miRNA that has reduced levels in a biological sample from PD patients is present at lower concentration in biological sample from PD patients than in serum from a subject who does not have PD.

As used herein, a "healthy control" or "HC" is a normal subject not suffering from clinically diagnosed dementia, AD, PD or a prion disease, and/or a subject without a predisposition to dementia, AD, PD or a prion disease.

In one embodiment, the reference level of expression may be a threshold level of expression.

The present inventors have demonstrated that data (e.g. preclinical data) can be used to define a threshold level of expression for subjects who are healthy or have a disease state, or a specific stage of disease.

For example, the data of the Examples includes correlation of expression levels of miRNAs with subjects of known status with respect to dementia, AD, PD or a prion disease.

The reference level, for example, may be miRNA expression levels in healthy individuals (healthy or normal controls). Alternatively, the reference level may comprise levels of expression of the miRNAs in subjects with a disease state or a specific stage of disease. Hence, elevation or reduction in expression is dependent on the type of control.

In one embodiment, the level of expression in the reference level is based on levels in healthy individuals. In this aspect, the expression of one or more miRNAs comprising nucleotide sequences as described herein is elevated relative to the healthy control and the expression of one or more miRNAs comprising nucleotide sequences described herein reduced relative to a healthy control in a subject stratified as having PD, a stage of PD or is at risk of developing PD, or has a prion disease, a stage of a prion disease or is at risk of developing a prion disease, or has a dementia, a stage of dementia or is at risk of developing dementia, or has AD, a stage of AD or is at risk of developing AD.

In another embodiment, a reference level of expression of a miRNA in subjects with known status with respect to dementia, AD, PD or a prion disease. The reference level is determined from empirically following a trial of subjects. When the level of expression of one or more miRNAs is determined in a subject with unknown status, a comparison between with the reference level allows determination of an index of probability that a subject has PD, a stage of PD or is at risk of developing PD, or has a prion disease, a stage of a prion disease or is at risk of developing a prion disease or has a dementia, a stage of dementia or is at risk of developing dementia, or has AD, a stage of AD or is at risk of developing AD. The reference level may be determined using any suitable method, such as the analysis of test results relative to a standard result which reflects individual or collective results obtained from individuals with known disease status.

A reference level may be set using data from healthy controls or from patients with a disease, or a specific stage of development of disease.

A reference level may be determined from the subjects of a specific cohort and hence there may be different controls to test samples derived from different cohorts. Accordingly, there may be determined a number of control values or ranges which correspond to cohorts which differ in respect of characteristics such as age, gender, ethnicity or health status.

A "reference level" may be a discrete level or a range of levels. The values can be a quantitative, such as a numerical value. In other embodiments, the value is qualitative, such as no exosomal miRNA, low level of exosomal miRNA, medium level of exosomal miRNA, or high level of exosomal miRNA, or variations thereof.

The reference value can be particular to physical or temporal endpoint.

A reference value may be based on samples assessed from the same subject so to provide individualized tracking/monitoring.

Reference values can be established for unaffected individuals (of varying ages, ethnic backgrounds and sexes) without a particular phenotype by determining the amount of exosomal miRNA in an unaffected individual.

Alternatively, reference values or levels can be established for individuals with a particular phenotype by determining the amount of one or more populations of exosomal miRNA in an individual with the phenotype. In addition, an index of values can be generated for a particular phenotype. For example, different disease stages can have different values, such as obtained from individuals with the different disease stages. A subject's value can be compared to the index and a diagnosis or prognosis of the disease can be determined, such as the disease stage or progression. In other embodiments, an index of values is generated for therapeutic efficacies. For example, the level of exosomal miRNA of individuals with a particular disease can be generated and noted what treatments were effective for the individual. The levels can be used to generate values of which is a subject's value is compared, and a treatment or therapy can be selected for the individual.

In another embodiment, the threshold level of expression is a cut-off value. For example, the level of deregulation is measured relative to a control amount—a cut-off value. The cut-off level may be a statistically validated level or range which defines up-regulation or down-regulation or normal regulation or the control may be determined on a subject of known disease status (e.g. an unhealthy or disease control). Alternatively, predetermined ΔCt levels are obtained, for example by qPCR (as discussed above), associated with a healthy or not healthy subject and a ΔCt cut-off value selected to diagnose the disease state or a stage of the disease.

The present inventors have demonstrated that 28 serum exosomal miRNA were found to be significantly deregulated in Parkinson's disease patients, relative to healthy controls. The present inventors have also demonstrated that hsa-miR-222-3p (SEQ ID NO: 1) and hsa-miR-30a-5p (SEQ ID NO: 2), significantly differentially expressed in serum exosomes from Parkinson's disease patients and brain tissue exosomes of Parkinson's disease patients, relative to healthy controls. The remaining 26 serum exosomal miRNAs significantly deregulated in serum samples were also found differentially expressed in brain tissue exosomes of Parkinson's disease patients.

In particular, the present inventors have demonstrated that 21 exosomal miRNA were downregulated in serum of Parkinson's disease patients relative to healthy controls: hsa-miR-122-5p (SEQ ID NO: 3), hsa-miR-125b-5p (SEQ ID NO: 4), hsa-miR-133a-3p (SEQ ID NO: 5), hsa-miR-146b-5p (SEQ ID NO: 6), hsa-miR-181a-5p (SEQ ID NO: 7), hsa-miR-183-5p (SEQ ID NO: 8), hsa-miR-192-5p (SEQ ID NO: 9), hsa-miR-193a-5p (SEQ ID NO: 10), hsa-miR-208a-3p (SEQ ID NO: 11), hsa-miR-214-3p (SEQ ID NO: 12), hsa-miR-222-3p (SEQ ID NO: 1), hsa-miR-30a-5p (SEQ ID NO: 2), hsa-miR-31-5p (SEQ ID NO: 13), hsa-miR-34a-5p (SEQ ID NO: 14), hsa-miR-3529-3p (SEQ ID NO: 15), hsa-miR-375-3p (SEQ ID NO: 16), hsa-miR-378a-3p (SEQ ID NO: 17), hsa-miR-489-3p (SEQ ID NO: 18), hsa-miR-505-3p (SEQ ID NO: 19), hsa-miR-7-5p (SEQ ID NO: 20) and hsa-miR-769-5p (SEQ ID NO: 21).

The present inventors have also demonstrated that 7 exosomal miRNA were upregulated in serum of Parkinson's disease patients relative to healthy controls: hsa-miR-1306-5p (SEQ ID NO: 22), hsa-miR-199a-5p (SEQ ID NO: 23), hsa-miR-26a-5p (SEQ ID NO: 24), hsa-miR-339-5p (SEQ ID NO: 25), hsa-miR-4433-3p (SEQ ID NO: 26), hsa-miR-4433b-5p (SEQ ID NO: 27), and hsa-miR-766-3p (SEQ ID NO: 28).

The present inventors have also demonstrated that 16 exosomal miRNA were significantly upregulated in brain tissue of Parkinson's disease patients relative to healthy controls: hsa-miR-324-5p, hsa-miR-99a-3p, hsa-miR-221-3p, hsa-miR-30e-5p, hsa-miR-30a-5p, hsa-miR-365a-3p, hsa-miR-143-3p, hsa-miR-222-3p, hsa-miR-27a-3p, hsa-miR-29a-3p, hsa-miR-219a-5p, hsa-miR-29c-3p, hsa-miR-130a-3p, hsa-let-7b-3p, hsa-miR-345-5p, hsa-miR-873-5p.

Accordingly, in one aspect the present invention provides a method comprising measuring the level of expression of at least one small non-coding RNA comprising a nucleotide sequence selected from the group consisting of SEQ ID NOs:1 to 28, wherein an increased or decreased level of expression of at least one small non-coding RNA selected from the group consisting of SEQ ID NOs:1 to 28, compared to the reference level is indicative of Parkinson's disease or a predisposition to Parkinson's disease.

In another aspect the present invention provides a method comprising measuring the level of expression of at least two small non-coding RNA comprising a nucleotide sequence selected from the group consisting of SEQ ID NOs:1 to 28, wherein an increased or decreased level of expression of at least two small non-coding RNA selected from the group consisting of SEQ ID NOs:1 to 28, compared to the reference level is indicative of Parkinson's disease or a predisposition to Parkinson's disease.

In another aspect the present invention provides a method comprising measuring the level of expression of at least three small non-coding RNA comprising a nucleotide sequence selected from the group consisting of SEQ ID NOs:1 to 28, wherein an increased or decreased level of expression of at least three small non-coding RNA selected from the group consisting of SEQ ID NOs:1 to 28, compared to the reference level is indicative of Parkinson's disease or a predisposition to Parkinson's disease.

Importantly, the present inventors have also demonstrated that 4 exosomal miRNA were significantly deregulated in serum of Parkinson's disease patients relative to healthy controls and can be used to diagnose a disease state of a prion disease in humans: hsa-miR-222-3p (SEQ ID NO: 1), hsa-miR-133a-3p (SEQ ID NO: 5), hsa-miR-181a-5p (SEQ ID NO: 7), and hsa-miR-1306-5p (SEQ ID NO: 22)

Accordingly, in another aspect the present invention provides a method as described herein wherein an increased or decreased level of expression of at least one, at least two, or at least three small non-coding RNA selected from the group consisting of SEQ ID NOs: 1, 5, 7 and 22 and at least one, at least two, at least three, at least four or at least five small non-coding RNA selected from the group consisting of SEQ ID NOs: 2 to 4, 6, 8 to 21 and 23 to 28, compared to the reference level is indicative of Parkinson's disease or a predisposition to Parkinson's disease.

In another aspect the present invention provides a method as described herein wherein an increased or decreased level of expression of at least three small non-coding RNA selected from the group consisting of SEQ ID NOs: 1, 5, 7 and 22 and at least five small non-coding RNA selected from the group consisting of SEQ ID NOs: 2 to 4, 6, 8 to 21 and 23 to 28, compared to the reference level is indicative of Parkinson's disease or a predisposition to Parkinson's disease.

In a preferred embodiment, wherein the disease is Parkinson's disease or a predisposition to Parkinson's disease, the at least one miRNA is selected from the group consisting of hsa-miR-1306-5p, hsa-miR-199a-5p, hsa-miR-181a-5p, hsa-miR-133a-3p, hsa-miR-489-3p, hsa-miR-183-5p, hsa-miR-192-5p, hsa-miR-222-3p and hsa-miR-30a-50, hsa-miR-4433-3p, hsa-miR-766-3p-hsa-miR-339 and hsa-miR-26a-5p, hsa-miR-122-5p, hsa-miR-31-5p, hsa-miR-34a-5p, hsa-miR-193a-5p, hsa-miR-7-5p, hsa-miR-208a-3p and hsa-miR-378-a-3p.

In a preferred embodiment, wherein the disease is Parkinson's disease or a predisposition to Parkinson's disease, the at least one miRNA is selected from the group consisting of hsa-miR-1306-5p (SEQ ID NO: 22), hsa-miR-181a-5p (SEQ ID NO: 7), hsa-miR-193a-5p (SEQ ID NO: 10), hsa-miR-199a-5p (SEQ ID NO: 23), and hsa-miR-122-5p (SEQ ID NO: 3). More preferably, the at least one miRNA is hsa-miR-1306-5p (SEQ ID NO: 22) in combination with at least one, at least two or at least three of hsa-miR-181a-5p (SEQ ID NO: 7), hsa-miR-193a-5p (SEQ ID NO: 10), hsa-miR-199a-5p (SEQ ID NO: 23), and hsa-miR-122-5p (SEQ ID NO: 3).

The present inventors have demonstrated that 11 serum exosomal miRNA were found to be significantly deregulated in patients with dementia, based on cognitive scores (e.g. low cognition), relative to healthy controls, as is shown in EXAMPLE 11: hsa-miR-1306-5p (SEQ ID NO: 22), hsa-miR-342-3p (SEQ ID NO: 79), hsa-miR-15b-3p (SEQ ID NO: 71), hsa-miR-15a-5p (SEQ ID NO: 72), hsa-miR-143-3p (SEQ ID NO: 73), hsa-miR-335-5p (SEQ ID NO: 74), hsa-miR-106b-5p (SEQ ID NO: 75), hsa-miR-101-3p (SEQ ID NO: 61), hsa-miR-106a-5p (SEQ ID NO: 76), hsa-miR-20a-5p (SEQ ID NO: 77), and hsa-miR-30e-5p (SEQ ID NO: 78).

Accordingly, in a preferred embodiment, wherein the disease is a neurodegenerative disease or a predisposition to a neurodegenerative disease, the at least one miRNA is selected from the group consisting of hsa-miR-1306-5p (SEQ ID NO: 22), hsa-miR-342-3p (SEQ ID NO: 79), hsa-miR-15b-3p (SEQ ID NO: 71), hsa-miR-15a-5p (SEQ ID NO: 72), hsa-miR-143-3p (SEQ ID NO: 73), hsa-miR-335-5p (SEQ ID NO: 74), hsa-miR-106b-5p (SEQ ID NO: 75), hsa-miR-101-3p (SEQ ID NO: 61), hsa-miR-106a-5p (SEQ ID NO: 76), hsa-miR-20a-5p (SEQ ID NO: 77), and hsa-miR-30e-5p (SEQ ID NO: 78). More preferably, the at least one miRNA is hsa-miR-1306-5p (SEQ ID NO: 22) in combination with at least one, at least two, at least three, at least four or at least five of hsa-miR-342-3p (SEQ ID NO: 79), hsa-miR-15b-3p (SEQ ID NO: 71), hsa-miR-15a-5p (SEQ ID NO: 72), hsa-miR-143-3p (SEQ ID NO: 73), hsa-miR-335-5p (SEQ ID NO: 74), hsa-miR-106b-5p (SEQ ID NO: 75), hsa-miR-101-3p (SEQ ID NO: 61), hsa-miR-106a-5p (SEQ ID NO: 76), hsa-miR-20a-5p (SEQ ID NO: 77), and hsa-miR-30e-5p (SEQ ID NO: 78). In a preferred embodiment, the neurodegenerative disease is dementia, or Alzheimer's Disease, or a predisposition to dementia, or Alzheimer's Disease.

As shown in Example 12 and Example 13, the present inventors have also demonstrated that 2 exosomal miRNA significantly deregulated in serum of patents with AD also deregulated in brain derived exosomes of patients with AD, relative to healthy controls, can be used to diagnose a disease state of AD in humans: hsa-miR-143-3p (SEQ ID NO: 73) and hsa-miR-30e-5p (SEQ ID NO: 78).

Accordingly, in a preferred embodiment, wherein the disease is AD or a predisposition to AD, the at least one miRNA is miR-143-3p (SEQ ID NO: 73) and/or hsa-miR-30e-5p (SEQ ID NO: 78). Importantly, the serum exosomal miRNA found to be significantly deregulated in patients with AD, and also found to be significantly deregulated in BDEs of patients with AD, relative to healthy controls can each be used alone, or in combination, with miRNA deregulated in other neurodegenerative disorders, such as dementia.

Accordingly, in a preferred embodiment, wherein the disease is AD or a predisposition to a AD, the at least one miRNA is selected from the group consisting miR-143-3p (SEQ ID NO: 73) and/or hsa-miR-30e-5p (SEQ ID NO: 78), in combination with at least one, at least two, at least three, at least four or at least five of hsa-miR-1306-5p (SEQ ID NO: 22), hsa-miR-342-3p (SEQ ID NO: 79), hsa-miR-15b-3p (SEQ ID NO: 71), hsa-miR-15a-5p (SEQ ID NO: 72), hsa-miR-143-3p (SEQ ID NO: 73), hsa-miR-335-5p (SEQ ID NO: 74), hsa-miR-106b-5p (SEQ ID NO: 75), hsa-miR-101-3p (SEQ ID NO: 61), hsa-miR-106a-5p (SEQ ID NO: 76), hsa-miR-20a-5p (SEQ ID NO: 77), and hsa-miR-30e-5p (SEQ ID NO: 78).

The 11 serum exosomal miRNA found to be significantly deregulated in patients with dementia, relative to healthy controls can each be used alone, or in combination, with miRNA deregulated in other neurodegenerative disorders, such as those described herein. For example, the 11 serum exosomal miRNA found to be significantly deregulated in patients with dementia can be used to differentiate different neurodegenerative disorders, when used in combination with miRNA deregulated in other neurodegenerative disorders such as PD and CJD.

Accordingly, in a preferred embodiment, wherein the disease is Parkinson's disease or a predisposition to Parkinson's disease, the at least one miRNA is selected from the group consisting of hsa-miR-1306-5p (SEQ ID NO: 22), hsa-miR-342-3p (SEQ ID NO: 79), hsa-miR-15b-3p (SEQ ID NO: 71), hsa-miR-15a-5p (SEQ ID NO: 72), hsa-miR-143-3p (SEQ ID NO: 73), hsa-miR-335-5p (SEQ ID NO: 74), hsa-miR-106b-5p (SEQ ID NO: 75), hsa-miR-101-3p (SEQ ID NO: 61), hsa-miR-106a-5p (SEQ ID NO: 76), hsa-miR-20a-5p (SEQ ID NO: 77), and hsa-miR-30e-5p (SEQ ID NO: 78). More preferably, the at least one miRNA is hsa-miR-1306-5p (SEQ ID NO: 22) in combination with at least one, at least two, at least three, at least four or at least five of hsa-miR-342-3p (SEQ ID NO: 79), hsa-miR-15b-3p (SEQ ID NO: 71), hsa-miR-15a-5p (SEQ ID NO: 72), hsa-miR-143-3p (SEQ ID NO: 73), hsa-miR-335-5p (SEQ ID NO: 74), hsa-miR-106b-5p (SEQ ID NO: 75), hsa-miR-101-3p (SEQ ID NO: 61), hsa-miR-106a-5p (SEQ ID NO: 76), hsa-miR-20a-5p (SEQ ID NO: 77), and hsa-miR-30e-5p (SEQ ID NO: 78).

In another preferred embodiment, wherein the disease is Parkinson's disease or a predisposition to Parkinson's disease, the at least one miRNA is hsa-miR-1306-5p (SEQ ID NO: 22) in combination with at least one, at least two or at least three of hsa-miR-181a-5p (SEQ ID NO: 7), hsa-miR-193a-5p (SEQ ID NO: 10), hsa-miR-199a-5p (SEQ ID NO: 23), and hsa-miR-122-5p (SEQ ID NO: 3), and at least one, at least two, at least three, at least four or at least five of hsa-miR-342-3p (SEQ ID NO: 79), hsa-miR-15b-3p (SEQ ID NO: 71), hsa-miR-15a-5p (SEQ ID NO: 72), hsa-miR-143-3p (SEQ ID NO: 73), hsa-miR-335-5p (SEQ ID NO: 74), hsa-miR-106b-5p (SEQ ID NO: 75), hsa-miR-101-3p (SEQ ID NO: 61), hsa-miR-106a-5p (SEQ ID NO: 76), hsa-miR-20a-5p (SEQ ID NO: 77), and hsa-miR-30e-5p (SEQ ID NO: 78).

The present inventors have demonstrated serum exosomal miRNA significantly deregulated in animals with prion disease, relative to uninfected animals. In particular the present inventors have demonstrated that six miRNAs (mmu-miR-1306-5p (SEQ ID NO: 29), mmu-miR-130a-3p (SEQ ID NO: 30), mmu-miR-148b-3p (SEQ ID NO: 31), mmu-miR-92a-3p (SEQ ID NO: 32), mmu-miR-142-3p (SEQ ID NO: 33) and mmu-miR-15b-5p (SEQ ID NO: 34)) that were deregulated at 3 wpi, eight miRNAs (mmu-miR-181a-5p (SEQ ID NO: 35), mmu-miR-1a-3p (SEQ ID NO: 36), mmu-miR-223-5p (SEQ ID NO: 37), mmu-miR-423-3p (SEQ ID NO: 38), mmu-miR-146a-5p (SEQ ID NO: 39), mmu-miR-16-5p (SEQ ID NO: 40), mmu-miR-205-5p (SEQ ID NO: 41) and mmu-miR-222-3p (SEQ ID NO: 42) deregulated at 13 wpi and 11 miRNAs (mmu-miR-142-3p (SEQ ID NO: 43), mmu-miR-15b-5p (SEQ ID NO: 44), mmu-miR-146a-5p (SEQ ID NO: 45), mmu-miR-16-5p (SEQ ID NO: 46), mmu-miR-205-5p (SEQ ID NO: 47), mmu-miR-222-3p (SEQ ID NO: 48), mmu-miR-10b-5p (SEQ ID NO: 49), mmu-miR-133a-3p (SEQ ID NO: 50), mmu-miR-142-5p (SEQ ID NO: 51), mmu-miR-203-3p (SEQ ID NO: 52) and mmu-miR-215-5p (SEQ ID NO: 53)) deregulated at terminal stage.

Under a standard nomenclature system, miRNA names are assigned to experimentally confirmed miRNAs. The prefix "mir" is followed by a dash and a number, the latter often indicating order of naming. The uncapitalized "mir-" refers to the pre-miRNA, while a capitalized "miR-" refers to the mature form. miRNAs with nearly identical sequences bar one or two nucleotides are annotated with an additional lower case letter. For example, miR-123a would be closely related to miR-123b. miRNAs that are 100% identical but are encoded at different places in the genome are indicated with additional dash-number suffix: miR-123-1 and miR-123-2 are identical but are produced from different pre-miRNAs. Species of origin is designated with a three-letter prefix, e.g., hsa-miR-123 would be from human (*Homo sapiens*) and mmu-miR-123 would be a mouse (*Mus musculus*) miRNA. microRNAs originating from the 3' or 5' end of a pre-miRNA are denoted with a −3p or −5p suffix. (In the past, this distinction was also made with ‘s’ (sense) and ‘as’ (antisense)).

An asterisk following the name indicates that the miRNA is an anti-miRNA to the miRNA without an asterisk (e.g. miR-123* is an anti-miRNA to miR-123). When relative expression levels are known, an asterisk following the name indicates a miRNA expressed at low levels relative to the miRNA in the opposite arm of a hairpin. For example, miR-123 and miR-123* would share a pre-miRNA hairpin, but relatively more miR-123 would be found in a cell or an extracellular vesicle.

Also, it is understood that e.g. hsa-miR-123 is identical to miR-123, and that this may also be denoted miR.123 as well as miR-123 or hsa-miR-123 or hsa.miR.123.

miRBase is the central online repository for microRNA (miRNA) nomenclature, sequence data, annotation and target prediction, and may be accessed via www.mirbase.org. While the standard nomenclature for miRNA is well known, a list of exemplary miRNAs is provided below with reference to SEQ ID as used herein, name, miRBase accession, and sequence.

| SEQ ID NO | Name | miRBase Accession | Sequence |
|---|---|---|---|
| SEQ ID NO: 1 | hsa-miR-222-3p | MIMAT0000279 | AGCUACAUCUGGCUACUGGGU |
| SEQ ID NO: 2 | hsa-miR-30a-5p | MIMAT0000087 | UGUAAACAUCCUCGACUGGAAG |
| SEQ ID NO: 3 | hsa-miR-122-5p | MIMAT0000421 | UGGAGUGUGACAAUGGUGUUUG |
| SEQ ID NO: 4 | hsa-miR-125b-5p | MIMAT0000423 | UCCCUGAGACCCUAACUUGUGA |
| SEQ ID NO: 5 | hsa-miR-133a-3p | MIMAT0000427 | UUUGGUCCCCUUCAACCAGCUG |
| SEQ ID NO: 6 | hsa-miR-146b-5p | MIMAT0002809 | UGAGAACUGAAUUCCAUAGGCU |
| SEQ ID NO: 7 | hsa-miR-181a-5p | MIMAT0000256 | AACAUUCAACGCUGUCGGUGAGU |
| SEQ ID NO: 8 | hsa-miR-183-5p | MIMAT0000261 | UAUGGCACUGGUAGAAUUCACU |
| SEQ ID NO: 9 | hsa-miR-192-5p | MIMAT0000222 | CUGACCUAUGAAUUGACAGCC |
| SEQ ID NO: 10 | hsa-miR-193a-5p | MIMAT0004614 | UGGGUCUUUGCGGGCGAGAUGA |
| SEQ ID NO: 11 | hsa-miR-208a-3p | MIMAT0000241 | AUAAGACGAGCAAAAAGCUUGU |
| SEQ ID NO: 12 | hsa-miR-214-3p | MIMAT0000271 | ACAGCAGGCACAGACAGGCAGU |
| SEQ ID NO: 13 | hsa-miR-31-5p | MIMAT0000089 | AGGCAAGAUGCUGGCAUAGCU |
| SEQ ID NO: 14 | hsa-miR-34a-5p | MIMAT0000255 | UGGCAGUGUCUUAGCUGGUUGU |
| SEQ ID NO: 15 | hsa-miR-3529-3p | MIMAT0022741 | AACAACAAAAUCACUAGUCUUCCA |
| SEQ ID NO: 16 | hsa-miR-375-3p | MIMAT0000728 | UUUGUUCGUUCGGCUCGCGUGA |
| SEQ ID NO: 17 | hsa-miR-378a-3p | MIMAT0000732 | ACUGGACUUGGAGUCAGAAGGC |
| SEQ ID NO: 18 | hsa-miR-489-3p | MIMAT0002805 | GUGACAUCACAUAUACGGCAGC |
| SEQ ID NO: 19 | hsa-miR-505-3p | MIMAT0002876 | CGUCAACACUUGCUGGUUUCCU |
| SEQ ID NO: 20 | hsa-miR-7-5p | MIMAT0000252 | UGGAAGACUAGUGAUUUUGUUGUU |
| SEQ ID NO: 21 | hsa-miR-769-5p | MIMAT0003886 | UGAGACCUCUGGGUUCUGAGCU |
| SEQ ID NO: 22 | hsa-miR-1306-5p | MIMAT0022726 | CCACCUCCCCUGCAAACGUCCA |
| SEQ ID NO: 23 | hsa-miR-199a-5p | MIMAT0000231 | CCCAGUGUUCAGACUACCUGUUC |
| SEQ ID NO: 24 | hsa-miR-26a-5p | MIMAT0000082 | UUCAAGUAAUCCAGGAUAGGCU |
| SEQ ID NO: 25 | hsa-miR-339-5p | MIMAT0000764 | UCCCUGUCCUCCAGGAGCUCACG |
| SEQ ID NO: 26 | hsa-miR-4433-3p | MIMAT0018949 | ACAGGAGUGGGGGUGGGACAU |
| SEQ ID NO: 27 | hsa-miR-4433b-5p | MIMAT0030413 | AUGUCCCACCCCCACUCCUGU |
| SEQ ID NO: 28 | hsa-miR-766-3p | MIMAT0003888 | ACUCCAGCCCCACAGCCUCAGC |
| SEQ ID NO: 29 | mmu-miR-1306-5p | MIMAT0019136 | CACCACCUCCCCUGCAAACGUCC |

-continued

| SEQ ID NO | Name | miRBase Accession | Sequence |
|---|---|---|---|
| SEQ ID NO: 30 | mmu-miR-130a-3p | MIMAT0000141 | CAGUGCAAUGUUAAAAGGGCAU |
| SEQ ID NO: 31 | mmu-miR-148b-3p | MIMAT0000580 | UCAGUGCAUCACAGAACUUUGU |
| SEQ ID NO: 32 | mmu-miR-92a-3p | MIMAT0000539 | UAUUGCACUUGUCCCGGCCUG |
| SEQ ID NO: 33 | mmu-miR-142-3p | MIMAT0000155 | UGUAGUGUUUCCUACUUUAUGGA |
| SEQ ID NO: 34 | mmu-miR-15b-5p | MIMAT0000124 | UAGCAGCACAUCAUGGUUUACA |
| SEQ ID NO: 35 | mmu-miR-181a-5p | MIMAT0000210 | AACAUUCAACGCUGUCGGUGAGU |
| SEQ ID NO: 36 | mmu-miR-1a-3p | MIMAT0000123 | UGGAAUGUAAAGAAGUAUGUAU |
| SEQ ID NO: 37 | mmu-miR-223-5p | MIMAT0017056 | CGUGUAUUUGACAAGCUGAGUUG |
| SEQ ID NO: 38 | mmu-miR-423-3p | MIMAT0003454 | AGCUCGGUCUGAGGCCCCUCAGU |
| SEQ ID NO: 39 | mmu-miR-146a-5p | MIMAT0000158 | UGAGAACUGAAUUCCAUGGGUU |
| SEQ ID NO: 40 | mmu-miR-16-5p | MIMAT0000527 | UAGCAGCACGUAAAUAUUGGCG |
| SEQ ID NO: 41 | mmu-miR-205-5p | MIMAT0000238 | UCCUUCAUUCCACCGGAGUCUG |
| SEQ ID NO: 42 | mmu-miR-222-3p | MIMAT0000670 | AGCUACAUCUGGCUACUGGGUCU |
| SEQ ID NO: 43 | mmu-miR-142-3p | MIMAT0000155 | UGUAGUGUUUCCUACUUUAUGGA |
| SEQ ID NO: 44 | mmu-miR-15b-5p | MIMAT0000124 | UAGCAGCACAUCAUGGUUUACA |
| SEQ ID NO: 45 | mmu-miR-146a-5p | MIMAT0000158 | UGAGAACUGAAUUCCAUGGGUU |
| SEQ ID NO: 46 | mmu-miR-16-5p | MIMAT0000527 | UAGCAGCACGUAAAUAUUGGCG |
| SEQ ID NO: 47 | mmu-miR-205-5p | MIMAT0000238 | UCCUUCAUUCCACCGGAGUCUG |
| SEQ ID NO: 48 | mmu-miR-222-3p | MIMAT0000670 | AGCUACAUCUGGCUACUGGGUCU |
| SEQ ID NO: 49 | mmu-miR-10b-5p | MIMAT0000208 | UACCCUGUAGAACCGAAUUUGUG |
| SEQ ID NO: 50 | mmu-miR-133a-3p | MIMAT0000145 | UUUGGUCCCCUUCAACCAGCUG |
| SEQ ID NO: 51 | mmu-miR-142-5p | MIMAT0000154 | CAUAAAGUAGAAAGCACUACU |
| SEQ ID NO: 52 | mmu-miR-203-3p | MIMAT0000236 | GUGAAAUGUUUAGGACCACUAG |
| SEQ ID NO: 53 | mmu-miR-215-5p | MIMAT0000904 | AUGACCUAUGAUUUGACAGAC |
| SEQ ID NO: 54 | hsa-miR-10b-5p | MIMAT0000254 | UACCCUGUAGAACCGAAUUUGUG |
| SEQ ID NO: 55 | hsa-miR-133a-3p | MIMAT0000427 | UUUGGUCCCCUUCAACCAGCUG |
| SEQ ID NO: 56 | hsa-miR-142-5p | MIMAT0000433 | CAUAAAGUAGAAAGCACUACU |
| SEQ ID NO: 57 | hsa-miR-203a-3p | MIMAT0000264 | GUGAAAUGUUUAGGACCACUAG |
| SEQ ID NO: 58 | hsa-miR-1-3p | MIMAT0000416 | UGGAAUGUAAAGAAGUAUGUAU |
| SEQ ID NO: 59 | hsa-miR-181a-5p | MIMAT0000256 | AACAUUCAACGCUGUCGGUGAGU |
| SEQ ID NO: 60 | hsa-miR-423-3p | MIMAT0001340 | AGCUCGGUCUGAGGCCCCUCAGU |
| SEQ ID NO: 61 | hsa-miR-101-3p | MIMAT0000099 | UACAGUACUGUGAUAACUGAA |
| SEQ ID NO: 62 | hsa-miR-146a-5p | MIMAT0000449 | UGAGAACUGAAUUCCAUGGGUU |
| SEQ ID NO: 63 | hsa-miR-16-5p | MIMAT0000069 | UAGCAGCACGUAAAUAUUGGCG |
| SEQ ID NO: 64 | hsa-miR-205-5p | MIMAT0000266 | UCCUUCAUUCCACCGGAGUCUG |
| SEQ ID NO: 65 | hsa-miR-222-3p | MIMAT0000279 | AGCUACAUCUGGCUACUGGGU |
| SEQ ID NO: 66 | hsa-miR-1306-5p | MIMAT0022726 | CCACCUCCCCUGCAAACGUCCA |
| SEQ ID NO: 67 | hsa-miR-130a-3p | MIMAT0000425 | CAGUGCAAUGUUAAAAGGGCAU |
| SEQ ID NO: 68 | hsa-miR-148b-3p | MIMAT0000759 | UCAGUGCAUCACAGAACUUUGU |

-continued

| SEQ ID NO | Name | miRBase Accession | Sequence |
|---|---|---|---|
| SEQ ID NO: 69 | hsa-miR-92a-3p | MIMAT0000092 | UAUUGCACUUGUCCCGGCCUGU |
| SEQ ID NO: 70 | hsa-miR-142-3p | MIMAT0000434 | UGUAGUGUUUCCUACUUUAUGGA |
| SEQ ID NO: 71 | hsa-miR-15b-3p | MIMAT0004586 | CGAAUCAUUAUUUGCUGCUCUA |
| SEQ ID NO: 72 | hsa-miR-15a-5p | MIMAT0000068 | UAGCAGCACAUAAUGGUUUGUG |
| SEQ ID NO: 73 | hsa-miR-143-3p | MIMAT0000435 | UGAGAUGAAGCACUGUAGCUC |
| SEQ ID NO: 74 | hsa-miR-335-5p | MIMAT0000765 | UCAAGAGCAAUAACGAAAAAUGU |
| SEQ ID NO: 75 | hsa-miR-106b-5p | MIMAT0000680 | UAAAGUGCUGACAGUGCAGAU |
| SEQ ID NO: 76 | hsa-miR-106a-5p | MIMAT0000103 | AAAAGUGCUUACAGUGCAGGUAG |
| SEQ ID NO: 77 | hsa-miR-20a-5p | MIMAT0000075 | UAAAGUGCUUAUAGUGCAGGUAG |
| SEQ ID NO: 78 | hsa-miR-30e-5p | MIMAT0000692 | UGUAAACAUCCUUGACUGGAAG |
| SEQ ID NO: 79 | hsa-miR-342-3p | MIMAT0000753 | UCUCACACAGAAAUCGCACCCGU |

The present inventors have also demonstrated that serum exosomal miRNA can be used to diagnose a disease state of a prion disease. In particular, the present inventors have demonstrated serum exosomal miRNA from preclinical studies can be used to diagnose a disease state of CJD: hsa-miR-10b-5p (SEQ ID NO: 54), hsa-miR-133a-3p (SEQ ID NO: 5/SEQ ID NO: 55), hsa-miR-142-5p (SEQ ID NO: 56), hsa-miR-203a-3p (SEQ ID NO: 57), hsa-miR-1-3p (SEQ ID NO: 58), hsa-miR-181a-5p (SEQ ID NO: 7/SEQ ID NO: 59), hsa-miR-423-3p (SEQ ID NO: 60), hsa-miR-101-3p (SEQ ID NO: 61), hsa-miR-146a-5p (SEQ ID NO: 62), hsa-miR-16-5p (SEQ ID NO: 63), hsa-miR-205-5p (SEQ ID NO: 64), hsa-miR-222-3p (SEQ ID NO: 1/SEQ ID NO 65), hsa-miR-1306-5p (SEQ ID NO: 22/SEQ ID NO: 66), hsa-miR-130a-3p (SEQ ID NO: 67), hsa-miR-148b-3p (SEQ ID NO: 68), hsa-miR-92a-3p (SEQ ID NO: 69), hsa-miR-142-3p (SEQ ID NO: 70).

As indicated above, the present inventors have demonstrated that 11 serum exosomal miRNA were found to be significantly deregulated in patients with dementia, relative to healthy controls, as is shown in EXAMPLE 11: hsa-miR-1306-5p (SEQ ID NO: 22), hsa-miR-342-3p (SEQ ID NO: 79), hsa-miR-15b-3p (SEQ ID NO: 71), hsa-miR-15a-5p (SEQ ID NO: 72), hsa-miR-143-3p (SEQ ID NO: 73), hsa-miR-335-5p (SEQ ID NO: 74), hsa-miR-106b-5p (SEQ ID NO: 75), hsa-miR-101-3p (SEQ ID NO: 61), hsa-miR-106a-5p (SEQ ID NO: 76), hsa-miR-20a-5p (SEQ ID NO: 77), and hsa-miR-30e-5p (SEQ ID NO: 78). The 11 serum exosomal miRNA found to be significantly deregulated in patients with dementia, relative to healthy controls can each be used alone, or in combination, with miRNA deregulated in other neurodegenerative disorders, such as CJD.

Importantly, the present inventors have demonstrated that serum exosomal miRNA can be used to diagnose a disease state of a prion disease in humans: hsa-miR-423-3p (SEQ ID NO: 60), hsa-miR-101-3p (SEQ ID NO: 61), hsa-miR-10b-5p (SEQ ID NO: 54), hsa-miR-1306-5p (SEQ ID NO: 22), hsa-miR-130a-3p (SEQ ID NO: 67), hsa-miR-133a-3p (SEQ ID NO: 5), hsa-miR-142-3p (SEQ ID NO: 70), miR-92a-3p (SEQ ID NO: 69), hsa-miR-146a-5p (SEQ ID NO: 62), hsa-miR-148b-3p (SEQ ID NO: 68), hsa-miR-16-5p (SEQ ID NO: 63), hsa-miR-222-3p (SEQ ID NO: 1).

Accordingly, in one aspect the present invention provides a method comprising measuring the level of expression of at least one small non-coding RNA comprising a nucleotide sequence selected from the group consisting of SEQ ID NOs:54 to 70, wherein an increased or decreased level of expression of at least one small non-coding RNA selected from the group consisting of SEQ ID NOs:54 to 70 compared to the reference level is indicative of a prion disease or a predisposition to a prion disease.

In another aspect the present invention provides a method comprising measuring the level of expression of at least two small non-coding RNA comprising a nucleotide sequence selected from the group consisting of SEQ ID NOs:54 to 70, wherein an increased or decreased level of expression of at least two small non-coding RNA selected from the group consisting of SEQ ID NOs:54 to 70, compared to the reference level is indicative of a prion disease or a predisposition to a prion disease.

In another aspect the present invention provides a method comprising measuring the level of expression of at least three small non-coding RNA comprising a nucleotide sequence selected from the group consisting of SEQ ID NOs:54 to 70, wherein an increased or decreased level of expression of at least three small non-coding RNA selected from the group consisting of SEQ ID NOs:54 to 70, compared to the reference level is indicative of a prion disease or a predisposition to a prion disease.

As indicated herein, the present inventors have also demonstrated that 5 exosomal miRNA significantly deregulated in serum of patents with a prion disease, relative to healthy controls, can be used to diagnose a disease state of a prion disease in humans: hsa-miR-222-3p (SEQ ID NO: 1), hsa-miR-133a-3p (SEQ ID NO: 5), hsa-miR-181a-5p (SEQ ID NO: 7), and hsa-miR-1306-5p (SEQ ID NO: 22).

Accordingly, in another aspect the present invention provides a method as described herein wherein an increased or decreased level of expression of at least one, at least two, or at least three small non-coding RNA selected from the group consisting of SEQ ID NOs: 1, 5, 7 and 22 and at least one, at least two, at least three, at least four or at least five small non-coding RNA selected from the group consisting of SEQ ID NOs: 54, 56 to 58, 60 to 64, and 67 to 70, compared to the reference level is indicative of a prion disease or a predisposition to a prion disease.

In a preferred embodiment, wherein the disease is a prion disease or a predisposition to a prion disease, the at least one miRNA is selected from the group consisting of hsa-miR-1306-5p (SEQ ID NO: 22), hsa-miR-142-5p (SEQ ID NO: 56), hsa-miR-146a-5p (SEQ ID NO: 62), hsa-miR-142-3p (SEQ ID NO: 70), hsa-miR-1-3p (SEQ ID NO: 58) and hsa-miR-423-3p (SEQ ID NO: 60). More preferably, the at least one miRNA is hsa-miR-1306-5p (SEQ ID NO: 22) in combination with at least one, at least two or at least three of hsa-miR-142-5p (SEQ ID NO: 56), hsa-miR-146a-5p (SEQ ID NO: 62), hsa-miR-142-3p (SEQ ID NO: 70), and hsa-miR-1-3p (SEQ ID NO: 58) and hsa-miR-423-3p (SEQ ID NO: 60).

The present inventors have demonstrated that 11 serum exosomal miRNA were found to be significantly deregulated in patients with dementia, relative to healthy controls, as shown in EXAMPLE 11: hsa-miR-1306-5p (SEQ ID NO: 22), hsa-miR-342-3p (SEQ ID NO: 79), hsa-miR-15b-3p (SEQ ID NO: 71), hsa-miR-15a-5p (SEQ ID NO: 72), hsa-miR-143-3p (SEQ ID NO: 73), hsa-miR-335-5p (SEQ ID NO: 74), hsa-miR-106b-5p (SEQ ID NO: 75), hsa-miR-101-3p (SEQ ID NO: 61), hsa-miR-106a-5p (SEQ ID NO: 76), hsa-miR-20a-5p (SEQ ID NO: 77), and hsa-miR-30e-5p (SEQ ID NO: 78).

The 11 serum exosomal miRNA found to be significantly deregulated in patients with dementia, relative to healthy controls can be used alone, or in combination, with serum exosomal miRNA deregulated in CJD.

Accordingly, in a preferred embodiment, wherein the disease a prion disease or a predisposition to a prion disease, the at least one miRNA is selected from the group consisting of hsa-miR-1306-5p (SEQ ID NO: 22), hsa-miR-342-3p (SEQ ID NO: 79), hsa-miR-15b-3p (SEQ ID NO: 71), hsa-miR-15a-5p (SEQ ID NO: 72), hsa-miR-143-3p (SEQ ID NO: 73), hsa-miR-335-5p (SEQ ID NO: 74), hsa-miR-106b-5p (SEQ ID NO: 75), hsa-miR-101-3p (SEQ ID NO: 61), hsa-miR-106a-5p (SEQ ID NO: 76), hsa-miR-20a-5p (SEQ ID NO: 77), and hsa-miR-30e-5p (SEQ ID NO: 78). More preferably, the at least one miRNA is hsa-miR-1306-5p (SEQ ID NO: 22) in combination with at least one, at least two, at least three, at least four or at least five of hsa-miR-342-3p (SEQ ID NO: 79), hsa-miR-15b-3p (SEQ ID NO: 71), hsa-miR-15a-5p (SEQ ID NO: 72), hsa-miR-143-3p (SEQ ID NO: 73), hsa-miR-335-5p (SEQ ID NO: 74), hsa-miR-106b-5p (SEQ ID NO: 75), hsa-miR-101-3p (SEQ ID NO: 61), hsa-miR-106a-5p (SEQ ID NO: 76), hsa-miR-20a-5p (SEQ ID NO: 77), and hsa-miR-30e-5p (SEQ ID NO: 78).

In another preferred embodiment, wherein the disease a prion disease or a predisposition to a prion disease, the at least one miRNA is hsa-miR-1306-5p (SEQ ID NO: 22) in combination with at least one, at least two or at least three of hsa-miR-142-5p (SEQ ID NO: 56), hsa-miR-146a-5p (SEQ ID NO: 62), hsa-miR-142-3p (SEQ ID NO: 70), hsa-miR-1-3p (SEQ ID NO: 58) and hsa-miR-423-3p (SEQ ID NO: 60), and at least one, at least two, at least three, at least four or at least five of hsa-miR-342-3p (SEQ ID NO: 79), hsa-miR-15b-3p (SEQ ID NO: 71), hsa-miR-15a-5p (SEQ ID NO: 72), hsa-miR-143-3p (SEQ ID NO: 73), hsa-miR-335-5p (SEQ ID NO: 74), hsa-miR-106b-5p (SEQ ID NO: 75), hsa-miR-101-3p (SEQ ID NO: 61), hsa-miR-106a-5p (SEQ ID NO: 76), hsa-miR-20a-5p (SEQ ID NO: 77), and hsa-miR-30e-5p (SEQ ID NO: 78).

In one embodiment, deregulation is a greater than 1.5 or −1.5 fold change in expression level. For example, an upregulated miRNA has a greater than 1.5 fold increase in expression level. A downregulated miRNA has a greater than 1.5 fold decrease in expression level. In one embodiment, significant deregulation is a greater than 1.5 or −1.5 fold change in expression level with a P value of less than or equal to 0.05. For example, a significantly upregulated miRNA has a greater than 1.5 fold increase in expression level with a P value of less than or equal to 0.05. A significantly downregulated miRNA has a greater than 1.5 fold decrease in expression level with a P value of less than or equal to 0.05.

In a preferred embodiment, wherein the disease is a prion disease or a predisposition to a prion disease, the at least one miRNA is selected from the group consisting of hsa-miR-101-3p, hsa-miR-1306-5p, hsa-miR-423-3p, hsa-miR-142-3p, hsa-miR-92a-3p and hsa-miR-10b-5p.

In one embodiment the prion disease is Creutzfeldt-Jakob disease (CJD) or a predisposition to CJD.

The level of expression of exosomal miRNA in sample can also be used to select an anti-disease therapy. Detection of exosomal miRNA can be used to determine the efficacy of a therapy or treatment, such as the relative improvement or deterioration of the subject's condition. Assessing exosomal miRNA from samples of patients treated with effective therapies or non-effective therapies can be determined and used as a reference for selecting a therapy for a subject. In another embodiment, as a subject's disease becomes progressively worse or better, the level of exosomal miRNA may change, and compared to a reference level of exosomal miRNA from patients that were in a worse or better stage of the disease.

The treatment or therapeutic selected based on exosomal miRNA can be a treatment for dementia, AD, PD or a prion disease.

In one embodiment, the treatment for dementia, AD, PD or a prion disease comprises administering to a patient at least one miRNA deregulated in the disease or predisposition to disease to be treated. For example, exosomes comprising miRNA at the reference level may be administered to the subject. In one embodiment, where there is an increased level of expression of the at least one small non-coding RNA, exosomes comprising the at least one miRNA at a level reduced relative to the reference level may be administered to the subject. In another embodiment, where there is a decreased level of expression of the at least one small non-coding RNA, exosomes comprising the at least one miRNA at a level increased relative to the reference level may be administered to the subject.

For example, in one embodiment, following measuring the level of expression of at least one small non-coding RNA comprising a nucleotide sequence selected from the group consisting of SEQ ID NOs: 1 to 79, in a sample from the subject, wherein the sample comprises extracellular vesicles; and comparing the level of expression of the at least one small non-coding RNA to a reference level of expression of the at least one small non-coding RNA, wherein an increased or decreased level of expression of the at least one compared to the reference level is indicative of a disease state or a stage of development of a disease state, a composition comprising miRNA and/or exosomes is administered to the subject.

In still a further embodiment, the present invention provides a method for delivery of small non-coding RNA comprising contacting a cell with a small non-coding RNA (e.g. a miRNA) and/or exosomes comprising a small non-coding RNA (e.g. a miRNA).

Detection of exosomal miRNA can also be used to determine the efficacy of an anti-disease therapy or treatment, such as the relative improvement or deterioration of the subject's condition. Exosomal miRNA of patients being treated for dementia, AD, PD or a prion disease can be determined and correlated to the improvement or beneficial efficacy, which is then used as a reference.

Exosomal miRNA can also be used monitor the progress of an anti-disease treatment regimen or treatment in a subject, or the recurrence of the disease.

Recurrence can be determined by periodically obtaining sample from a subject and monitoring exosomal miRNA expression levels periodically from a sample of the subject.

In one embodiment, a method described herein further comprises a psychological, behavioural, physiological and/or genetic assessment of the subject. In one aspect, the psychological assessment determines the presence and/or level of cognitive impairment.

In another aspect, a method described herein further comprises selecting a treatment or modifying a treatment for the disease state or the predisposition to the disease state, based on the diagnosis of disease state. For example, in some embodiments, the methods of the invention can further comprise the step of administering a therapeutic or preventive treatment to the subject that has been diagnosed as having the condition or as being at risk of progression to a more severe disease state or stage.

In another aspect, a method described herein further comprises administering to the subject a therapeutically effective amount of an anti-disease state therapy. For example, one or more symptoms of a neurodegenerative disease (such as PD, a prion disease, or AD) can be treated.

Non-limiting symptoms of a neurodegenerative disorder in a subject include difficulty lifting the front part of the foot and toes; weakness in arms, legs, feet, or ankles; hand weakness or clumsiness; slurring of speech; difficulty swallowing; muscle cramps; twitching in arms, shoulders, and tongue; difficulty chewing; difficulty breathing; muscle paralysis; partial or complete loss of vision; double vision; tingling or pain in parts of body; electric shock sensations that occur with head movements; tremor; unsteady gait; fatigue; dizziness; loss of memory; disorientation; misinterpretation of spatial relationships; difficulty reading or writing; difficulty concentrating and thinking; difficulty making judgments and decisions; difficulty planning and performing familiar tasks; depression; anxiety; social withdrawal; mood swings; irritability; aggressiveness; changes in sleeping habits; wandering; dementia; loss of automatic movements; impaired posture and balance; rigid muscles; bradykinesia; slow or abnormal eye movements; involuntary jerking or writhing movements (chorea); involuntary, sustained contracture of muscles (dystonia); lack of flexibility; lack of impulse control; and changes in appetite.

Symptoms of CJD can be treated: psychiatric symptoms like anxiety and depression can be treated with sedatives and antidepressants, myoclonic jerks can be handled with clonazepam or sodium valproate, opiates can help in pain, and seizures are very uncommon, and can be treated with antiepileptic drugs. One or more symptoms of PD can be treated using levodopa, COMT inhibitors, dopamine agonists, MAO-B inhibitors, surgery, and rehabilitation. Methods and compositions for treating and/or managing symptoms of dementia AD, PD and prion diseases are known in the field.

The present invention also provides are additional methods for diagnosing a neurodegenerative disorder described herein in a subject (e.g., a subject presenting with one or more symptoms of a neurodegenerative disorder or a subject not presenting a symptom of a neurodegenerative disorder (e.g., an undiagnosed and/or asymptomatic subject)). Also provided in the disclosure are prognostic methods and methods of treating a neurodegenerative disorder in a subject (e.g., methods of decreasing the rate of onset or the progression of symptoms (e.g., ataxia) of a neurodegenerative disorder in a subject).

A health care professional may also base a diagnosis, in part, on the subject's family history of a neurodegenerative disorder. A health care professional may diagnose a subject as having a neurodegenerative disorder upon presentation of a subject to a health care facility (e.g., a clinic or a hospital). In some instances, a health care professional may diagnose a subject as having a neurodegenerative disorder while the subject is admitted in an assisted care facility. Typically, a physician diagnoses a neurodegenerative disorder in a subject after the presentation of one or more symptoms.

The present invention also provides various kits for performing the methods of described herein. For example, kits comprising one or more primer and/or probe sets specific for the detection of target small non-coding RNA (e.g. miRNA). Such kits can further include primer and/or probe sets specific for the detection of control miRNA. Examples of primer or probe combinations in kits are include primers or probes specific for at least one miRNA selected from the group consisting SEQ ID NOs 1 to 79.

Such kits can be useful for direct miRNA detection in samples (e.g. bodily fluid such as blood, serum or plasma) isolated from patients, or can be used on purified RNA samples.

Throughout this specification, unless the context requires otherwise, the word "comprise" or variations such as "comprises" or "comprising", will be understood to imply the inclusion of a stated element or integer or method step or group of elements or integers or method steps but not the exclusion of any element or integer or method step or group of elements or integers or method steps.

EXAMPLES

Example 1: Materials and Methods

Participants

Participants were divided into three groups: healthy controls (HC), Parkinson's Disease newly diagnosed (PD-N) and Parkinson's disease (PD) based on the establish criteria from the UK PD Society Brain Bank Clinical Diagnostic Criteria and collected as part of The Australian Parkinson's Disease Registry (APDR). In the PD study, the sample size of 45 participants were analysed in this study. In the PD discovery set, serum from 45 patients (HC=18 and PD=27) were collected for deep sequencing and in the validation set, serum from 88 patients (HC, n=21 and PC, n=67). All individuals included in this study were assessed at the time of collection which includes phenotyping (examined and assessed for signs and severity of PD) and genotyping and full blood biochemistry pathology testing. Serum samples from HC (n=23) and those diagnosed with AD (n=23) were obtained from the Australian Imaging, Biomarkers and Lifestyle (AIBL) Study of Aging for the discovery study. In the validation study, an additional 310 serum samples were used for the study which comprised of AD (n=42), MCI (n=31) and HC (n=240). Diagnosis was based on the establish criteria from the National Institute of Neurological and Communicative Diseases and Stroke-Alzheimer's Disease and Related Disorders Association (NINCDA-ADRDA).

Blood samples were collected from all patients (fasting) from whole blood venepuncture into Sarstedt s-monovette serum-gel 7.5 ml tubes 01.1602.001 (Sarstedt, Germany). Samples were processed within two hours of collection and serum was snap frozen in liquid nitrogen.

Post-mortem tissues (HC, n=7, PD, n=8 and AD, n=7) were obtained from the Australian Brain Bank Network, together with accompanying histopathological data to select cognitively normal control cases. Samples of frontal cortex were dissected frozen, on a clean glass surface cooled with dry ice. Tissues were stored at −80° C. until required.

Exosome Enrichment from Post-Mortem Tissue.

Extracting exosomes from post-mortem brain tissue was performed using tissue from the frontal cortex (20 mg) was treated with 75 U/ml of collagenase type 3 in Hibernate-E (at a ratio of 800 μl per 100 mg of brain) and gently homogenized. The dissociated tissue was spun at 300×g for 5 minutes at 4° C., the pellet was collected (nominated as 'total brain') in PBS (with PI/PS), homogenised and stored at −80° C. for later use. The supernatant from the 300×g was transferred to a fresh tube, spun at 2000×g for 10 mins at 4° C., then the supernatant spun at 10,000×g for 30 mins at 4° C. The supernatant was overlaid on a triple sucrose cushion (0.6M, 1.3M, 2.5M). The gradient was spun for 3 hrs at 180,000×g (average) at 4° C. (SW41 Beckman, ultra-clear tubes with 13.2 ml capacity). Fractions 2 was subsequently collected and then diluted with ice cold PBS and spun at 100,000×g (average) at 4° C. (Ti 70.1 Beckman) for 1 hr to pellet the vesicles. Following spin completion the supernatant was discarded and pellet collected in ice cold PBS (with PI/PS).

Next Generation Sequencing and qRT-PCR

Exosomes isolated from post-mortem tissue was performed as described above. Serum exosomal RNA was isolated by using the Plasma/serum circulating and exosomal RNA isolation kit (Norgen Biotek, Canada) from 1 ml serum per participant whereby the manufactures' protocol was followed. The total exosomal RNA yield, composition and quality was analysed by the Agilent 2100 Bioanalyser using the Small RNA kit (Agilent). Total RNA yield from total brain tissue was analysed by the Agilent 2100 Bioanalyser using the RNA6000 kit (Agilent). Small RNA enriched from total brain samples and exosomal RNA was converted into cDNA libraries using the Ion Total RNA-Seq Kit V2 (Life Technologies, Australia) and prepared for sequencing. Pooled libraries with unique barcodes were loaded on Ion 540™ sequencing chips and run on the Ion Torrent Ion GeneStudio S5 (Life Technologies, Australia). The sequences are then assessed for quality and primer-adapter sequences are trimmed by the Torrent Suite software (version 5.8.0), followed by alignment to the human reference genome (HG19). The trimmed and aligned data was transferred to Partek Genomics Suite and mapped to known miRNA using miRBase V·20. Bioinformatics analysis and differential expression was performed using Partek Genomics Suite. The panel of candidate miRNA found highly associated with PD (including positive and negative controls) were used for validation on a new set of serum samples from ADPR. Serum samples for the validation study were spiked with synthetic *C. elegan* miR-39 (Qiagen) during exosomal RNA extraction to monitor extraction efficiency and for normalisation purposes. Upon processing of the serum samples as above, 1 ng of exosomal miRNA was converted to cDNA (TaqMan MicroRNA Reverse Transcription Kit, Applied Biosystems) according to the manufacturers' protocol with a primer pool containing 18 miRNA assays (TaqMan microRNA assays, 5×, Applied Biosystems). cDNA samples were pre-amplified (TaqMan PreAmp Master Mix Kit, Applied Biosystems) and qRT-PCR (TaqMan Fast Advanced Master Mix, Applied Biosystems) was performed using individual miRNA assays (TaqMan microRNA assays, 20×, Applied Biosystems) and run on the ViiA™ 7 Real-Time PCR System across a 384-well format. Reverse transcription and pre-amplification no template controls using primer pools and individual assays were also prepared to ensure there was no background amplification of miRNA assays. Raw data was uploaded to DataAssist (Applied Biosystems) to calculate delta Ct (ΔCt) and normalisation against controls further statistical analysis.

Statistical Analysis

To analyse the deep sequencing data, the number of reads of each miRNA were normalised to reads per million (RPM) across all samples. Low abundant miRNAs with less than 50 read counts across all samples were removed thus, high abundant miRNAs were analysed in this study. Initial statistical analysis of miRNA expression changes was performed using the Partek Genomics and statistical suite. Selection of miRNAs was based upon ANOVA analysis comparing healthy controls and PD group (Clinical classification at the time of collection). Probability values were adjusted for multiple testing using the False Discovery Rate (FDR) method of Benjamini and Hochberg (1995). Significant changes in miRNA expression were expressed in Fold Change [$Log_2$] and defined as p (PD Vs HC)≤0.05.

Example 2: Levels of Small Non-Coding miRNA in Serum are Associated with PD Disease State The characteristics of the APDR participants included in the study are shown in Table 1. Small RNA deep sequencing was performed on exosomal RNA samples isolated from each participant. Upon alignment to the human genome (HG10) and mapping to miRBase V.20, 1414 miRNA species were identified in the exosomal serum dataset. Reads per miRNA were then normalised to reads per million (RPM) and filtered for abundantly expressed miRNA displaying a mean greater than 20 RPM. The number of abundantly expressed miRNAs used for differential analysis was 194 miRNA species.

TABLE 1

Demographics and clinical make up of discovery and validation set

| | HC | PD |
|---|---|---|
| Discovery Set | | |
| N | 18 | 27 |
| Age (mean ± SD) | 67 ± 3.3 | 68 ± 9.8 |
| Gender (F/M/unknown) | 8/10 | 14/12/1 |
| SCOPA/COG (mean ± SD) | N/A | 25.5 ± 5.1 |
| H & R Score of 3 | N/A | 26 |
| H & R Score of 4 | N/A | 1 |
| Validation Set | | |
| N | 21 | 67 |
| Age (mean ± SD) | 66 ± 3.6 | 68 ± 5.4 |
| Gender (F/M) | Unknown | 28/39 |
| SCOPA/COG (mean ± SD) | N/A | 32 ± 5.1 |
| H & R Score of 0/1 | N/A | 1/24 |
| H & R Score of 2 | N/A | 31 |
| H & R Score of 3 | N/A | 11 |

Upon performing ANOVA analysis, 28 miRNA were found to be significantly deregulated (FDR (PD Vs HC)≤0.05 and ±2 fold change, Table 2); 21 miRNA were found to be downregulated (hsa-miR-122-5p, hsa-miR- 125b-5p, hsa-miR-133a-3p, hsa-miR-146b-5p, hsa-miR-181a-5p, hsa-miR-183-5p, hsa-miR-192-5p, hsa-miR-193a-5p, hsa-miR-208a-3p, hsa-miR-214-3p, hsa-miR-222-3p, hsa-miR-30a-5p, hsa-miR-31-5p, hsa-miR-34a-5p, hsa-miR-3529-3p, hsa-miR-375-3p, hsa-miR-378a-3p, hsa-miR-489-3p, hsa-miR-505-3p, hsa-miR-7-5p and hsa-miR-769-5p), and 7 miRNA (hsa-miR-1306-5p, hsa-miR-199a-5p, hsa-miR-26a-5p, hsa-miR-339-5p, hsa-miR-4433-3p hsa-miR-4433b-5p and hsa-miR-766-3p) were found to be upregulated (FIG. 1).

This data demonstrates that the level of expression of a miRNA in a serum sample comprising extracellular vesicles is indicative of a disease state. In particular, this data demonstrates that the level of expression of a miRNA in a serum sample comprising extracellular vesicles is indicative of a PD disease state

TABLE 2

Differentially expressed serum exosomal miRNA associated with PD

| miRNA | *p-value (PD vs. HC) | FoldChange (PD vs. HC) | Description |
|---|---|---|---|
| hsa-miR-193a-5p | 4.28E−10 | −6.59332 | PD down vs HC |
| hsa-miR-192-5p | 8.89E−09 | −3.3024 | PD down vs HC |
| hsa-miR-125b-5p | 1.21E−08 | −2.54355 | PD down vs HC |
| hsa-miR-122-5p | 2.59E−08 | −8.37259 | PD down vs HC |
| hsa-miR-34a-5p | 3.67E−08 | −6.67974 | PD down vs HC |
| hsa-miR-222-3p | 5.42E−08 | −2.3537 | PD down vs HC |
| hsa-miR-146b-5p | 7.15E−08 | −2.96012 | PD down vs HC |
| hsa-miR-199a-5p | 4.53E−07 | 2.56602 | PD up vs HC |
| hsa-miR-7-5p | 5.60E−07 | −5.96907 | PD down vs HC |
| hsa-miR-181a-5p | 6.08E−07 | −7.94225 | PD down vs HC |
| hsa-miR-31-5p | 1.32E−06 | −7.78136 | PD down vs HC |
| hsa-miR-133a-3p | 1.33E−06 | −6.77229 | PD down vs HC |
| hsa-miR-378a-3p | 1.95E−06 | −3.63491 | PD down vs HC |
| hsa-miR-489-3p | 2.21E−06 | −5.92894 | PD down vs HC |
| hsa-miR-183-5p | 2.43E−06 | −4.93803 | PD down vs HC |
| hsa-miR-375-3p | 2.55E−06 | −3.27774 | PD down vs HC |
| hsa-miR-505-3p | 4.76E−06 | −2.20998 | PD down vs HC |
| hsa-miR-3529-3p | 2.58E−05 | −2.49123 | PD down vs HC |
| hsa-miR-26a-5p | 2.71E−05 | 2.09203 | PD up vs HC |
| hsa-miR-208a-3p | 3.95E−05 | −5.92653 | PD down vs HC |
| hsa-miR-214-3p | 6.65E−05 | −2.3995 | PD down vs HC |
| hsa-miR-766-3p | 0.00011644 | 2.21299 | PD up vs HC |
| hsa-miR-339-5p | 0.000198507 | 2.09287 | PD up vs HC |
| hsa-miR-4433-3p | 0.000238609 | 2.95967 | PD up vs HC |
| hsa-miR-4433b-5p | 0.000238609 | 2.95967 | PD up vs HC |
| hsa-miR-769-5p | 0.000261912 | −2.10039 | PD down vs HC |
| hsa-miR-30a-5p | 0.000346815 | −2.17136 | PD down vs HC |
| hsa-miR-1306-5p | 0.00090965 | 2.15269 | PD up vs HC |

*HC, n = 18 and PD, n = 27.

Figure 2:
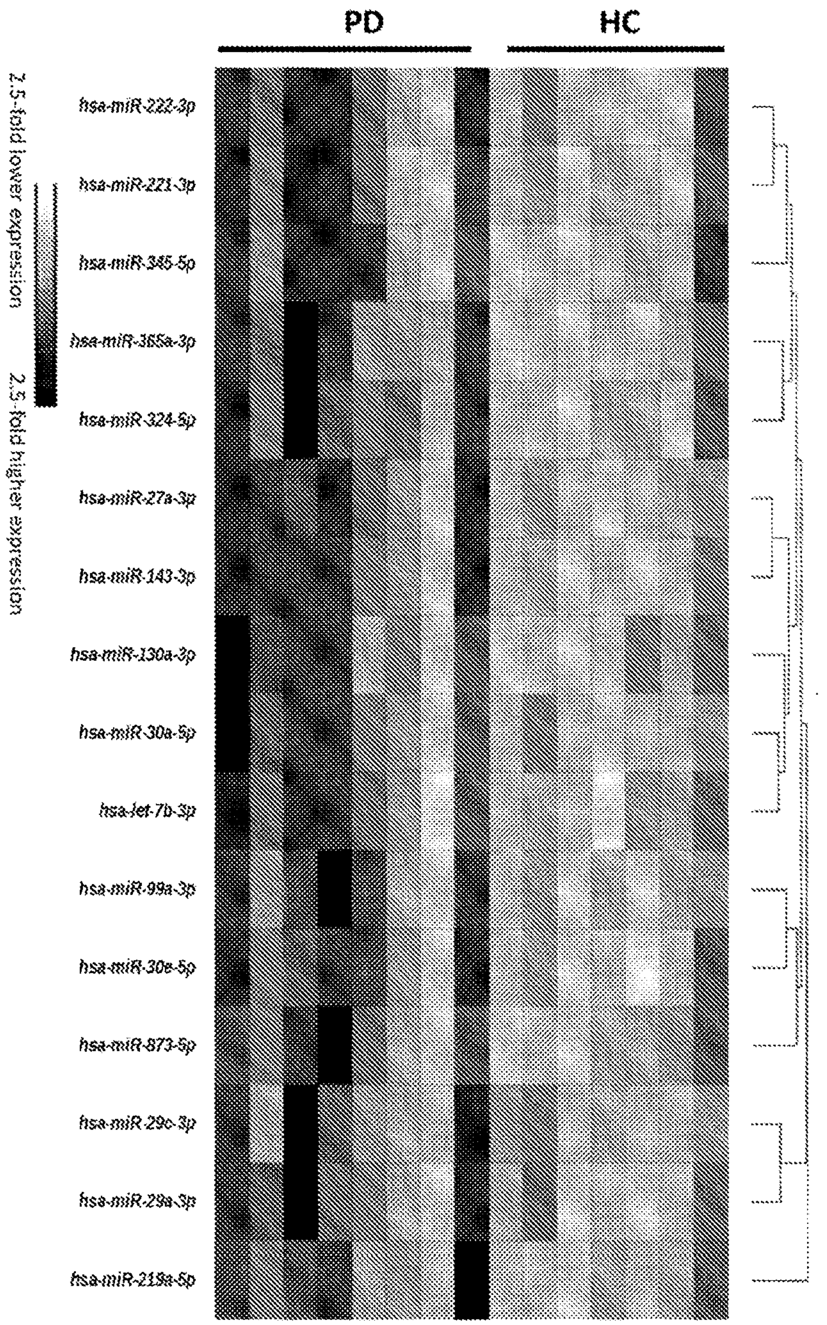
FIG. 2: Hierarchical clustering of differentially expressed brain derived exosomal miRNA biomarkers obtained from post-mortem tissue of controls and Parkinson's disease subjects Hierarchical clustering was performed using Partek Genomics Suite on significantly differentially expressed miRNA found in brain derived exosomes (BDEs) using Euclidean average linkage by miRNA. 16 miRNA were found to be significantly deregulated (FDR (PD Vs HC)≤0.05 and ±2 fold change). The darker the shade of grey, the higher the expression of miRNA compared to HC. Patient samples were arranged by attribute (HC, n=7 and PD, n=8).

Example 3: Levels of Small Non-Coding miRNA in Brain Tissue Derived Exosomes are Associated with PD Disease State To determine whether the same deregulated miRNA detected in serum were also deregulated in exosomes from the brains of PD participants we isolated BDEs from post-mortem tissues of PD subjects and compared them to control tissue. The isolation of exosomes from brain tissues was performed as previously published and met the criteria established by the International Society of Extracellular Vesicles (ISEV) to ensure vesicles isolated were bona fide exosomes. Methods to characterise the vesicles included electron microscopy, nanoparticle tracking analysis and western immunoblotting of known exosomal markers and non-exosomal markers. Upon the successful characterisation of exosomes, small RNA content was profiled using next generation sequencing to identify deregulated exosomal miRNA from the post-mortem brain tissue of PD subjects. The number of abundantly expressed miRNAs used for differential analysis was 186 miRNA species from a total of 1663 detected in the entire BDE dataset. Upon performing ANOVA analysis with only the abundant miRNA species, 16 miRNA were found to be significantly deregulated (FDR (PD Vs HC)≤0·05 and ±2 fold change, Table 3) and were all found to be upregulated (FIG. 2).

TABLE 3

Differentially expressed brain derived exosomal miRNA associated with PD

| miRNA | *p-value (PD vs. HC) | FoldChange (PD vs. HC) | Description |
|---|---|---|---|
| hsa-miR-324-5p | 0.00655653 | 2.12116 | PD up vs HC |
| hsa-miR-99a-3p | 0.0112962 | 2.60611 | PD up vs HC |
| hsa-miR-221-3p | 0.0156257 | 2.11946 | PD up vs HC |
| hsa-miR-30e-5p | 0.0176049 | 2.08991 | PD up vs HC |
| hsa-miR-30a-5p | 0.0183781 | 2.07795 | PD up vs HC |
| hsa-miR-365a-3p | 0.0212105 | 2.80859 | PD up vs HC |
| hsa-miR-143-3p | 0.0233312 | 2.91266 | PD up vs HC |
| hsa-miR-222-3p | 0.0276742 | 2.10266 | PD up vs HC |
| hsa-miR-27a-3p | 0.0369641 | 2.51501 | PD up vs HC |
| hsa-miR-29a-3p | 0.0372948 | 2.10918 | PD up vs HC |
| hsa-miR-219a-5p | 0.0373524 | 2.90085 | PD up vs HC |
| hsa-miR-29c-3p | 0.0399738 | 2.30083 | PD up vs HC |
| hsa-miR-130a-3p | 0.0406251 | 2.16827 | PD up vs HC |
| hsa-let-7b-3p | 0.0438451 | 2.01344 | PD up vs HC |
| hsa-miR-345-5p | 0.0458726 | 2.46496 | PD up vs HC |
| hsa-miR-873-5p | 0.0467742 | 2.49959 | PD up vs HC |

*HC, n = 7 and PD, n = 8.

This data demonstrates that the level of expression of a miRNA in a brain sample comprising extracellular vesicles is indicative of a disease state.

Figure 3:
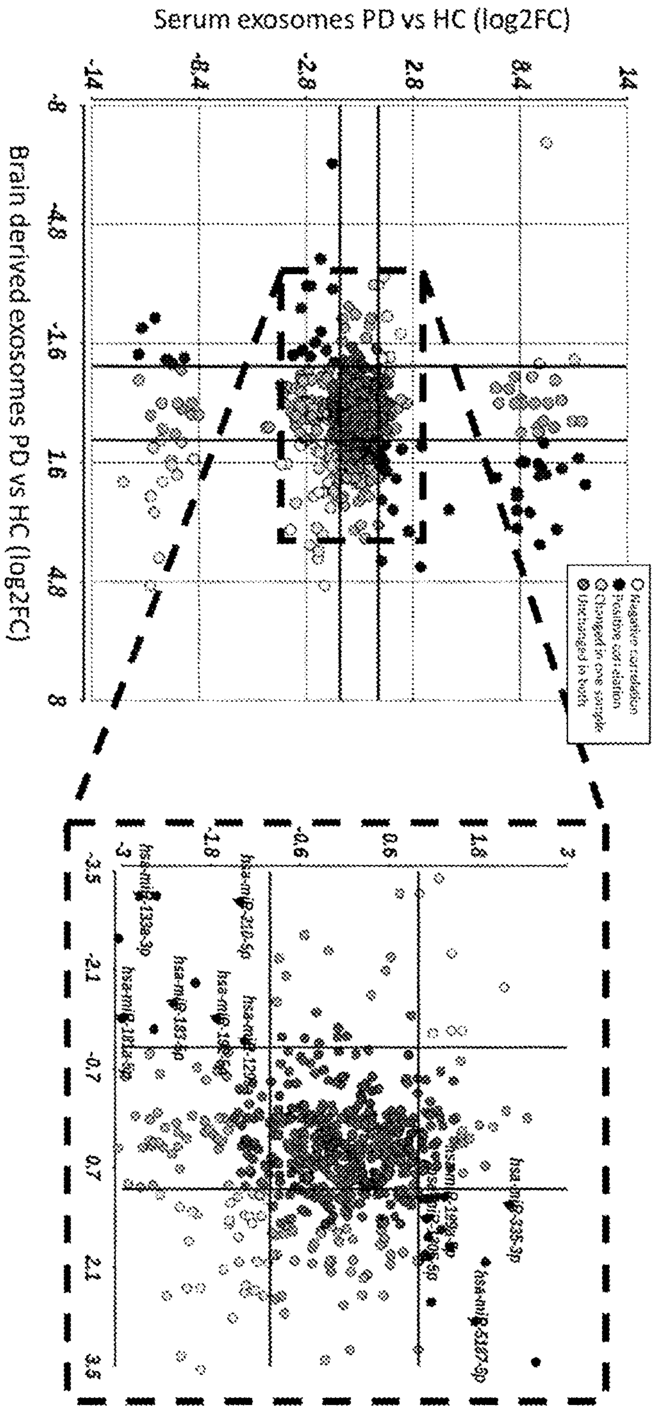
FIG. 3: Direction of global miRNA changes in brain derived exosomes and serum exosomes of PD samples compared to controls. ANOVA analysis was performed on the normalised reads from both small RNA datasets (BDE's and serum exosomes) and were plotted as Log 2 fold change. The insert in the figure outlined by the dashed border focuses on miRNAs of interest which are labelled. miRNA found to display a negative correlation in expression within serum exosomes and brain derived exosomes (BDEs) are indicated by white datapoints. Those found to display the same direction (positive correlation) in expression (either upregulated or downregulated) in both sample types are indicated by the black datapoints. miRNA found unchanged in both sample types are indicated in dark grey and those changed in one sample type are indicated in light grey. Serum exosomes, HC, n=18 and PD, n=27. BDEs, HC, n=7 and PD, n=8.

Example 4: Association of Levels of Small Non-Coding miRNA in Brain Tissue Derived Exosomes Associated with PD Disease State and Levels of Small Non-Coding miRNA in Serum Associated with PD Disease State Two of the 28 miRNAs (hsa-miR-222-3p and hsa-miR-30a-5p) were found to be significantly differentially expressed (FDR (PD Vs HC) 0·05 and ±2-fold change) in exosomal serum isolated from PD participants and BDE's from PD subjects compared to controls. The remaining 26 exosomal miRNAs significantly deregulated in serum samples were also found differentially expressed in BDEs of PD subjects, although they did not show significant changes. Interestingly, the two miRNAs significantly deregulated in both sample types, hsa-miR-222-3p and hsa-miR-30a-5p, were found to display opposite whereby they were down-regulated in the serum of PD participants while they were upregulated in BDEs of PD subjects. The inverse expression between the two sample types led to the question on whether the same trend existed for all miRNAs. To visualise the direction of expression between the two sample types, the fold changes between PD V's HC observed in BDEs and serum exosomes were plotted in FIG. 3. While many miRNAs (503) were found to display unchanged expression in both BDEs and serum exosomes of PD samples compared to controls, other miRNAs were found to be changed in only one sample type (659 in serum and 125 in BDEs) and not the other. There were 66 miRNAs that displayed an inverse expression (negative correlation) between the two sample types including the significantly (FDR (PD Vs HC)≤0.05 and ±2-fold change, mean >20 RPM) deregulated hsa-miR-222-3p and hsa-miR-30a-5p in PD samples (FIG. 3 insert). There were 20 miRNAs that were found to be downregulated in both serum exosomes and BDEs including 5 that were significantly deregulated in serum exosomes (hsa-miR-181a-5p, hsa-miR-183-5p, hsa-miR-192-5p, hsa-miR-489-3p and hsa-miR-133a-3p, FIG. 3) however, insignificantly downregulated in BDEs. Those found to be significantly upregulated in serum would make for an ideal blood biomarker as they can be easily, and reproducibility detected by targeted qRT-PCR. From FIG. 3, 41 miRNAs were found to be upregulated in both serum exosomes and BDEs however, only 2 of these were found to be significantly upregulated in serum exosomes while the remaining were insignificant.

Figure 4:
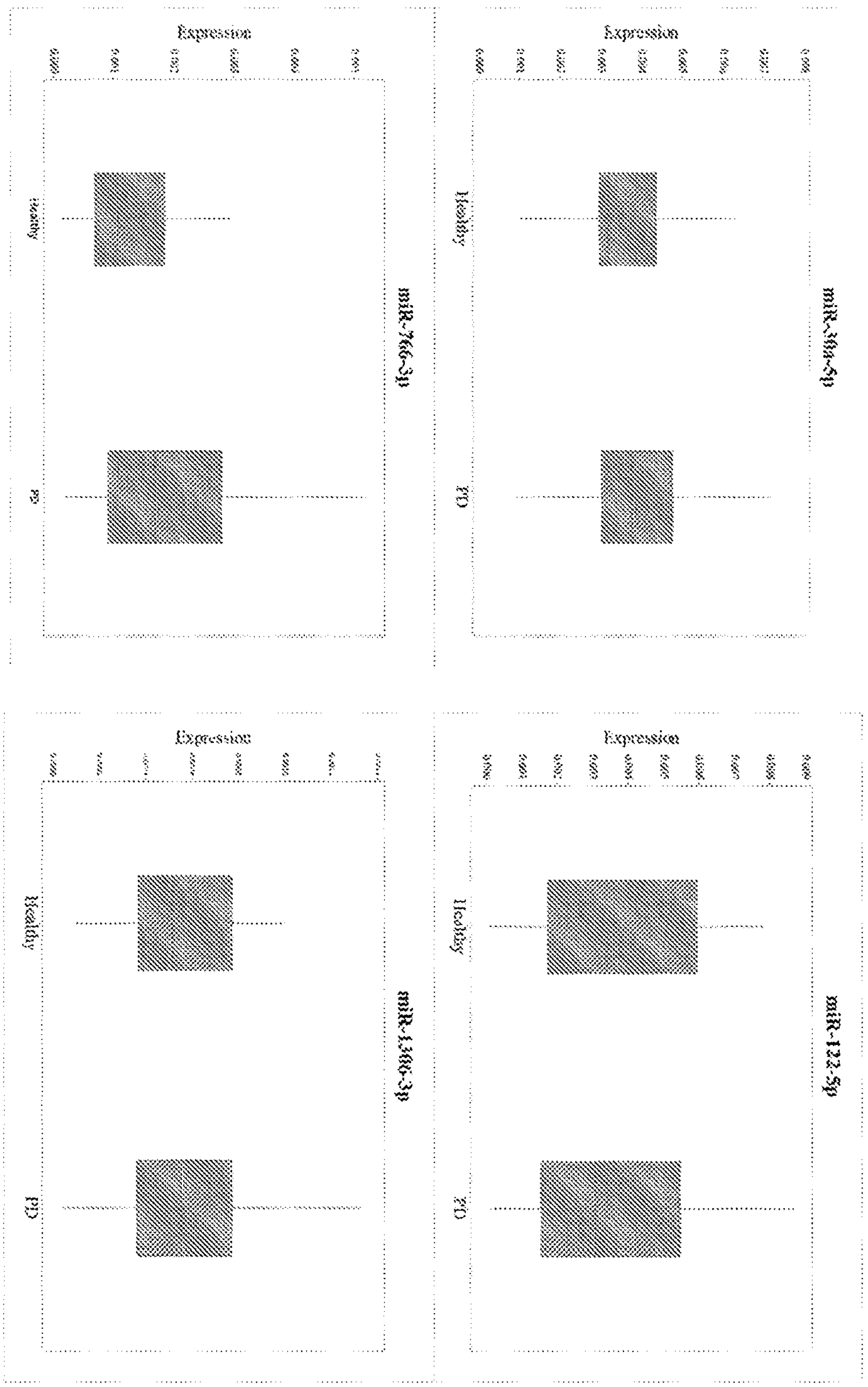
FIG. 4: Box plots showing validated serum exosomal miRNA differentially expressed in subjects with Parkinson's disease compared to healthy controls. The strongest miRNAs identified to be associated with Parkinson's disease. $2^{\wedge-deltaCT}$ plotted between HC and PD participants. HC, n=21 and PD, n=67.

Example 5: Validation of Methods of Diagnosing a PD Using Levels of Small Non-Coding miRNA in Serum Associated with PD Disease State miRNA found significantly deregulated in serum exosomes and any trend of change in BDEs (white or black dots in FIG. 3) were chosen for the blood-based validation study. This included hsa-miR-1306-5p, hsa-miR-199a-5p, hsa-miR-181a-50, hsa-miR-133a-3p, hsa-miR-489-3p, hsa-miR-183-5p, hsa-miR-192-5p, hsa-miR-222-3p and hsa-miR-30a-50 (Table 3). Other potential candidates were chosen from Table 2 including miRNAs that were significantly upregulated in serum exosomes (hsa-miR-4433-3p, hsa-miR-766-3p-hsa-miR-339 and hsa-miR-26a-5p) followed by the top most downregulated miRNAs in Table 2 (hsa-miR-122-5p, hsa-miR-31-5p, hsa-miR-34a-5p, hsa-miR-193a-5p, hsa-miR-7-5p, hsa-miR-208a-3p and hsa-miR-378-a-3p) to make a panel of 20 miRNAs to screen in a validation screen using qRT-PCR comprising of new participants (Table 1, validation set). Upon the completion of the qRT-PCR assay, miRNA expression values (Delta Cts) were applied to several machine learning models and it was found that 'Discriminant Analysis—Linear' was the model that provided the highest accuracy. The most important feature miRNAs that provided the correct classification were hsa-miR-1306-5p, hsa-miR-122-5p, hsa-miR-30a-5p and hsa-miR-766-3p (FIG. 4) with a sensitivity of 71.6% and a specificity of 76.2% with an AUC of 0.727 (64 correct predictions of the 88 samples in the validation set). To further improve specificity and sensitivity, age is added as a feature, and subgroups that contain certain features to assist in classification of HC and PD are added. Association Rule Mining is applied to determine additional features in this dataset to further improve prediction.

Example 6: Materials and Methods for Examination of CJD

Prion-Infected Mouse Model

All animals used in this study were approved by the University of Melbourne Animal Experimentation Ethics Committee (ID: 1111949). The M1000 prion strain used in the prion study is derived from the Fukuoka-1 strain of mouse-adapted human prions, which was derived from a patient who died from Gerstmann-Sträussler-Scheinker, a familial form of prion disease. Mice were intracerebrally inoculated with this prion strain that resulted in the peripheral accumulation of $PrP^{Sc}$. A 10% (w/v) infectious brain homogenate was prepared in Phosphate Buffered Saline (PBS; 123 mM NaCl, 10 mM $Na_2HPO_4$, 3 mM $KH_2PO_4$, pH 7.2) from a pool of BalbC mice culled at the terminal stage of disease, containing ~$10^9$ infectious dose units per gram of tissue. This was followed by sonicating the homogenate on ice for 1 min and diluted a further $10^{-4}$ in PBS before injecting 30 μL into the left parietal region of 6-8 weeks of age BalbC mice (Animal Resources Centre, Western Australia) under methoxyflurane inhalation anaesthesia. Sham mice (control group of mice) were inoculated with 30 μL of PBS in the left parietal region. Mice were given food and water ad libitum with all handling according to prescribed national guidelines and were observed daily for signs of disease. Animals were sacrificed under methoxyflurane anaesthesia and euthanised at predetermined time points (3, 6, 10, 13 and 17 wpi) or when persistent signs consistent with terminal prion disease were evident, such as bradykinesis, weight loss, kyphosis, hind limb paresis and ataxia. Brains were removed from sham or M1000 mice (n=4-5) at each time point and dissected into half along the midline of the brain. Each hem i-brain was flash-frozen in liquid nitrogen and stored at −80° C. until processing for western immunoblotting. For RNA procedure, the hem i-brain was placed in 700 μL of RNAlater (Life Technologies, Melbourne, VIC, Australia) to preserve RNA for isolation. The samples were kept at 4° C. for 24 hr before transfer for storage at −80° C. until use.

Human Clinical Samples

All serum samples were collected by the Clinical Dementia Centre Gottingen Patients with CJD (n=26) were diagnosed according to established criteria and non-dementia (ND, n=20) samples were used as controls, including an additional group of samples for validation (CJD, n=20 and ND, n=6). Each subject had undergone molecular genotyping to determine codon 129 subtyping (MM, MV or VV). Once collected, samples were stored at −80° C. until further use. Serum exosomal RNA was isolated by using the Plasma/serum circulating and exosomal RNA isolation kit (Norgen Biotek, Canada) from 1 ml serum per participant whereby the manufactures' protocol was followed. A spike-in of cel-miR-39 (2.5 μl of 5 nmol) was introduced during the RNA isolation to serve as an external miRNA control during qRT-PCR. The yield of exosomal RNA was analysed by a small RNA assay and ran on the Agilent 2100 Bioanalyser (Agilent) before conversion to cDNA for qRT-PCR.

Total RNA Extraction and Small RNA Sequencing

Total RNA (including small RNA) was isolated from brain tissue and exosomes using miRNeasy (Qiagen, Melbourne, VIC, Australia) according to the manufacturer's instructions. The extracted RNA was evaluated using an Agilent 2100 Bioanalyser (Agilent Technologies, Palo Alto, CA, USA) and the RNA6000 and small RNA assays. For each small RNA library, RNA was ligated to adapters containing a unique index barcode provided by the Ion Xpress™ RNA-Seq Barcode 1-16 Kit (Life Technologies) to allow libraries to be pooled during sequencing. All libraries were constructed according to manufacturer's protocol (Ion Total RNA-seq kit v2, Life Technologies). Briefly, RNA was reverse transcribed to cDNA using adaptor specific primers. Using the Magnetic Bead Purification Module provided by the Ion Total RNA-seq kit v2 (Life Technologies), samples containing cDNA were size-selected from 94 to 130 nt (including the length of small RNA insert and adaptors). Library amplification was then performed using PCR and followed by a library clean-up step using Nucleic Acid Binding Beads (Life Technologies). The quality and quantity of constructed library were determined by Agilent 2100 Bioanalyser using High-sensitivity DNA Chip (Agilent Technologies). Equally pooled libraries were clonally amplified onto Ion Sphere™ Particles (ISPs) supplied by the Ion OneTouch™ 200 Template Kit v2 DL Kit (Life Technologies). The ISP templates were produced by using OneTouch™ 2 Instrument and enrichment system (Life Technologies). Pooled libraries with unique barcodes (three barcoded libraries processed per chip) were sequenced on the Ion Torrent PGM™ (Life Technologies) using Ion™ 318 Chips (Life Technologies) and the Ion PGM™ 200 Sequencing Kit (Life Technologies).

Quantitative RT-PCR

RNA isolated from samples was converted to cDNA using the miRNA Reverse Transcriptase Kit (Applied Biosystems) and individual TaqMan miRNA assays (Applied Biosystems, Mulgrave, VIC, Australia) were used for qRT-PCR according to the manufacturers' protocol. Assays were run on a ViiA™ 7 Real-Time PCR System (Life Technologies) using the manufacturer's recommended cycling conditions. All data was saved and analysed with hsa-miR-185-5p, hsa-miR-451a and hsa-miR-93-5p as endogenous controls (identified to be consistently expressed across human serum exosomal samples by NGS) using the ViiA 7 software v1.2.2 (Life Technologies).

Small RNA Sequence Data Analysis

Raw sequences were subjected to pre-processing and sequence alignment using the default parameters provided by Torrent Suite™ v4.0 software (Life Technologies). Within the Torrent Suite™, high quality reads were parsed for whole genome sequence mapping. The reads were mapped to *Mus musculus* v10 (mm10) build of the mouse genome from University of California Santa Cruz database using Torrent Mapping Alignment Program (TMAP) with their default parameters. Aligned reads were attained for small RNA expression analysis using Partek Genomic Suite. A number of 1401 miRNAs were identified in the dataset across all timepoints. Reads were normalised to read per million (RPM) and only abundant miRNA species (mean >10 RPM across all thalamus samples serum exosome samples) were used for downstream analysis such as differential expression and Gene (GO) Ontology analysis. The Database for Annotation, Visualisation and Integrated Discovery (DAVID) v6.7 and MetaCore® software (GeneGo, Inc., Encinitas, CA, USA) were used to investigate Gene Ontology (GO) biological processes, molecular functions and localisations of the corresponding gene of interest. The pathways were classified using the Kyoto Encyclopedia of Genes and Genomes (KEGG) database by their hierarchy schema according to the major functions of genes. The pathways and their corresponding genes were visualised using Cytoscape v3.0.2 to illustrate the impact of the genes of interest in this study. For identifying the KEGG pathway of mRNAs that were targeted by miRNAs, miRTarBase and TarBase algorithm in DNA intelligent analysis (DIANA) miRPath v2.0 were used. The miRNA pathway analysis was performed using the default parameters in DIANA miRPath and miRTarBase according to developer's recommendations. Circos is a Perl-based software package for visualizing large-scale multi-sample genomic information in circular ideogram. Circos v0.64 was selected to display positional relationships between data track intervals.

Biostatistical Analysis

Biostatistical analysis was performed with R software and the package glmnet was used to analyse Delta Ct values obtained from the qRT-PCR validation of human clinical samples. The LASSO (least absolute shrinkage and selection operator) model was trained on the 40 participants collected to select optimal weighting coefficients via penalised maximum likelihood to build a diagnostic miRNA signature. The cross-validation performance of the LASSO models were tested in 20-fold experiments. The regression analysis performed both variable selection and regularization in order to enhance the prediction accuracy and interpretability of the statistical model. AUC was employed to demonstrate the sensitivity and specificity of the 3 strongest miRNAs in predicting diagnosis.

Figure 5:
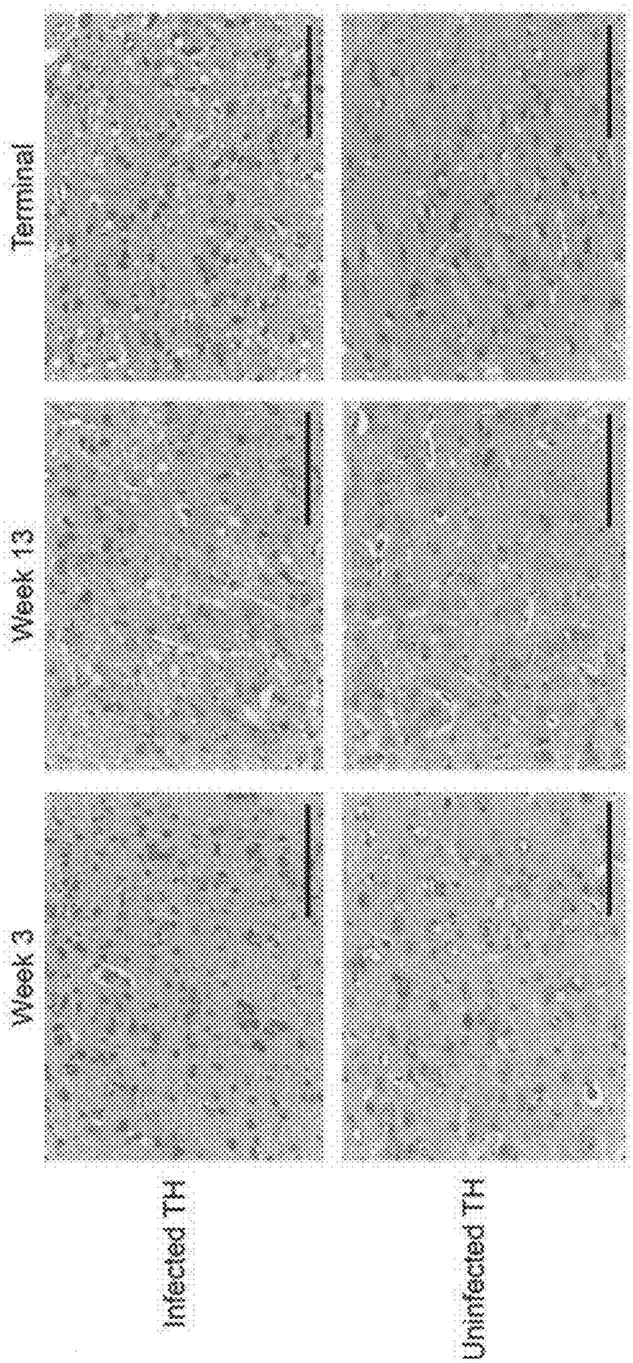
FIG. 5: Pathology associated with prion-infected mice. Histology was performed using haematoxylin and eosin staining on thalamus brain sections of (infected and prion-infected mice prepared at the indicated time points or when the mice manifested with clinical symptoms of prion disease (terminal stage). Images are taken at ×40 magnification. Scale bars shown are 100 μm.
Figure 6:
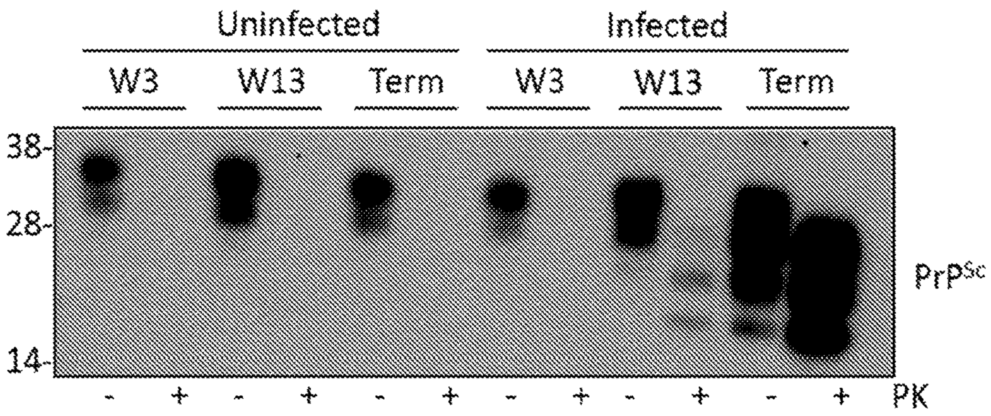
FIG. 6: The detection of $PrP^{Sc}$ by Western blotting. Western blotting analysis was performed on thalamus brain sections of uninfected and prion-infected mice treated with proteinase K (PK). Representative images of n=4-5 per group.

Example 7: Levels of Small Non-Coding miRNA in Brain Tissue are Associated with Prion Disease State and Prion Disease Stage A previously established in vivo model of prion disease with M1000 strain was employed in this study. Here, the progression of neuropathological changes was assessed over the time-course starting from 3 weeks wpi to the end-stage of disease. The immunochemistry images of the thalamus region from control (uninfected) and prion-infected mice were shown in FIG. 5. Consistent with the results from Brazier et al., spongiform change was first observed in the thalamus of prion-infected mice at week 13 after inoculation. At the terminal stage, the spongiform change in the thalamus progressed to severe vacuolation and was reported previously that this brain region showed prominent plaque deposition. Analysis by western immunoblot showed the presence of prion protein (PrP) by week 3 post-inoculation with the $PrP^{Sc}$ abundance increasing thereafter at terminal stage (FIG. 6).

Figure 7:
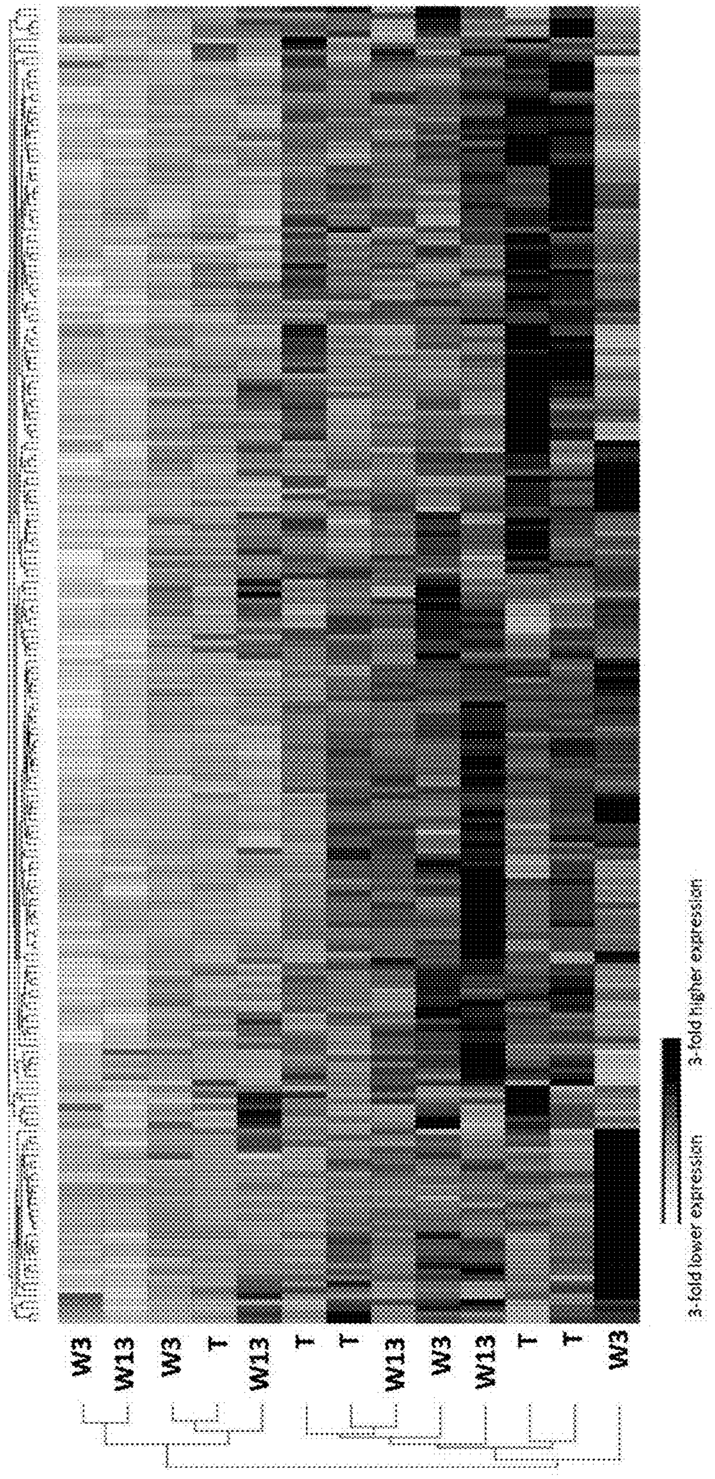
FIG. 7: Expression of miRNA detected in the thalamus of prion M1000 infected and uninfected mice at week 3, 13 and terminal stage. B) Hierarchical clustering of abundantly expressed miRNA (min >10 reads per million (RPM) across in all samples) in prion M1000 infected mice at week 3, 13 and terminal stage. The darker the shade of grey, the higher the expression of miRNA compared to uninfected.

After confirming thalamic neurons undergo neuropathological changes in the brain using immunohistochemistry, several analytical methods were used to assess miRNA expression patterns across 3 timepoints which include 3, 13 and terminal wpi. Abundantly expressed miRNA with greater than 10 RPM across all samples, a total of 82 miRNAs, was visualised in a heat map to observe global miRNA changes across prion M1000 mice (FIG. 7, Table 4).

TABLE 4

| Most abundant miRNAs found in the thalamus<br>Abundantly expressed miRNA in the thalamus |
|---|
| mmu-let-7a-5p |
| mmu-let-7b-5p |
| mmu-let-7c-5p |
| mmu-let-7d-5p |
| mmu-let-7e-5p |
| mmu-let-7g-5p |
| mmu-let-7i-5p |
| mmu-miR-100-5p |
| mmu-miR-103-3p |
| mmu-miR-107-3p |
| mmu-miR-124-3p |
| mmu-miR-125a-5p |
| mmu-miR-125b-5p |
| mmu-miR-126a-3p |
| mmu-miR-126a-5p |
| mmu-miR-127-3p |
| mmu-miR-128-3p |
| mmu-miR-129-2-3p |
| mmu-miR-132-3p |
| mmu-miR-134-5p |
| mmu-miR-135a-5p |
| mmu-miR-136-5p |
| mmu-miR-138-5p |
| mmu-miR-139-5p |
| mmu-miR-143-3p |
| mmu-miR-145a-5p |
| mmu-miR-149-5p |
| mmu-miR-150-5p |
| mmu-miR-151-5p |
| mmu-miR-16-5p |
| mmu-miR-181a-5p |
| mmu-miR-181b-5p |
| mmu-miR-185-5p |

TABLE 4-continued

| Most abundant miRNAs found in the thalamus Abundantly expressed miRNA in the thalamus |
|---|
| mmu-miR-191-5p |
| mmu-miR-204-5p |
| mmu-miR-218-5p |
| mmu-miR-219a-2-3p |
| mmu-miR-21a-5p |
| mmu-miR-23a-3p |
| mmu-miR-23b-3p |
| mmu-miR-24-3p |
| mmu-miR-26a-5p |
| mmu-miR-27a-3p |
| mmu-miR-27b-3p |
| mmu-miR-29a-3p |
| mmu-miR-29b-3p |
| mmu-miR-29c-3p |
| mmu-miR-30a-5p |
| mmu-miR-30b-5p |
| mmu-miR-30c-5p |
| mmu-miR-30c-5p |
| mmu-miR-30d-5p |
| mmu-miR-324-5p |
| mmu-miR-326-3p |
| mmu-miR-328-3p |
| mmu-miR-330-3p |
| mmu-miR-335-5p |
| mmu-miR-338-3p |
| mmu-miR-338-5p |
| mmu-miR-342-3p |
| mmu-miR-34a-5p |
| mmu-miR-376a-3p |
| mmu-miR-376b-3p |
| mmu-miR-378a-3p |
| mmu-miR-379-5p |
| mmu-miR-382-5p |
| mmu-miR-384-5p |
| mmu-miR-434-3p |
| mmu-miR-434-5p |
| mmu-miR-451a |
| mmu-miR-484 |
| mmu-miR-495-3p |
| mmu-miR-541-5p |
| mmu-miR-652-3p |
| mmu-miR-667-3p |
| mmu-miR-671-5p |
| mmu-miR-708-5p |
| mmu-miR-744-5p |
| mmu-miR-9-3p |
| mmu-miR-9-5p |
| mmu-miR-99a-5p |
| mmu-miR-99b-5p |

* Minimum reads all samples >100 RPM

Figure 8:
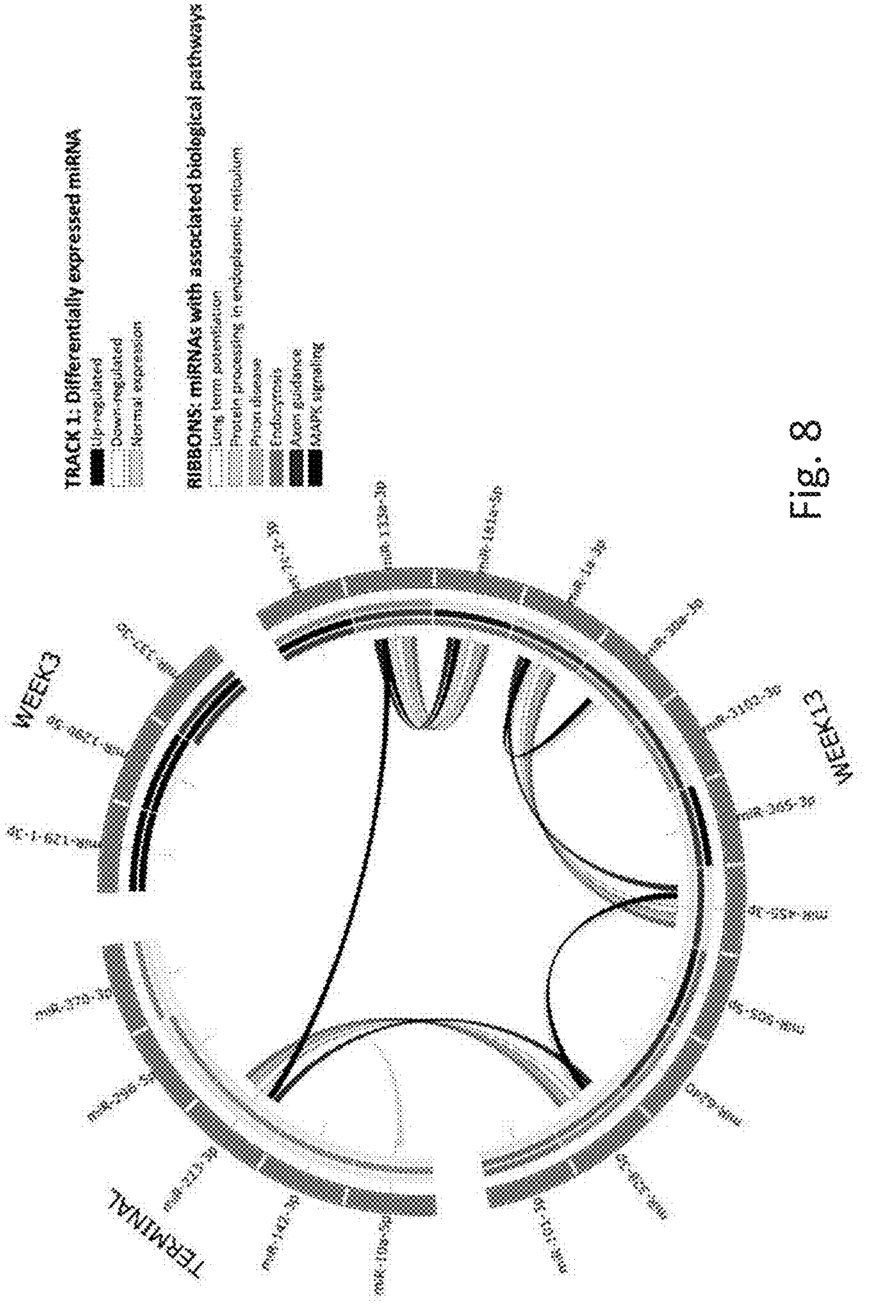
FIG. 8: Circos plot depicting the significant differentially expressed miRNAs in the thalamus. Statistically significant miRNA (P<0.01, fold change −2 and 2) were identified in prion M1000 mice compared to uninfected mice. The outermost track shows miRNAs that are significantly differentially expressed in week 3, week 13 and terminal stage of disease. The inner tracks illustrate expression heat map across all miRNAs in the time-course study. The expression levels are represented in log 2 fold change. The darker the shade of grey/black, the higher the expression of miRNA compared to uninfected. The ribbons inside the circos plot represent biological pathways the miRNA is involved in including long term potentiation, prion diseases, MAPK (mitogen-activated protein kinase) signalling, protein processing in endoplasmic reticulum, endocytosis and axon guidance. Prion M1000 week 3 (n=4), week 13 (n=4) and terminal (n=5). Prion uninfected week 3 (n=5), week 13 (n=5) and terminal (n=5).

FIG. 7 shows that the expression level of these abundantly expressed miRNAs were different among samples across the time course. Various miRNAs are consistently expressed and change in all samples within time points. Statistically significant differentially expressed (DE) miRNA (mean >10 RPM across all thalamus samples, p-value <0.05, fold change <−1.5 and >1.5) at each time point (Table 5) were identified and represented in a circos plot (FIG. 8).

TABLE 5

Differentially expressed miRNA identified in them thalamus

| | | Week 3 preclinical stage Thalamus | | Week 13 pre-clinical stage Thalamus | | Terminal stage Thalamus | |
|---|---|---|---|---|---|---|---|
| Biomarker | Time point | p-value | FC* | p-value | FC* | p-value | FC* |
| mmu-miR-129-1-3p | W3 | **0.00186592** | **−6.05479** | 0.836759 | 1.21333 | 0.283836 | −2.01164 |
| mmu-miR-129b-5p | W3 | **0.00100516** | **−2.62686** | 0.664837 | 1.17964 | 0.732312 | −1.13505 |
| mmu-miR-337-3p | W3 | **0.0459807** | **1.93411** | 0.545386 | 1.23682 | 0.618055 | −1.1515 |
| mmu-let-7c-2-3p | W13 | 0.834378 | 1.08133 | **0.0394445** | **2.27756** | 0.756139 | −1.07419 |
| mmu-miR-133a-3p | W13 | 0.819566 | 1.12466 | **0.0351433** | **1.9848** | 0.165813 | −1.46817 |
| mmu-miR-181a-5p | W13 | 0.860873 | −1.04241 | **0.0401921** | **1.62435** | 0.568114 | −1.09513 |
| mmu-miR-1a-3p | W13 | 0.987852 | −1.00663 | **0.0360615** | **1.99904** | 0.075089 | −1.48795 |
| mmu-miR-30a-3p | W13 | 0.871893 | −1.05271 | **0.0230981** | **1.98994** | 0.41294 | −1.17071 |
| mmu-miR-3102-3p | W13 | 0.713974 | −1.07177 | **0.0428382** | **1.52264** | 0.268337 | 1.17238 |
| mmu-miR-365-3p | W13 | 0.185391 | 2.36191 | **0.049061** | **2.4518** | 0.995738 | −1.00142 |
| mmu-miR-455-3p | W13 | 0.806189 | −1.08239 | **0.0114005** | **2.48201** | 0.160263 | 1.29164 |
| mmu-miR-505-5p | W13 | 0.0714303 | 1.39545 | **0.036753** | **1.65756** | 0.693389 | 1.06773 |
| mmu-miR-6240 | W13 | 0.597216 | 1.2031 | **0.046904** | **1.98721** | 0.470447 | 1.29224 |
| mmu-miR-328-3p | W13/T | 0.77288 | 1.06029 | **0.00409319** | **1.8754** | 0.022016 | 1.34896 |
| mmu-miR-101-3p | W13/T | 0.381466 | 1.2964 | **0.494949** | **1.63994** | **0.0143** | **−1.53758** |
| mmu-miR-10a-5p | T | 0.260386 | −2.10311 | 0.103402 | 1.87299 | **0.026127** | **−1.75153** |
| mmu-miR-142-3p | T | 0.931816 | −1.04862 | 0.661625 | 1.2986 | **0.001175** | **2.48518** |
| mmu-miR-223-3p | T | 0.772433 | −1.14881 | 0.915772 | −1.04597 | **0.028097** | **1.71737** |
| mmu-miR-296-5p | T | 0.62607 | −1.37237 | 0.117833 | 2.16411 | **0.015471** | **2.46612** |
| mmu-miR-370-3p | T | 0.681218 | 1.14312 | 0.613993 | 1.22356 | **0.013459** | **1.85792** |

Figure 9:
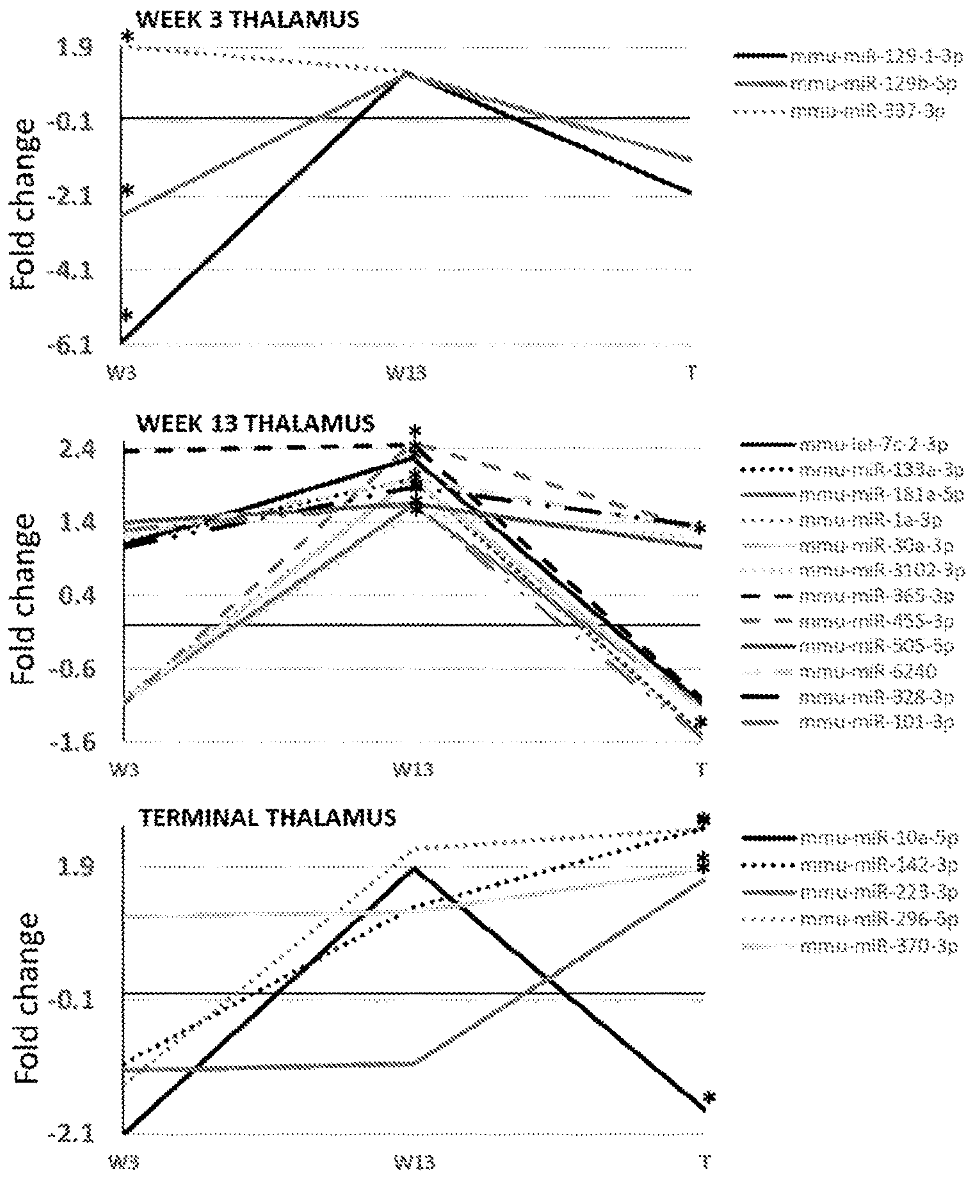
FIG. 9: Longitudinal analysis of the differentially expressed (DE) miRNAs across week 3, 13 and terminal stage in the thalamus of prion M1000 infected mice. Statistically significant miRNA (P<0.01, fold change −2 and 2) were identified in prion M1000 mice compared to uninfected mice at each time point and graphed here to display the longitudinal expression change of miRNA. * indicates the time-point which the miRNA was found to be significantly DE (ANOVA p-value <0.05). Prion M1000 infected; week 3 (n=4), week 13 (n=4) and terminal (n=5). Uninfected; week 3 (n=5), week 13 (n=5) and terminal (n=5).

*Prion infected (M1000) Vs control (uninfected), bold values are significant at time point The result from FIG. 8 highlighted a total of 20 miRNAs (p-value <0.05, fold change <−1.5 and >1.5) that were differentially expressed in this time-course study; including three miRNAs (mmu-miR-129-1-3p, mmu-miR-129b-5p, mmu-miR-337-3p) that were identified at 3 wpi, 12 miRNAs (mmu-let-7c-2-3p, mmu-miR-133a-3p, mmu-miR-181a-5p, mmu-miR-1a-3p, mmu-miR-30a-3p, mmu-miR-3102-3p, mmu-miR-365-3p, mmu-miR-455-3p, mmu-miR-505-5p, mmu-miR-6240, mmu-miR-328-3p and mmu-miR-101-3p) at 13 wpi, and 6 miRNAs were identified in the terminal stage (mmu-miR-101-3p, mmu-miR-10a-5p, mmu-miR-142-3p, mmu-miR-223-3p, mmu-miR-296-5p and mmu-miR-370-3p) where mmu-miR-101-3p was found to be significantly differently regulated at both 13 wpi and terminal stage. Longitudinal expression changes of these differentially expressed miRNAs across the time points collected can be observed in FIG. 9. The majority of miRNAs show dynamic expression changes during the progression of infection and the most significant changes are at 13 wpi at which point pathology changes are observed (FIGS. 5 and 6).

While miRNAs significantly differentially expressed at the terminal stage show an increase in expression over time (except for mmu-miR10a-5p).

This data demonstrates that the level of expression of a miRNA in a brain sample comprising extracellular vesicles is indicative of a disease state and a disease stage. In particular, the level of expression of a miRNA in a brain sample comprising extracellular vesicles is indicative of prion disease state and prion disease stage.

Figure 10:
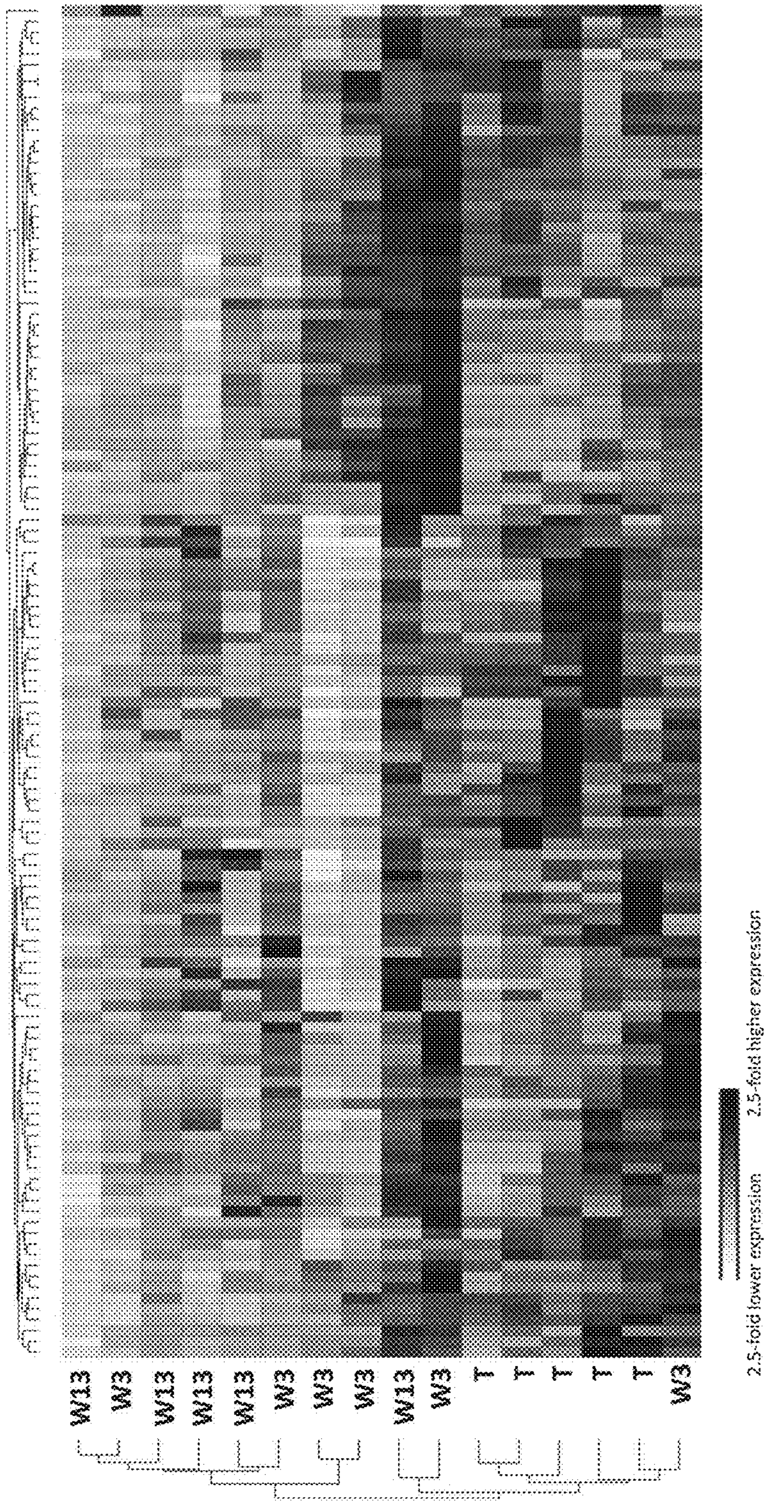
FIG. 10: Expression of miRNA detected in serum exosomes collected from prion M1000 infected and uninfected mice at week 3, 13 and terminal stage. Hierarchical clustering of abundantly expressed miRNA (min >10 RPM across in all samples) in prion M1000 infected mice at week 3, 13 and terminal stage. The darker the shade of grey, the higher the expression of miRNA compared to uninfected.

Example 8: Levels of Small Non-Coding miRNA in Serum are Associated With Prion Disease State and Prion Disease Stage Serum exosomes were also isolated from the same mice analysed above to determine whether a diagnostic read out of pre-clinical prion disease could be obtained from this longitudinal mice study. Global expression of abundantly expressed serum exosomal miRNA of M1000 infected mice across the time course study was observed to be more reproducible (FIG. 10, Table 6).

TABLE 6

| Most abundant miRNAs expressed in the serum<br>Abundantly expressed miRNA in serum |
|---|
| mmu-let-7b-5p |
| mmu-let-7d-5p |
| mmu-let-7g-5p |
| mmu-let-7i-5p |
| mmu-miR-103-3p |

TABLE 6-continued

| Most abundant miRNAs expressed in the serum<br>Abundantly expressed miRNA in serum |
|---|
| mmu-miR-106b-5p |
| mmu-miR-126a-3p |
| mmu-miR-126a-5p |
| mmu-miR-130a-3p |
| mmu-miR-140-3p |
| mmu-miR-144-3p |
| mmu-miR-145a-5p |
| mmu-miR-150-5p |
| mmu-miR-15a-5p |
| mmu-miR-15b-5p |
| mmu-miR-16-5p |
| mmu-miR-17-5p |
| mmu-miR-18a-5p |
| mmu-miR-191-5p |
| mmu-miR-19a-3p |
| mmu-miR-19b-3p |
| mmu-miR-20a-5p |
| mmu-miR-21a-5p |
| mmu-miR-221-3p |
| mmu-miR-222-3p |
| mmu-miR-223-3p |
| mmu-miR-23a-3p |
| mmu-miR-24-3p |
| mmu-miR-25-3p |
| mmu-miR-27a-3p |
| mmu-miR-29a-3p |
| mmu-miR-29b-3p |
| mmu-miR-30a-5p |
| mmu-miR-30b-5p |
| mmu-miR-30d-5p |
| mmu-miR-3107-5p |
| mmu-miR-320-3p |
| mmu-miR-378a-3p |
| mmu-miR-451a |
| mmu-miR-484 |
| mmu-miR-486-5p |
| mmu-miR-93-5p |

*Minimum reads all samples >100 RPM

Figure 11:
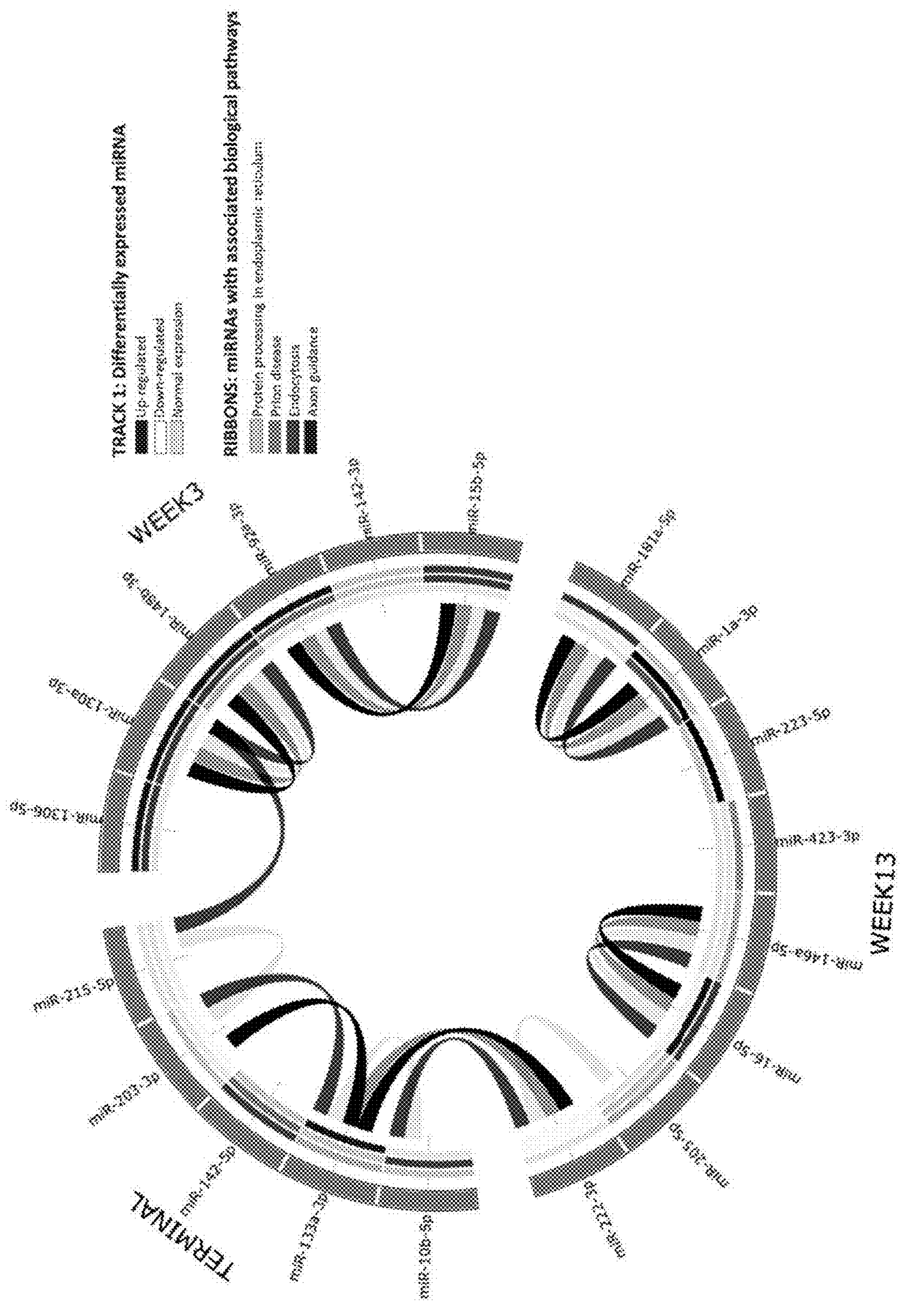
FIG. 11: Circos plot depicting the significant differentially expressed miRNAs in serum exosomes. Statistically significant miRNA (P<0.01, fold change −2 and 2) were identified in prion M1000 mice compared to uninfected mice. The outermost track shows miRNAs that are significantly differentially expressed in week 3, week 13 and terminal stage of disease. The inner tracks illustrate expression heat map across all miRNAs in the time-course study. The expression levels are represented in log 2 fold change. The darker the shade of grey/black, the higher the expression of miRNA compared to uninfected. The ribbons inside the circos plot represent biological pathways the miRNA is involved in including prion diseases, protein processing in endoplasmic reticulum, endocytosis and axon guidance. Prion M1000 week 3 (n=6), week 13 (n=5) and terminal (n=5). Prion uninfected week 3 (n=6), week 13 (n=6) and terminal (n=6).

FIG. 11 shows the DE miRNA (mean >10 RPM across all thalamus samples, p-value <0.05, fold change <⁻1.5 and >1.5, Table 7) observed in serum exosomes of M1000 infected mice compared to uninfected mice at each time point; including six miRNAs (mmu-miR-1306-5p, mmu-miR-130a-3p, mmu-miR-148b-3p, mmu-miR-92a-3p, mmu-miR-142-3p and mmu-miR-15b-5p) that were identified at 3 wpi, eight miRNAs (mmu-miR-181a-5p, mmu-miR-1a-3p, mmu-miR-223-5p, mmu-miR-423-3p, mmu-miR-146a-5p, mmu-miR-16-5p, mmu-miR-205-5p and mmu-miR-222-3p) at 13 wpi and 11 miRNAs (mmu-miR-142-3p, mmu-miR-15b-5p, mmu-miR-146a-5p, mmu-miR-16-5p, mmu-miR-205-5p, mmu-miR-222-3p, mmu-miR-10b-5p, mmu-miR-133a-3p, mmu-miR-142-5p, mmu-miR-203-3p and mmu-miR-215-5p) at terminal stage.

TABLE 7

Differentially expressed miRNA identified in the thalamus

| | | Week 3 preclinical stage Serum | | Week 13 pre-clinical stage Serum | | Terminal stage Serum | |
|---|---|---|---|---|---|---|---|
| Biomarker | Time point | p-value | FC* | p-value | FC* | p-value | FC* |
| mmu-miR-1306-5p | W3 | **0.0396902** | **1.56242** | 0.323129 | 1.37987 | 0.951458 | −1.01181 |
| mmu-miR-130a-3p | W3 | **0.0299279** | **1.58088** | 0.266282 | 1.27904 | 0.511283 | −1.12737 |
| mmu-miR-148b-3p | W3 | **0.0374105** | **1.90161** | 0.575217 | 1.28044 | 0.121289 | −1.65838 |
| mmu-miR-92a-3p | W3 | **0.0174073** | **1.51023** | 0.431542 | 1.19898 | 0.834288 | −1.02923 |
| mmu-miR-142-3p | W3/T | **0.00842767** | **−1.53245** | 0.459868 | −1.22478 | **0.000382** | **−1.8023** |
| mmu-miR-15b-5p | W3/T | **0.0499997** | **1.47179** | 0.327648 | 1.4156 | **0.022705** | **−1.69291** |
| mmu-miR-181a-5p | W13 | 0.7647 | 1.20182 | **0.018231** | **−3.11036** | 0.358598 | −1.48811 |
| mmu-miR-1a-3p | W13 | 0.793019 | −1.08966 | **0.016156** | **2.44338** | 0.707372 | 1.14393 |

TABLE 7-continued

| Differentially expressed miRNA identified in the thalamus | | | | | | | |
|---|---|---|---|---|---|---|---|
| | | Week 3 preclinical stage Serum | | Week 13 pre-clinical stage Serum | | Terminal stage Serum | |
| Biomarker | Time point | p-value | FC* | p-value | FC* | p-value | FC* |
| mmu-miR-223-5p | W13 | 0.212399 | −2.40739 | **0.010029** | **2.31205** | 0.422192 | −1.29238 |
| mmu-miR-423-3p | W13 | 0.603742 | 1.16111 | **0.026073** | **−1.79527** | 0.911576 | 1.01964 |
| mmu-miR-146a-5p | W13/T | 0.459056 | −1.2149 | **0.00058** | **−1.87395** | **0.000425** | **−1.82863** |
| mmu-miR-16-5p | W13/T | 0.0857583 | 1.34601 | **0.048308** | **1.84017** | **0.000307** | **−2.11812** |
| mmu-miR-205-5p | W13/T | 0.624185 | 1.14256 | **0.007889** | **−1.66194** | **0.0001** | **−2.21353** |
| mmu-miR-222-3p | W13/T | 0.943246 | 1.0296 | **0.009048** | **−2.90388** | **0.00727** | **−2.40001** |
| mmu-miR-10b-5p | T | 0.747919 | −1.0871 | 0.322239 | 1.23515 | **0.000307** | **−1.92841** |
| mmu-miR-133a-3p | T | 0.899358 | 1.04169 | 0.672893 | −1.09876 | **0.018162** | **2.0274** |
| mmu-miR-142-5p | T | 0.324333 | 1.19207 | 0.733015 | 1.12464 | **0.029399** | **−1.45771** |
| mmu-miR-203-3p | T | 0.857682 | −1.06741 | 0.218836 | −1.36436 | **0.000529** | **−2.16688** |
| mmu-miR-215-5p | T | 0.306383 | −1.46203 | 0.099677 | −1.56508 | **3.45E−05** | **−1.82609** |

Figure 12:
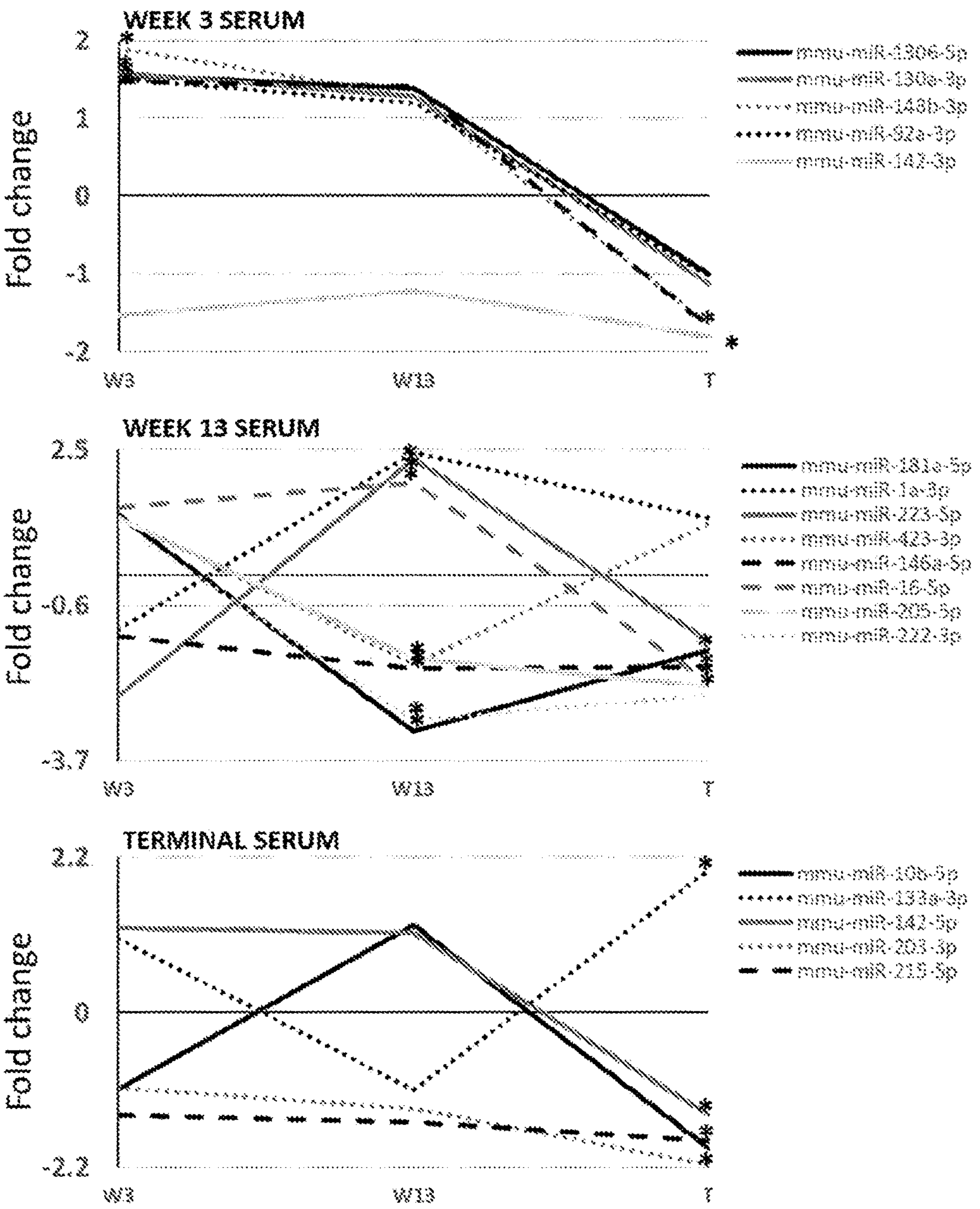
FIG. 12: Longitudinal analysis of the DE miRNAs across week 3, 13 and terminal stage in serum exosomes of prion M1000 infected mice. Statistically significant miRNA (P<0.01, fold change −2 and 2) were identified in prion M1000 mice compared to uninfected mice at each time point and graphed here to display the longitudinal expression change of miRNA. * indicates the time-point which the miRNA was found to be significantly DE (ANOVA p-value <0.05). Prion M1000 infected; week 3 (n=6), week 13 (n=5) and terminal (n=5). Uninfected; week 3 (n=6), week 13 (n=6) and terminal (n=6).

*Prion infected (M1000) Vs control (uninfected), bold values are significant at time point Several miRNAs significantly deregulated at clinical stage were also significantly deregulated at pre-clinical stages which include mmu-miR-142-3p mmu-miR-15b-5p at 3 wpi and terminal stage, and mmu-miR-146a-5p, mmu-miR-16-5p, mmu-miR-205-5p and mmu-miR-222-3p at 13 wpi and terminal stage. A number of these miRNAs found at two time points of the study were then used in the human clinical validation study to test their diagnostic potential with predicting CJD (Table 8) followed by a validation study using a second set of clinical samples. FIG. 12 demonstrates the longitudinal expression changes of serum DE miRNAs are also dynamic while many miRNAs show a decrease in expression over time.

TABLE 8

| Differentially expressed miRNA candidates selected for validation study | | | | | | | | | | | | | |
|---|---|---|---|---|---|---|---|---|---|---|---|---|---|
| | | Week 3 preclinical stage | | | | Week 13 pre-clinical stage | | | | Terminal stage | | | |
| | | Serum | | Thalamus | | Serum | | Thalamus | | Serum | | Thalamus | |
| Biomarker | Timepoint | p-value | FC* | p-value | FC* | p-value | FC* | p-value | FC* | p-value | FC* | p-value | FC* |
| hsa-miR-185-5p | Control | 0.00 | 0.00 | 0.00 | 0.00 | 0.00 | 0.00 | 0.00 | 0.00 | 0.00 | 0.00 | 0.00 | 0.00 |
| hsa-miR-451a | Control | 0.00 | 0.00 | 0.00 | 0.00 | 0.00 | 0.00 | 0.00 | 0.00 | 0.00 | 0.00 | 0.00 | 0.00 |
| hsa-miR-93-5p | Control | 0.00 | 0.00 | 0.00 | 0.00 | 0.00 | 0.00 | 0.00 | 0.00 | 0.00 | 0.00 | 0.00 | 0.00 |
| hsa-miR-10b-5p | T | 0.00 | 0.00 | 0.00 | 0.00 | 0.00 | 0.00 | 0.00 | 0.00 | **0.00** | **−1.93** | 0.23 | −1.78 |
| hsa-miR-133a-3p | T | 0.00 | 0.00 | 0.00 | 0.00 | 0.00 | 0.00 | 0.00 | 0.00 | **0.02** | **2.03** | 0.53 | −1.35 |
| hsa-miR-142-5p | T | 0.00 | 0.00 | 0.00 | 0.00 | 0.00 | 0.00 | 0.00 | 0.00 | **0.03** | **−1.46** | 0.90 | 1.42 |
| hsa-miR-203a-3p | T | 0.00 | 0.00 | 0.00 | 0.00 | 0.00 | 0.00 | 0.00 | 0.00 | **0.00** | **−2.17** | 0.19 | 1.33 |
| hsa-miR-1-3p | W13 | 0.00 | 0.00 | 0.00 | 0.00 | **0.00** | **2.45** | 0.56 | 1.75 | 0.00 | 0.00 | 0.00 | 0.00 |
| hsa-miR-181a-5p | W13 | 0.00 | 0.00 | 0.00 | 0.00 | **0.02** | **−3.11** | **0.01** | **1.62** | 0.00 | 0.00 | 0.00 | 0.00 |
| hsa-miR-423-3p | W13 | 0.00 | 0.00 | 0.00 | 0.00 | 0.03 | **−1.80** | **0.07** | **1.68** | 0.00 | 0.00 | 0.00 | 0.00 |
| hsa-miR-101-3p | W13/T | 0.00 | 0.00 | 0.00 | 0.00 | 0.75 | 1.50 | **0.05** | **1.64** | 0.73 | −1.34 | 0.01 | −1.54 |
| hsa-miR-146a-5p | W13/T | 0.00 | 0.00 | 0.00 | 0.00 | **0.00** | **−1.87** | 0.84 | 2.57 | **0.00** | **−1.83** | 0.24 | 6.18 |
| hsa-miR-16-5p | W13/T | 0.00 | 0.00 | 0.00 | 0.00 | **0.05** | **1.84** | 0.87 | 1.19 | **0.00** | **−2.12** | 0.79 | −1.15 |
| hsa-miR-205-5p | W13/T | 0.00 | 0.00 | 0.00 | 0.00 | **0.01** | **−1.66** | 0.97 | −1.42 | **0.00** | **−2.21** | 0.99 | −1.26 |
| hsa-miR-222-3p | W13/T | 0.00 | 0.00 | 0.00 | 0.00 | **0.01** | **−2.90** | 0.83 | 2.20 | **0.01** | **−2.40** | 0.97 | −1.09 |
| hsa-miR-1306-5p | W3 | **0.04** | **1.56** | 0.49 | −1.52 | 0.00 | 0.00 | 0.00 | 0.00 | 0.00 | 0.00 | 0.00 | 0.00 |
| hsa-miR-130a-3p | W3 | **0.03** | **1.58** | 0.37 | 1.39 | 0.00 | 0.00 | 0.00 | 0.00 | 0.00 | 0.00 | 0.00 | 0.00 |
| hsa-miR-148b-3p | W3 | **0.04** | **1.90** | 0.41 | −1.24 | 0.00 | 0.00 | 0.00 | 0.00 | 0.00 | 0.00 | 0.00 | 0.00 |
| hsa-miR-92a-3p | W3 | **0.02** | **1.51** | 1.00 | −1.00 | 0.00 | 0.00 | 0.00 | 0.00 | 0.00 | 0.00 | 0.00 | 0.00 |
| hsa-miR-142-3p | W3/T | **0.01** | **−1.53** | 0.95 | −1.05 | 0.00 | 0.00 | 0.00 | 0.00 | **0.00** | **−1.80** | **0.02** | **2.49** |

*Prion infected (M1000) Vs control (uninfected) Bold values are significant at time point Identification of prion diseases and their associated biological pathways to gain insight into the biological pathways of differentially expressed miRNAs associated with the pre-clinical and clinical stage, enrichment analysis of multiple miRNA targets to all known KEGG pathways were performed. During the earliest stage in the thalamus at week 3, the differentially expressed miRNAs (mmu-miR-129-1-3p, mmu-miR-129b-5p, mmu-miR-337-3p) in the M1000 infected mice were not found to target genes involved in known KEGG pathways (FIG. 8). However, at the later stage of infection at week 13, six deregulated miRNAs were found to have target in signalling pathways involved in MAPK Signalling, axon guidance, long term potentiation, prion disease, protein processing in the endoplasmic reticulum and endocytosis (FIG. 8). Furthermore, these signalling pathways were also identified in the terminal stage of disease and were associated with mmu-miR-223-3p and mmu-miR-10a-5p. In serum exosomes, the majority of deregulated miRNA at all timepoints were found to target genes involved in protein processing in the endoplasmic reticulum, prion disease, endocytosis and axon guidance (FIG. 11).

This data demonstrates that the level of expression of a miRNA in a serum sample comprising extracellular vesicles is indicative of a disease state and a disease stage. In particular, the level of expression of a miRNA in a serum sample comprising extracellular vesicles is indicative of prion disease state and prion disease stage.

Figure 13:
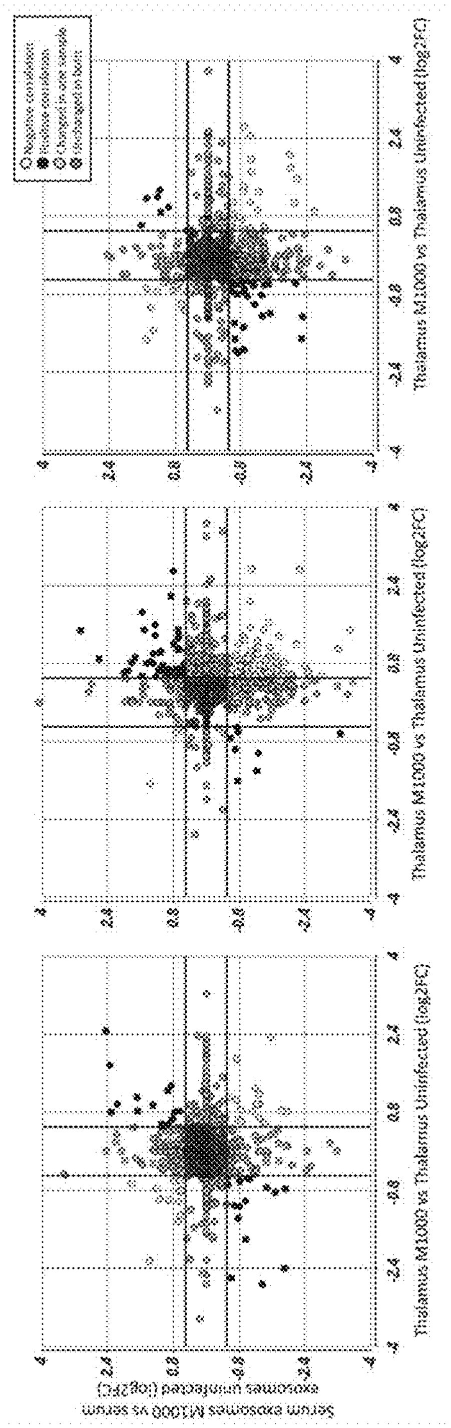
FIG. 13: Direction of global miRNA expression changes in the thalamus and serum exosomes of prion M1000 infected mice at week 3, 13 and terminal stage compared to controls. ANOVA analysis was performed on the normalised reads from both datasets (thalamus and serum exosomes) and were plotted as Log 2 fold change. miRNA found to display inverse (negative correlation) expression in serum exosomes and BDEs are indicated by the white datapoints. Those found to display the same direction (positive correlation) in expression (either upregulated or downregulated) in both sample types are indicated by the black datapoints. miRNA found unchanged in both sample types are indicated in dark grey and those changed in one sample type are indicated in light grey. Thalamus prion M1000 week 3 (n=4), week 13 (n=4) and terminal (n=5). Thalamus prion uninfected week 3 (n=5), week 13 (n=5) and terminal (n=5). Serum prion M1000 week 3 (n=6), week 13 (n=5) and terminal (n=5). Ser prion uninfected week 3 (n=6), week 13 (n=6) and terminal (n=6).
Figure 14:
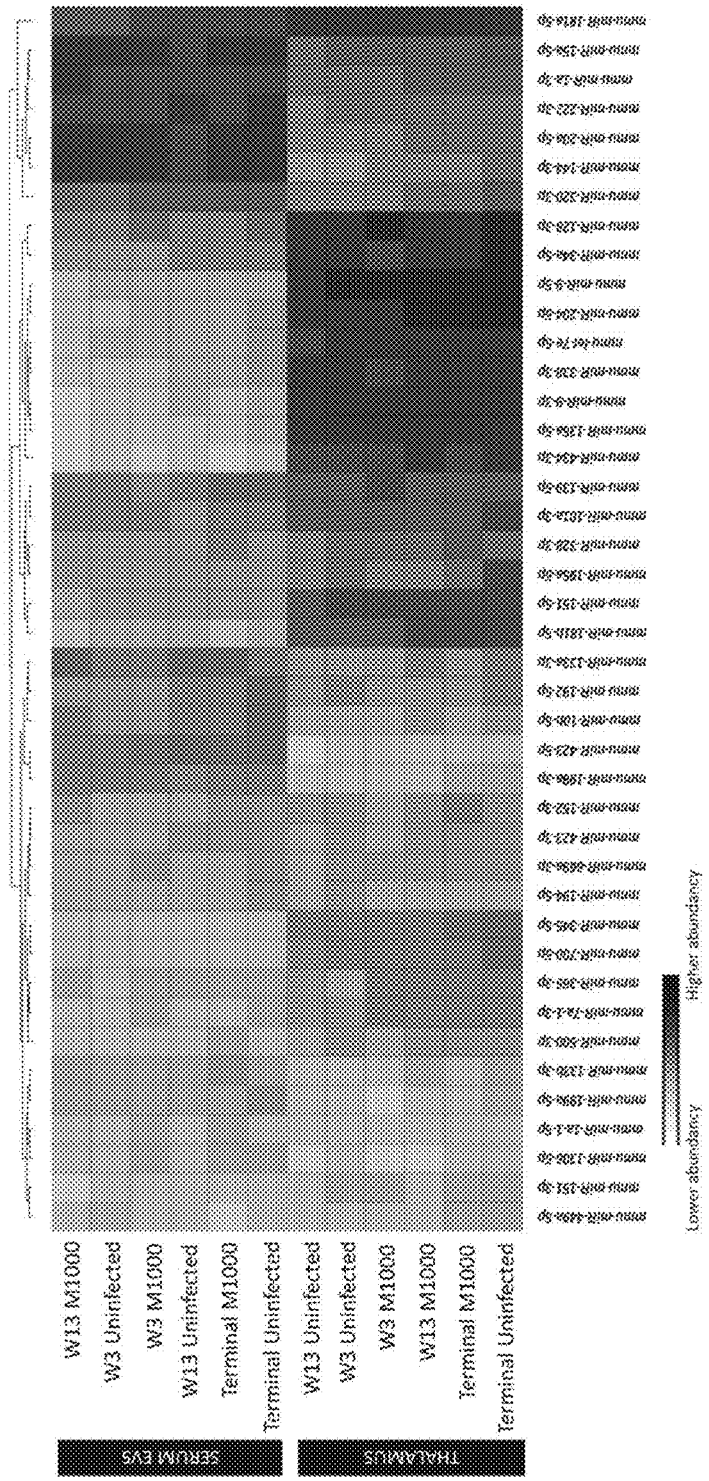
FIG. 14: Abundancy of brain-derived miRNAs found in both the thalamus and serum. miRNAs indicated in white and black from FIG. 13 are displayed in a heat map to visualise the abundancy of their expression in the thalamus and serum EVs. Only miRNAs with a minimum of 5 RPM across all samples are shown here. $Log_2$ Mean RPM of each miRNA was used for the heat map. The darker the shade of grey, the higher the abundance of miRNA.

Example 9: Association of Levels of Small Non-Coding miRNA in Brain Tissue Derived Exosomes Associated with Prion Disease State and/or Stage and Levels of Small Non-Coding miRNA in Serum Associated with Prion Disease State and/or Stage Three miRNAs were found to be significantly deregulated in both the thalamus and serum exosomes which were mmu-miR-181a-5p, mmu-miR-1a-3p and mmu-miR-142-3p and would therefore be ideal biomarkers to validate as a liquid brain biopsy. mmu-miR-1a-3p was observed to be upregulated approximately 2-fold in both the thalamus and serum exosomes at 13 wpi. While, mmu-181a-5p was found to be upregulated in the thalamus but downregulated in serum exosomes. mmu-miR-142-3p was found to be expressed in the opposite direction at the terminal stage in the thalamus compared to serum exosomes. To visualise the global direction of expression between miRNA found in the thalamus and serum exosomes, the fold changes (Log 2) between M1000 infected V's uninfected observed in the thalamus and serum exosomes at all timepoints were plotted in FIG. 13. While many miRNAs were found to display unchanged expression in both the thalamus region and serum exosomes of M1000 infected samples compared to uninfected samples (FIG. 13, dark grey datapoints), other miRNAs were found to be changed in only one sample type and not the other (FIG. 13, light grey datapoints). Interestingly, there were other miRNAs other than mmu-miR-181a-5p and mmu-miR-142-3p that displayed an inverse expression between the two sample types (FIG. 13, white datapoints). At 13 wpi, there was an increase of upregulated miRNAs upregulated in M1000 infected thalamus while the same miRNAs were downregulated in the serum (FIG. 13, panel 2, lower right quadrant, white datapoints) compared to what was observed at 3 wpi and terminal stage (FIG. 13, panel 1 and 3, lower right quadrant, white datapoints). This may allude to a possible biological event that occurs at the blood brain barrier (BBB) whereby the shuttling, uptake and use of exosomal miRNA by endothelial cells of the BBB influences the expression of miRNA in these samples. The comparison of these samples also revealed a number of miRNAs that displayed the same direction of expression, either upregulated or downregulated, in both sample types (FIG. 13, black datapoints). Those found to be upregulated in both the brain and serum exosomes of M1000 infected mice such as mmu-miR-1a-3p were ideal for the validation study (Table 8) as they would be easily detectable by qRT-PCR.

Example 10: Validation of Methods of Diagnosing a Prion Disease State and/or Stage Using Levels of Small Non-Coding miRNA in Serum Associated with a Prion Disease State and/or Stage Prion diseases include three forms: sporadic, familial and acquired by infection which can display different pathological features. While the incubation period or pre-clinical period may be long (up to 4 decades) CJD can progress very rapidly upon clinical diagnosis. Several mutations at Codon 129 of the prion protein gene (PRNP) is the site of a common methionine (M)/valine (V) polymorphism which leads to certain phenotypes of human prion diseases such as CJD. In the Caucasian population, 52% of individuals are M homozygous (MM), 36% are heterozygous (MV) and 12% are V homozygous (VV). The mean onset of the disease with those who are MM homozygous or MV heterozygous is 65 years and the average clinical duration is 4 months with a range of 1-18 months. Those who are V homozygous have been observed to have a clinical duration of 3-18 months where the mean age of onset to be between 41-81 years. In this longitudinal study, statistically significant miRNA identified in the M1000 mice model at pre-clinical and clinical timepoints (Tables 7 and 8) were selected for validation in a set of Human clinical samples collected from CJD patients and controls.

Figure 15:
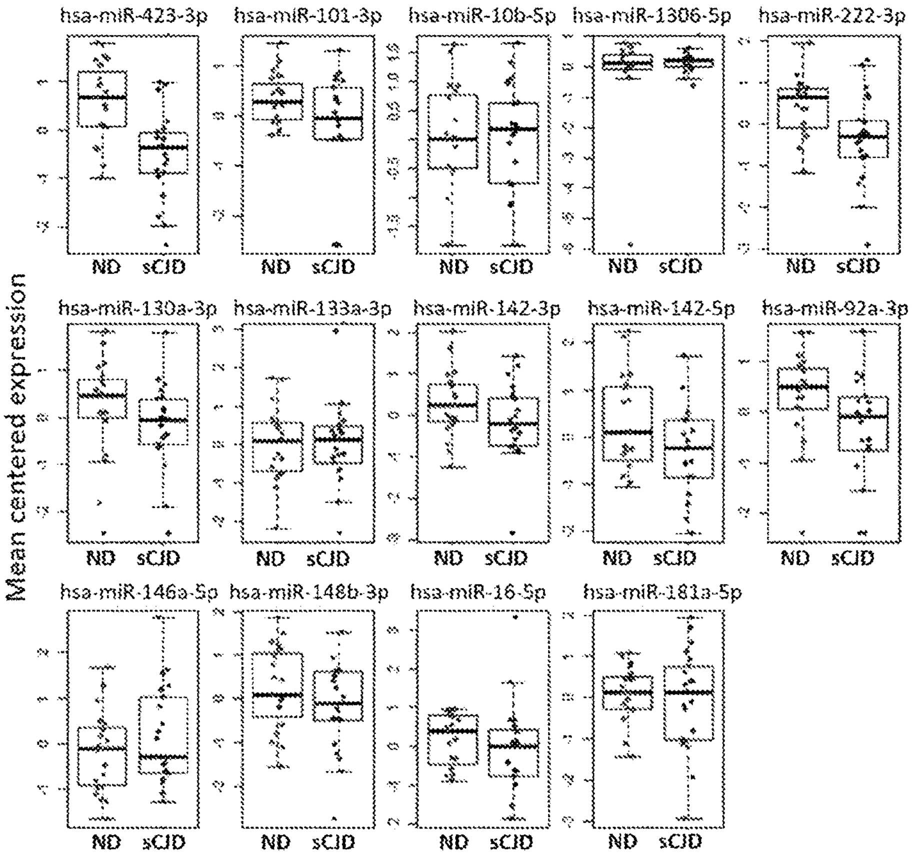
FIG. 15: Box plots showing validated serum exosomal miRNA differentially expressed in non-dementia controls and subjects with Creutzfeldt-Jakob disease. Mean centred and scaled data were plotted between HC and CJD participants. HC, n=20 and CJD, n=26. Here, sCJD is also known as CJD.

Serum samples from Human CJD cases and controls (obtained from the National Reference Centre for Prion Disease, Germany, Table 9) which comprised of subjects who were MM homozygous (n=14) and VV homozygous (n=12) that were clinically diagnosed with CJD (Table 9). The controls used were aged matched non-demented subjects who were MM homozygous and MV heterozygous with no clinical symptoms of CJD (n=20). Exosomal miRNA was extracted and analysed by qRT-PCR using the primers towards 17 DE miRNAs identified in pre-clinical and clinical M1000 infected mice (FIG. 8, 11 and Table 8) and 3 endogenous controls (Table 8). Upon the acquisition of the qRT-PCR data, 5 miRNAs were undetected across all serum samples, most likely to biological diversity in the human population and lower abundancy in human serum or the volume collected (500 ul). Box plots of qRT-PCR data for each remaining miRNA markers (12 miRNA species) are stratified by clinical classification are presented in FIG. 15.

TABLE 9

Demographics of human clinical patients with CJD

| Codon 129-PrPres Subtype | CJD M/M1 | CJD V/V2 | CJD M/V | ND (M/M or M/V or None) |
|---|---|---|---|---|
| Training cohort | | | | |
| n | 14 | 12 | — | 20 |
| Female | 5 | 7 | — | 8 |
| Male | 9 | 5 | — | 12 |
| Mean age (years) | 70 · 1 | 61.8 | — | 64.3 |
| SD age (years) | 8.4 | 10.0 | — | 14.7 |
| Clinical duration (months) | 2-5 | 2-15 | — | N/A |
| 14-3-3 positive (WB or ELISA) | 9 | 6 | — | N/A |

TABLE 9-continued

| Demographics of human clinical patients with CJD | | | | |
|---|---|---|---|---|
| Codon 129-PrPres Subtype | CJD M/M1 | CJD V/V2 | CJD M/V | ND (M/M or M/V or None) |
| Validation cohort | | | | |
| n | 15 | 3 | 1 + 1 unknown | 6 |
| Female | 10 | 2 | 2 | 3 |
| Male | 5 | 1 | 0 | 3 |
| Mean age (years) | 68.4 | 67 | 63 | 62 |
| SD age (years) | 9.4 | 6 | 9.9 | 9.8 |
| Clinical duration (months) | 1-17 | 4.1-10 | 3-25 | N/A |
| 14-3-3 positive (WB or ELISA) | 13 | 2 | — | N/A |

Figure 16:
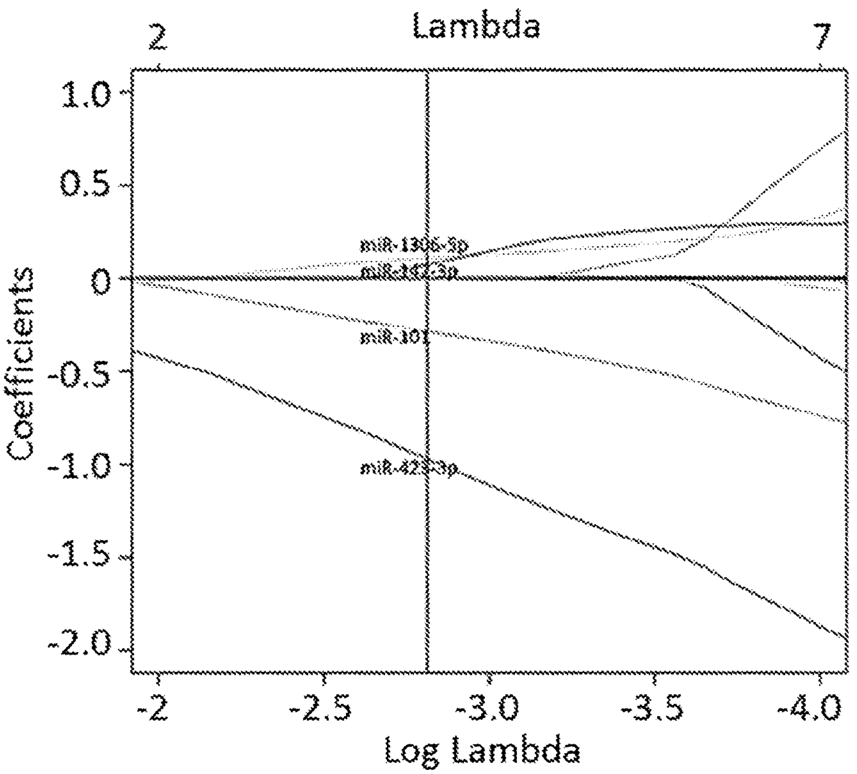
FIG. 16: Performance of the LASSO mode used to construct a miRNA signature to diagnose CJD. LASSO coefficient profiles of the 14 miRNAs including age and a random variable generated using the training cohort. Each curve corresponds to a miRNA. The vertical line is drawn at the value $\lambda$=0.0794 chosen by 1000× cross-validation.
Figure 17:
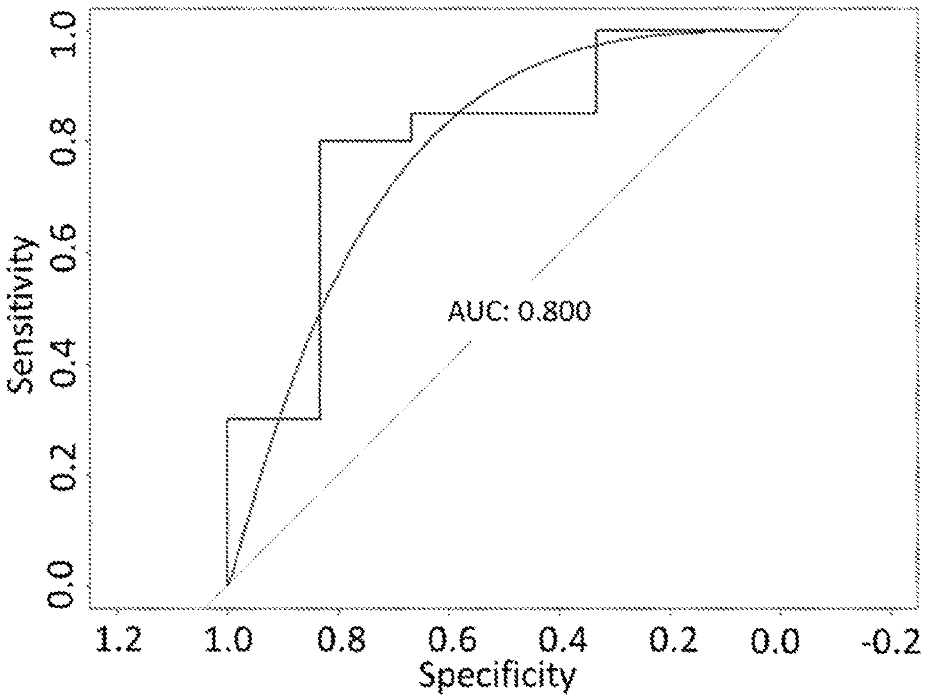
FIG. 17: AUC for predicting CJD Receiver operating characteristic (ROC) curve for the performance of miRNAs and AUC values calculated using a second cohort of samples as the validation set.
Figure 18:
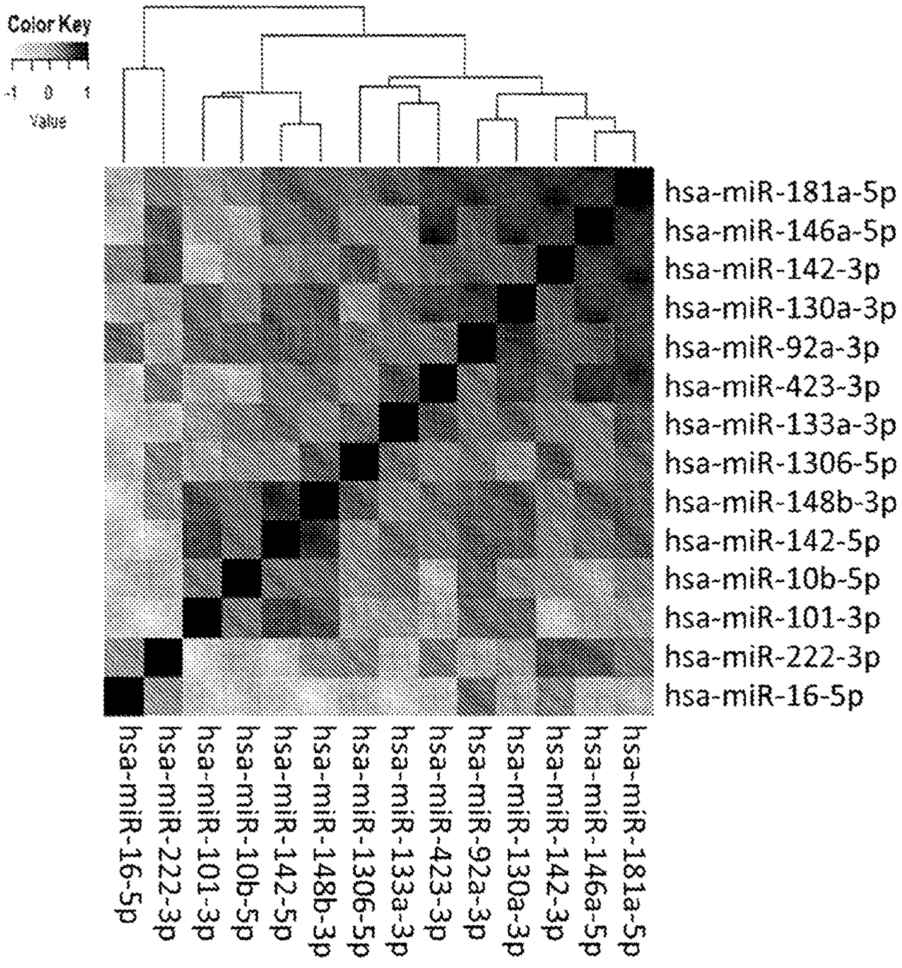
FIG. 18: Correlation matrix heatmap of the 14 miRNAs from the training cohort. Each cell represents the Pearson correlation between the miRNA indicated in the corresponding row and columns. Dendrograms show the hierarchical clustering of the collinearity of the 14 candidate miRNAs.
Figure 19:
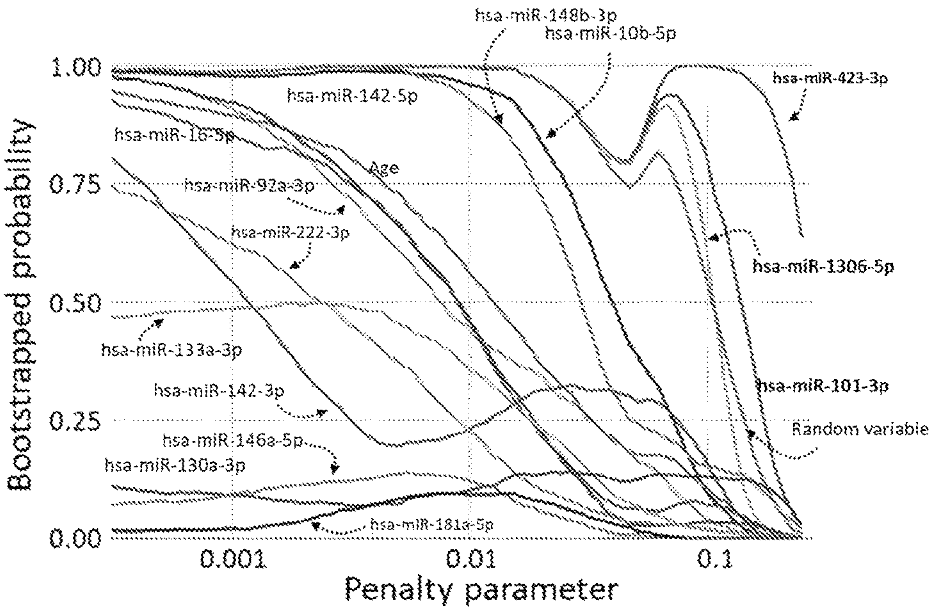
FIG. 19: The variable inclusion plots that indicate the three most important features above reference variable (RV)
Figure 20:
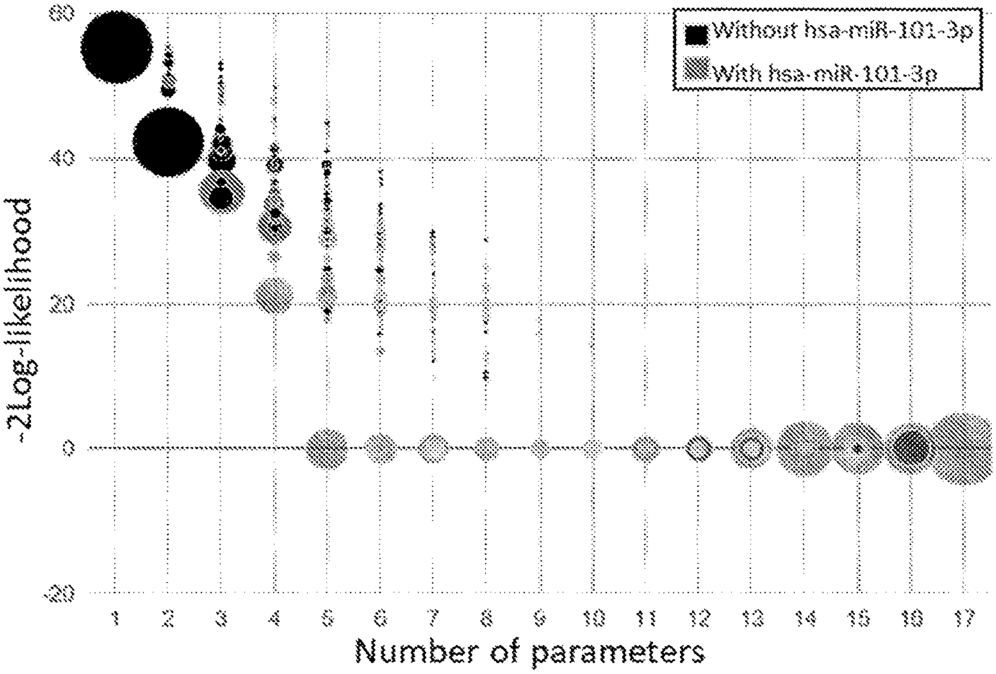
FIG. 20: Model stability bubble plot of hsa-miR-101-3p. Model stability bubble plots representing the stability of the model with the presence and absence of one of the strongest miRNAs in the model, hsa-miR-101-3p. Each bubble represents a model and the colour of the bubble indicates whether (red) or not (blue) the model includes the particular miRNA. The size of the bubble corresponds to the probability of the model of the same size obtained from the 1000× cross-validation.
Figure 21:
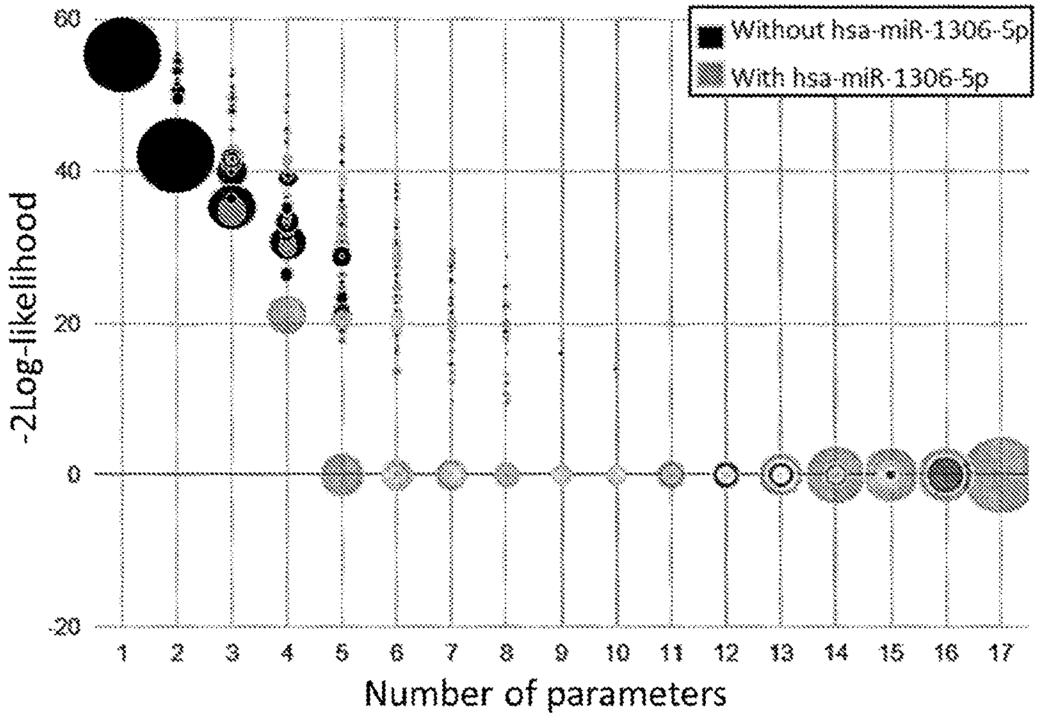
FIG. 21: Model stability bubble plot of hsa-miR-1306-5p. Model stability bubble plots representing the stability of the model with the presence and absence of one of the strongest miRNAs in the model, hsa-miR-1306-5p. Each bubble represents a model and the colour of the bubble indicates whether (red) or not (blue) the model includes the particular miRNA. The size of the bubble corresponds to the probability of the model of the same size obtained from the 1000× cross-validation.
Figure 22:
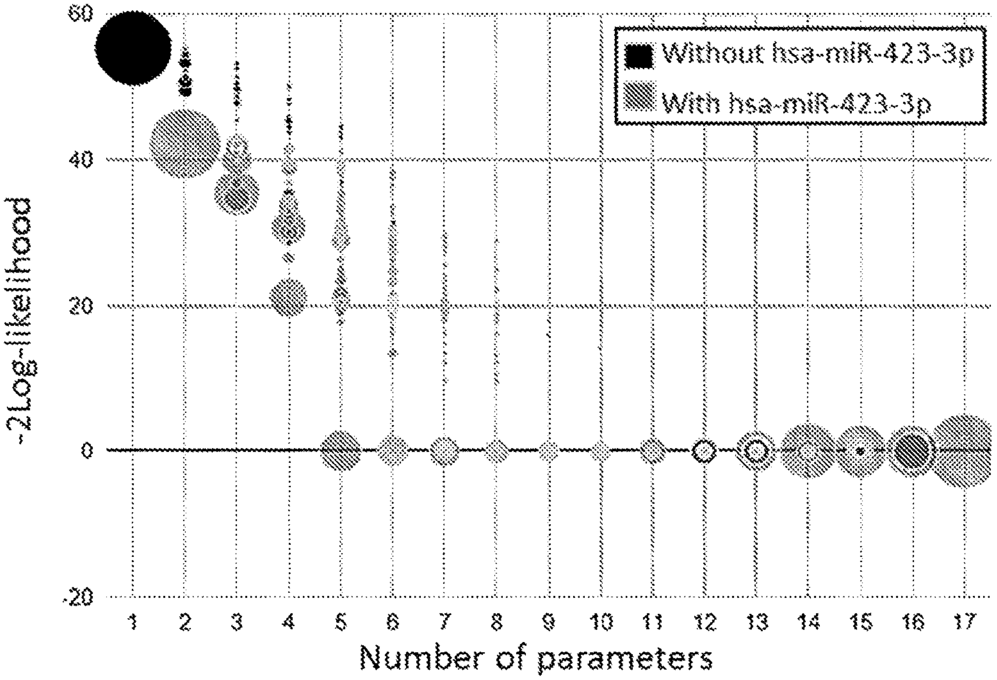
FIG. 22: Model stability bubble plot of hsa-miR-423-3p. Model stability bubble plots representing the stability of the model with the presence and absence of one of the strongest miRNAs in the model, hsa-miR-423-3p. Each bubble represents a model and the colour of the bubble indicates whether (red) or not (blue) the model includes the particular miRNA. The size of the bubble corresponds to the probability of the model of the same size obtained from the 1000× cross-validation.

Finally, LASSO model was applied on the whole dataset and the coefficient profiles of the 14 miRNAs and age at $\lambda$=0.060 indicate 4 features (hsa-miR-423-3p, hsa-miR-101-3p, hsa-miR-1306-5p and hsa-miR-142-3p) that influence the response variable the strongest (FIG. 16) providing a AUC of 0.924 on predicting CJD in the discovery set. LASSO analysis correctly diagnosed 18 out of 21 CJD subjects (85.7% sensitivity) and confirmed 17 out of 19 to be control subjects (89.5% specificity). A second cohort of samples was obtained (Table 9) and a validation study was performed on an additional 26 clinical samples (CJD, n=20 and ND, n=6). The model was able to correctly confirm 17 out of 20 CJD patients and 4 out of 6 ND controls. The resultant sensitivity was 85% and specificity at 66.7% with an AUC of 0.800 in the validation cohort (FIG. 17). The correlation matrix heatmap of the 14 miRNAs from the training cohort suggests that there are clusters of miRNAs that display a strong positive correlation and to a lesser extent, some negative correlations (FIG. 18). Variable inclusion plot demonstrate which variables are important based on 1000 bootstrap sampling (FIG. 19). Model stability plots (FIG. 20-22) demonstrated the reliability of the final predictive model whereby the inclusion of up to 17 variables during bootstrap resampling displayed dominant models required the strongest 3 miRNAs (hsa-miR-101-3p, FIG. 20, hsa-miR-1306-5p, FIG. 21 and hsa-miR-423-3p, FIG. 22).

Example 11: Levels of Small Non-Coding miRNA in Serum are Associated With Dementia, Parkinson's Disease and CJD Examination of small non-coding miRNA in serum of patients with dementia indicated that 11 serum exosomal miRNA were found to be significantly deregulated in patients with dementia, relative to healthy controls: hsa-miR-1306-5p (SEQ ID NO: 22), hsa-miR-342-3p (SEQ ID NO: 79), hsa-miR-15b-3p (SEQ ID NO: 71), hsa-miR-15a-5p (SEQ ID NO: 72), hsa-miR-143-3p (SEQ ID NO: 73), hsa-miR-335-5p (SEQ ID NO: 74), hsa-miR-106b-5p (SEQ ID NO: 75), hsa-miR-101-3p (SEQ ID NO: 61), hsa-miR-106a-5p (SEQ ID NO: 76), hsa-miR-20a-5p (SEQ ID NO: 77), and hsa-miR-30e-5p (SEQ ID NO: 78), as shown in Table 10. Table 10 also shows 5 serum exosomal miRNA found to be significantly deregulated in patients with PD: hsa-miR-1306-5p (SEQ ID NO: 22), hsa-miR-142-5p (SEQ ID NO: 56), hsa-miR-146a-5p (SEQ ID NO: 62), hsa-miR-142-3p (SEQ ID NO: 70), and hsa-miR-1-3p (SEQ ID NO: 58), and 5 serum exosomal miRNA found to be significantly deregulated in patients with CJD; hsa-miR-1306-5p (SEQ ID NO: 22), hsa-miR-181a-5p (SEQ ID NO: 7), hsa-miR-193a-5p (SEQ ID NO: 10), hsa-miR-199a-5p (SEQ ID NO: 23), and hsa-miR-122-5p (SEQ ID NO: 3)

TABLE 10

| | miRNA | Assay ID (Thermo Scientific) | miRBase ID | Nucleotide sequence | Dysregulated in serum data |
|---|---|---|---|---|---|
| 2*** | hsa-miR-1306-5p | ID: 242734_mat | MIMAT0022726 | CCACCUCCCCUGCAAACGUCCA | Significantly downregulated or upregulated in Dementia patents, PD patients and CJD patients |
| 2 | hsa-miR-342-3p | ID: 002260 | MIMAT0000753 | UCUCACACAGAAAUCGCACCCGU | Significantly downregulated in Dementia patents |
| 3 | hsa-miR-15b-3p | ID: 002173 | MIMAT0004586 | CGAAUCAUUAUUUGCUGCUCUA | Significantly downregulated in Dementia patents |
| 4 | hsa-miR-15a-5p | ID: 000389 | MIMAT0000068 | UAGCAGCACAUAAUGGUUUGUG | Significantly upregulated in Dementia patents |
| 5 | hsa-miR-143-3p | ID: 002249 | MIMAT0000435 | UGAGAUGAAGCACUGUAGCUC | Significantly upregulated in Dementia patents |
| 6 | hsa-miR-335-5p | ID: 000546 | MIMAT0000765 | UCAAGAGCAAUAACGAAAAAUGU | Significantly upregulated in Dementia patents |
| 7 | hsa-miR-106b-5p | ID: 000442 | MIMAT0000680 | UAAAGUGCUGACAGUGCAGAU | Significantly upregulated in Dementia patents |
| 8 | hsa-miR-101-3p | ID: 002253 | MIMAT0000099 | UACAGUACUGUGAUAACUGAA | Significantly upregulated in Dementia patents |
| 9 | hsa-miR-106a-5p | ID: 002169 | MIMAT0000103 | AAAAGUGCUUACAGUGCAGGUAG | Significantly upregulated in Dementia patents |

TABLE 10-continued

| | miRNA | Assay ID (Thermo Scientific) | miRBase ID | Nucleotide sequence | Dysregulated in serum data |
|---|---|---|---|---|---|
| 10 | hsa-miR-20a-5p | ID: 000580 | MIMAT0000075 | UAAAGUGCUUAUAGUGCAGGUAG | Significantly upregulated in Dementia patents |
| 11 | hsa-miR-30e-5p | ID: 000421 | MIMAT0000692 | UGUAAACAUCCUUGACUGGAAG | Significantly upregulated in Dementia patents |
| 12 | hsa-miR-181a-5p | ID: 000480 | MIMAT0000256 | AACAUUCAACGCUGUCGGUGAGU | Significantly downregulated in PD patents |
| 13 | hsa-miR-193a-5p | ID: 002281 | MIMAT0004614 | UGGGUCUUUGCGGGCGAGAUGA | Significantly upregulated in PD patents |
| 14 | hsa-miR-199a-5p | ID: 000498 | MIMAT0000231 | CCCAGUGUUCAGACUACCUGUUC | Significantly upregulated in PD patents |
| 15 | hsa-miR-122-5p | ID: 002245 | MIMAT0000421 | UGGAGUGUGACAAUGGUGUUUG | Significantly upregulated in PD patents |
| 16 | hsa-miR-142-5p | ID: 002248 | MIMAT0000433 | CAUAAAGUAGAAAGCACUACU | Significantly upregulated in CJD patents |
| 17 | hsa-miR-146a-5p | ID: 000468 | MIMAT0000449 | UGAGAACUGAAUUCCAUGGGUU | Significantly upregulated in CJD patents |
| 18 | hsa-miR-142-3p | ID: 000464 | MIMAT0000434 | UGUAGUGUUUCCUACUUUAUGGA | Significantly upregulated in CJD patents |
| 19 | hsa-miR-1-3p | ID: 002222 | MIMAT0000416 | UGGAAUGUAAAGAAGUAUGUAU | Significantly upregulated in CJD patents |

Example 12: Levels of Small Non-Coding miRNA in Brain Tissue Derived Exosomes are Associated with AD Disease State To determine whether exosomal miRNA are also deregulated in exosomes from the brains of AD participants, BDEs from post-mortem tissues of AD subjects were isolated and compared to control tissue. The isolation of exosomes from brain tissues was performed as previously published and met the criteria established by the International Society of Extracellular Vesicles (ISEV) to ensure vesicles isolated were bona fide exosomes as per Examples 1 and 3.

Figure 23:
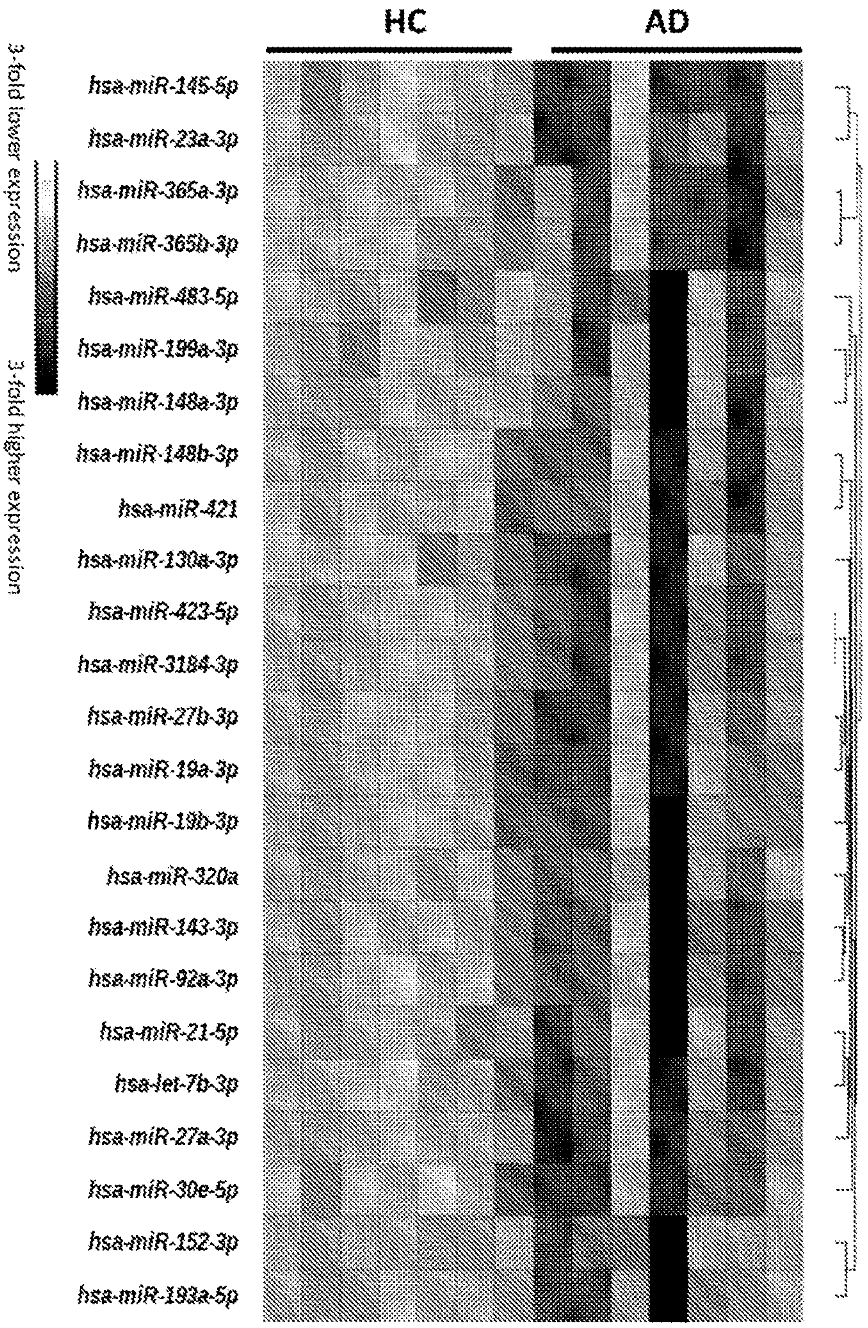
FIG. 23: Expression of miRNA detected in brain derived exosomes from AD subjects and their detection in serum exosomes Hierarchical clustering was performed using Partek Genomics Suite on significantly differentially expressed miRNA using Euclidean average linkage by miRNA. 24 miRNA were found to be significantly deregulated (FDR (AD Vs HC)≤0.05 and ±2 fold change) between AD brain derived exosomes ("BDE")(n=7) compared to controls (n=7). The darker the shade of grey, the higher the expression of miRNA compared to HC

Small RNA content was profiled using next generation sequencing to identify deregulated exosomal miRNA from the post-mortem brain tissue of AD subjects (as also performed in example 1). Upon performing ANOVA analysis with only the abundant miRNA species, 24 miRNAs were found to be significantly upregulated in AD brain derived exosomes (n=7) compared to controls (n=7, FIG. 23, Table 11). There were no miRNAs that were found to be significantly downregulated in the brain derived exosomes from AD tissues. Without wishing to be bound by theory, suggests that these miRNAs are being packaged at greater copy numbers in brain derived exosomes within AD brains compared to controls.

This data demonstrates that miRNA deregulated in brain derived exosomes can be used to diagnose a disease state of a human subject.

TABLE 11

Differentially expressed brain derived exosomal miRNA associated with AD versus HC (healthy controls)

| miRNA | *p-value (AD vs. HC) | FoldChange (AD vs. HC) | Description |
|---|---|---|---|
| hsa-miR-92a-3p | 0.0032 | 2.3265 | AD up vs HC |
| hsa-miR-145-5p | 0.0065 | 2.0107 | AD up vs HC |
| hsa-miR-365a-3p | 0.0076 | 3.2198 | AD up vs HC |
| hsa-miR-23a-3p | 0.0091 | 2.3767 | AD up vs HC |
| hsa-miR-27a-3p | 0.0115 | 2.9499 | AD up vs HC |
| hsa-miR-148a-3p | 0.013 | 3.9475 | AD up vs HC |
| hsa-miR-193a-5p | 0.0132 | 2.4891 | AD up vs HC |
| hsa-miR-148b-3p | 0.0152 | 3.0215 | AD up vs HC |
| hsa-miR-143-3p | 0.0154 | 3.1316 | AD up vs HC |
| hsa-miR-3184-3p | 0.0198 | 2.0658 | AD up vs HC |
| hsa-miR-423-5p | 0.0198 | 2.0658 | AD up vs HC |
| hsa-miR-27b-3p | 0.0203 | 2.2798 | AD up vs HC |
| hsa-miR-30e-5p | 0.0204 | 2.0961 | AD up vs HC |
| hsa-miR-365b-3p | 0.022 | 2.7908 | AD up vs HC |
| hsa-miR-320a | 0.0228 | 2.2204 | AD up vs HC |
| hsa-miR-421 | 0.0252 | 2.2577 | AD up vs HC |
| hsa-miR-199a-3p | 0.0257 | 2.7675 | AD up vs HC |
| hsa-let-7b-3p | 0.0264 | 2.1669 | AD up vs HC |
| hsa-miR-21-5p | 0.0273 | 2.1164 | AD up vs HC |
| hsa-miR-130a-3p | 0.0287 | 2.3003 | AD up vs HC |
| hsa-miR-483-5p | 0.0323 | 2.9191 | AD up vs HC |
| hsa-miR-152-3p | 0.0326 | 3.865 | AD up vs HC |
| hsa-miR-19a-3p | 0.036 | 2.4373 | AD up vs HC |
| hsa-miR-19b-3p | 0.0452 | 2.218 | AD up vs HC |

*HC, n = 7 and AD, n = 7

Figure 24:
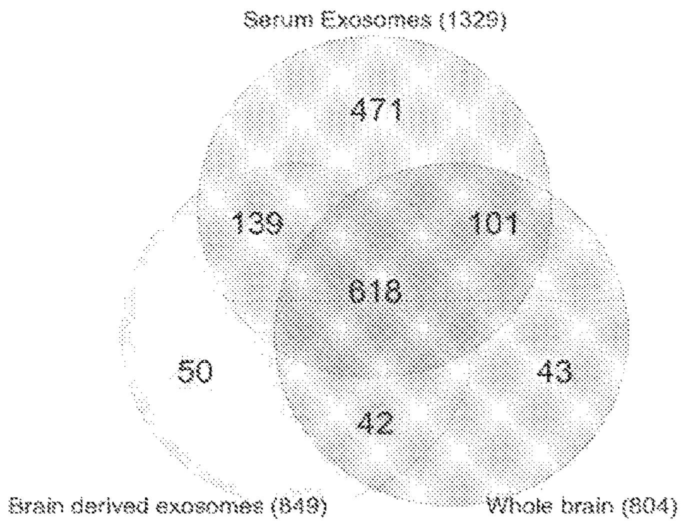
FIG. 24: Venn diagram shows the common and unique miRNA species identified in brain derived exosomes, serum exosomes and whole brain tissue of AD subjects.

Example 13: Association of Levels of Small Non-Coding miRNA in Brain Tissue Derived Exosomes Associated with AD Disease State and Levels of Small Non-Coding miRNA in Serum Associated with AD Disease State Serum exosomes were also isolated from clinically diagnosed AD patients. Overall, the number of individual miRNA species detected in brain derived exosomes, serum exosomes and whole brain was 849, 1329 and 804 respectively (FIG. 24). Two of the 24 miRNAs (hsa-miR-143-3p (SEQ ID NO: 73), and hsa-miR-30e-5p (SEQ ID NO: 78)) were found to be significantly differentially expressed (FDR (AD Vs HC)≤0·05 and ±1.2-fold change) in exosomal serum isolated from AD participants and BDE's from AD subjects compared to controls ((FDR (AD Vs HC)≤0·05 and ±2-fold change, FIGS. 23 and 25).

The remaining 22 brain derived exosomal miRNAs significantly deregulated (Table 11) were also found to be detected in serum exosomes of AD patients, although they did not show significant changes.

Figure 25:
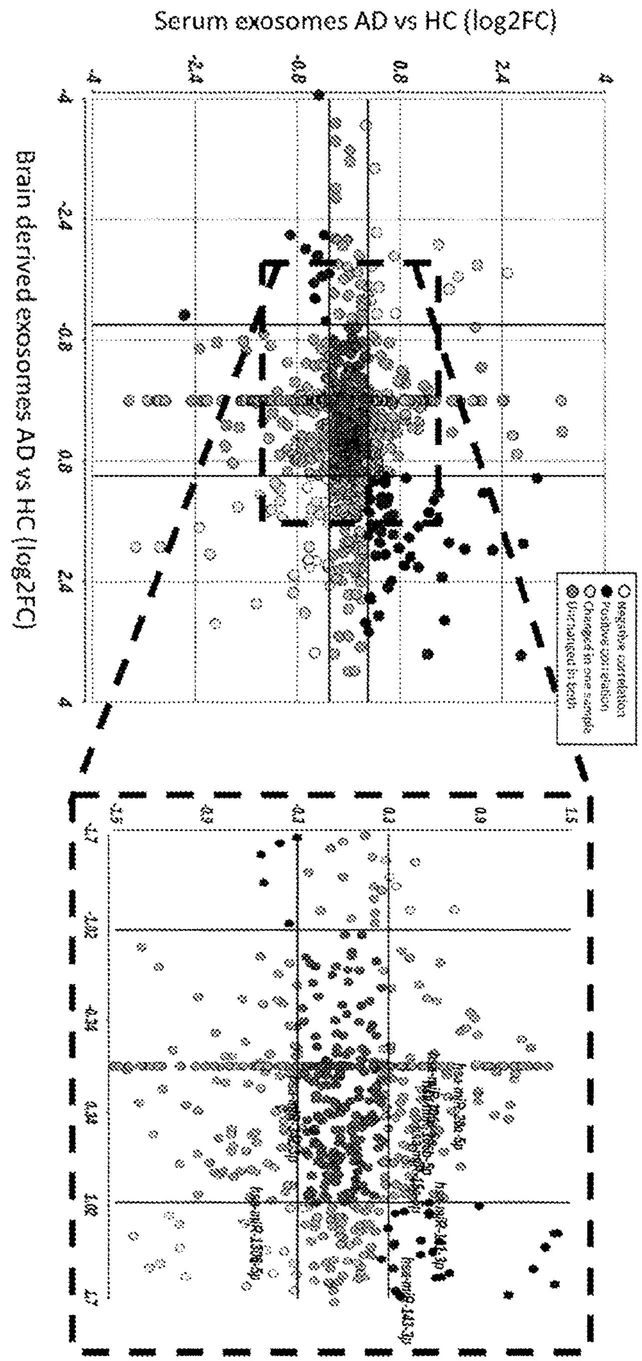
FIG. 25: Direction of global miRNA changes in brain derived exosomes and serum exosomes of AD samples compared to controls. ANOVA analysis was performed on the normalised reads from both small RNA datasets (BDE's and serum exosomes) and were plotted as Log 2 fold change. miRNA found to display inverse (negative correlation) expression in serum exosomes and BDEs are indicated by the white datapoints. Those found to display the same direction (positive correlation) in expression (either upregulated or downregulated) in both sample types are indicated by the black datapoints. miRNA found unchanged in both sample types are indicated in dark grey and those changed in one sample type are indicated in light grey. The insert in the figure outlined by the dashed border focuses on miRNAs of interest as they are statistically significant which are labelled. Serum exosomes, HC, n=23 and AD, n=23. BDEs, HC, n=7 and PD, n=7.

To visualise the direction of expression between the two sample types (brain derived exosomes and serum exosomes of AD subjects), the fold changes between AD V's HC observed in brain derived exosomes and serum exosomes were plotted in FIG. 25. While many miRNAs were found to display unchanged expression in both BDEs and serum exosomes of AD samples compared to controls, other miRNAs were found to be changed in only one sample type and not the other. There were 68 miRNAs that displayed an inverse expression (negative correlation) (FIG. 25, white datapoints) between the two sample types of which two were significantly differentially expressed in serum exosomes (hsa-miR-1306-5p (SEQ ID NO: 22) and hsa-miR-342-3p (SEQ ID NO: 79), FIG. 25). While, 22 miRNAs were found to be downregulated in both serum exosomes and BDE (FIG. 25, lower left quadrant). From FIG. 25, 50 miRNAs were found to be upregulated in both serum exosomes and BDEs (FIG. 25, top right quadrant) in which two were statistically significant.

This data indicates that miRNA deregulated in serum exosomes that are also deregulated in brain derived exosomes can be used to diagnose a disease state of a human subject. For example, miRNA deregulated in serum exosomes from patients with dementia can be used in combination with miRNA deregulated in serum exosomes of patients with AD (miRNA deregulated in serum exosomes; e.g., hsa-miR-143-3p (SEQ ID NO: 73), and hsa-miR-30e-5p (SEQ ID NO: 78)).

Example 14: Performance of AD Associated Biomarkers Using Association Rule Mining Association Rule Mining was found to provide the highest AUC that could predict PET− patients from PET+ patients. Association Rule Mining can classify rules by any attribute with more than one feature at the same time which can provide a combination of features in 1 rule. The miRNAs associated with AD found in serum exosomes and brain derived exosomes during the discovery study, were used to screen samples in a second cohort of samples. The Delta CT values of each miRNA across all samples were normalised into quartiles whereby Q1=lower expression and Q4=higher expression. Age at baseline (0 months=first assessment) was also normalised into quartiles whereby Q1 is the youngest group and Q4 is the oldest group. This dataset was used for Association Rule Mining which consisted of 310 participants (PET−, n=171 and PET+, n=139) from the Australian Imaging, Biomarkers and Lifestyle Study of Ageing. All individuals included were assessed for full blood pathology testing (Melbourne Health and PathWest Laboratory Medicine), apolipoprotein ε4 (ApoE ε4) genotyping and assessment of cognitive functions (mini-mental state examination, MMSE) at the time of collection. All patients had Amyloid-PET neuroimaging data available for assessment of cerebral Aβ accumulation. The higher the present of cerebral Aβ accumulation as expressed as 11C-PiB standardised uptake value ratio (SUVR), the more likely the participant was diagnosed with AD. The following rules were associated with PET− (healthy) or PET+ (probable AD) patients as indicated below in Table 12. Identifying miRNA expression features that are associated with a probable PET+ brain image may assist with the diagnosis of AD and minimise healthcare costs, such as PET imaging, for patients and hospitals. The overall accuracy was 100% and the number of correct predictions is displayed in Table 13.

TABLE 12A

Association rules for the prediction of PET− or PET+ patients

| Rule | Class | Coverage (%) | Confidence (%) | Number Rule Applied | | Sex | miR-101-3p | miR-106a-5p | miR-106b-5p | miR-1306-5p | miR-143-3p | miR-15a-5p |
|---|---|---|---|---|---|---|---|---|---|---|---|---|
| 1 | PET+ | 4.516 | 100 | 14 | Q4 | M | | Q1 | | | | |
| 2 | PET− | 4.194 | 100 | 13 | Q1 | M | | | | | | |
| 3 | PET+ | 4.194 | 100 | 13 | Q4 | M | | | | | | |
| 4 | PET− | 4.194 | 100 | 13 | | M | | | | Q2 | Q2 | |
| 5 | PET− | 3.871 | 100 | 12 | Q1 | M | | | | | | |
| 6 | PET− | 3.871 | 100 | 12 | Q2 | | | | | | | |
| 7 | PET+ | 3.871 | 100 | 12 | Q4 | M | | | | Q1 | | |
| 8 | PET+ | 3.871 | 100 | 12 | Q4 | M | | | | | | Q1 |
| 9 | PET+ | 3.871 | 100 | 12 | Q4 | M | | | | | | |
| 10 | PET− | 3.548 | 100 | 11 | Q1 | M | Q4 | | | | | |
| 11 | PET− | 3.548 | 100 | 11 | Q1 | M | | Q2 | | | | |
| 12 | PET− | 3.548 | 100 | 11 | Q2 | | | | | | | |
| 13 | PET+ | 3.548 | 100 | 11 | Q4 | | | Q1 | | | | |
| 14 | PET+ | 3.548 | 100 | 11 | Q4 | | | | | | | Q1 |
| 15 | PET− | 3.548 | 100 | 11 | | | Q2 | | Q1 | Q2 | | |
| 16 | PET− | 3.548 | 100 | 11 | | M | | Q2 | Q1 | | | |
| 17 | PET− | 3.226 | 100 | 10 | Q1 | | | | | Q3 | | Q3 |
| 18 | PET− | 3.226 | 100 | 10 | Q1 | | | | | | Q4 | Q3 |
| 19 | PET− | 3.226 | 100 | 10 | Q2 | | Q4 | | | | | |

TABLE 12A-continued

Association rules for the prediction of PET− or PET+ patients

| Rule | Class | Coverage (%) | Confidence (%) | Number Rule Applied | | Sex | miR-101-3p | miR-106a-5p | miR-106b-5p | miR-1306-5p | miR-143-3p | miR-15a-5p |
|---|---|---|---|---|---|---|---|---|---|---|---|---|
| 20 | PET+ | 3.226 | 100 | 10 | Q4 | | | Q1 | | | | |
| 21 | PET+ | 3.226 | 100 | 10 | Q4 | | | | | | | |
| 22 | PET+ | 3.226 | 100 | 10 | Q4 | M | | | | | | |
| 23 | PET+ | 3.226 | 100 | 10 | Q4 | | | | | | | |
| 24 | PET− | 3.226 | 100 | 10 | | | | | | Q2 | Q2 | Q2 |
| 25 | PET− | 2.903 | 100 | 9 | Q1 | M | | | | | | |
| 26 | PET− | 2.903 | 100 | 9 | Q2 | | | Q4 | | | | |
| 27 | PET− | 2.903 | 100 | 9 | Q2 | M | | | | Q2 | | |
| 28 | PET− | 2.903 | 100 | 9 | Q2 | | | | | | | Q2 |
| 29 | PET+ | 2.903 | 100 | 9 | Q4 | | | Q2 | | | | |
| 30 | PET− | 2.903 | 100 | 9 | | M | | | | Q2 | | |
| 31 | PET− | 2.903 | 100 | 9 | | M | | Q4 | | | | Q4 |
| 32 | PET− | 2.581 | 100 | 8 | Q2 | M | Q2 | | | | | |
| 33 | PET− | 2.581 | 100 | 8 | Q2 | | | | Q2 | | | |
| 34 | PET− | 2.581 | 100 | 8 | Q2 | | | | | | | Q2 |
| 35 | PET+ | 2.581 | 100 | 8 | Q4 | M | Q3 | | | | | |
| 36 | PET+ | 2.581 | 100 | 8 | Q4 | | | | Q1 | | | Q1 |
| 37 | PET+ | 2.581 | 100 | 8 | Q4 | | | | | | | |
| 38 | PET− | 2.581 | 100 | 8 | | | Q4 | Q2 | | | | |
| 39 | PET− | 2.581 | 100 | 8 | | F | Q4 | | Q2 | | | |
| 40 | PET− | 2.581 | 100 | 8 | | | Q1 | Q2 | Q1 | | | |
| 41 | PET− | 2.581 | 100 | 8 | | | | Q4 | | | | Q4 |
| 42 | PET+ | 2.581 | 100 | 8 | | F | | Q1 | | | | |
| 43 | PET− | 2.581 | 100 | 8 | | | | | Q2 | Q3 | Q4 | |
| 44 | PET+ | 2.581 | 100 | 8 | | | | | | | Q3 | |
| 45 | PET− | 2.581 | 100 | 8 | | | | | | | | Q2 |
| 46 | PET+ | 2.581 | 100 | 8 | | | | | | | | Q1 |
| 47 | PET− | 2.581 | 100 | 8 | | M | | | | | | |
| 48 | PET+ | 2.581 | 100 | 8 | | F | Q3 | | Q4 | | | |
| 49 | PET+ | 2.581 | 100 | 8 | | F | | | Q3 | | Q3 | |
| 50 | PET− | 2.258 | 100 | 7 | Q1 | | Q1 | | | | Q2 | |
| 51 | PET− | 2.258 | 100 | 7 | Q1 | | | Q2 | | Q3 | | |
| 52 | PET− | 2.258 | 100 | 7 | Q2 | | | Q3 | Q2 | | | |
| 53 | PET− | 2.258 | 100 | 7 | Q2 | | | Q2 | | | | |
| 54 | PET− | 2.258 | 100 | 7 | Q2 | | | | Q3 | | | |
| 55 | PET− | 2.258 | 100 | 7 | Q2 | | | | | | | |
| 56 | PET− | 2.258 | 100 | 7 | Q3 | | | | Q1 | | | |
| 57 | PET− | 2.258 | 100 | 7 | | | Q4 | | | | Q4 | Q3 |
| 58 | PET− | 2.258 | 100 | 7 | | M | Q4 | | | | | |
| 59 | PET− | 2.258 | 100 | 7 | | F | Q3 | | | | | |
| 60 | PET− | 2.258 | 100 | 7 | | M | Q2 | | | | | |
| 61 | PET− | 2.258 | 100 | 7 | | | | Q4 | | | Q1 | |
| 62 | PET− | 2.258 | 100 | 7 | | | | Q2 | | Q2 | | |
| 63 | PET+ | 2.258 | 100 | 7 | | | | | Q3 | | | |
| 64 | PET+ | 2.258 | 100 | 7 | | | | | Q3 | | | |
| 65 | PET+ | 2.258 | 100 | 7 | | F | | | Q3 | | | |
| 66 | PET− | 2.258 | 100 | 7 | | | | | Q1 | | Q1 | |
| 67 | PET+ | 2.258 | 100 | 7 | | F | | | | | Q2 | |
| 68 | PET− | 2.258 | 100 | 7 | | | | | | | Q1 | |
| 69 | PET− | 2.258 | 100 | 7 | | | | | | | | Q2 |
| 70 | PET− | 2.258 | 100 | 7 | | M | | | | | | Q1 |
| 71 | PET+ | 2.258 | 100 | 7 | | | | | | | | |
| 72 | PET+ | 2.258 | 100 | 7 | | M | | Q1 | | Q1 | | |
| 73 | PET+ | 2.258 | 100 | 7 | | | | | Q4 | | | |
| 74 | PET+ | 2.258 | 100 | 7 | | F | | | Q4 | | | |
| 75 | PET− | 1.935 | 100 | 6 | Q1 | | | | | | Q4 | |
| 76 | PET− | 1.935 | 100 | 6 | Q2 | | Q4 | | Q1 | | | |
| 77 | PET− | 1.935 | 100 | 6 | Q2 | | Q4 | | | | | |
| 78 | PET− | 1.935 | 100 | 6 | Q2 | | Q2 | | | | | |
| 79 | PET− | 1.935 | 100 | 6 | Q2 | | | Q3 | | | | |
| 80 | PET− | 1.935 | 100 | 6 | Q2 | | | | Q1 | | Q2 | |
| 81 | PET+ | 1.935 | 100 | 6 | Q4 | | Q1 | | | | | |
| 82 | PET− | 1.935 | 100 | 6 | | | Q3 | | Q3 | | | |
| 83 | PET+ | 1.935 | 100 | 6 | | | Q3 | | | Q1 | | |
| 84 | PET+ | 1.935 | 100 | 6 | | F | Q1 | | Q3 | | | |
| 85 | PET+ | 1.935 | 100 | 6 | | | | Q3 | Q3 | | Q3 | |
| 86 | PET− | 1.935 | 100 | 6 | | | | | Q2 | | | |
| 87 | PET− | 1.935 | 100 | 6 | | | | | | Q3 | | |
| 88 | PET− | 1.935 | 100 | 6 | | | | | | Q2 | Q3 | |
| 89 | PET+ | 1.935 | 100 | 6 | | | | | | | Q3 | |
| 90 | PET+ | 1.935 | 100 | 6 | Q1 | | | | Q3 | | Q3 | |
| 91 | PET+ | 1.935 | 100 | 6 | Q1 | F | | | | | | |
| 92 | PET− | 1.935 | 100 | 6 | Q3 | M | | | | Q2 | | |
| 93 | PET− | 1.935 | 100 | 6 | | F | Q4 | | | | | Q4 |

TABLE 12A-continued

Association rules for the prediction of PET− or PET+ patients

| Rule | Class | Coverage (%) | Confidence (%) | Number Rule Applied | | Sex | miR-101-3p | miR-106a-5p | miR-106b-5p | miR-1306-5p | miR-143-3p | miR-15a-5p |
|---|---|---|---|---|---|---|---|---|---|---|---|---|
| 94 | PET− | 1.935 | 100 | 6 | | M | | Q3 | Q2 | | | |
| 95 | PET+ | 1.935 | 100 | 6 | | F | | | Q4 | Q2 | | |
| 96 | PET+ | 1.613 | 100 | 5 | Q1 | | Q1 | | Q3 | | | |
| 97 | PET− | 1.613 | 100 | 5 | Q1 | | | | Q1 | | | |
| 98 | PET+ | 1.613 | 100 | 5 | Q1 | F | | | | | | Q1 |
| 99 | PET− | 1.613 | 100 | 5 | Q2 | | Q2 | Q1 | | | | |
| 100 | PET− | 1.613 | 100 | 5 | Q2 | | | | Q4 | Q1 | | |
| 101 | PET− | 1.613 | 100 | 5 | Q3 | M | | | | | | |
| 102 | PET+ | 1.613 | 100 | 5 | Q4 | | Q1 | | | | | |
| 103 | PET+ | 1.613 | 100 | 5 | Q4 | | | Q2 | | | | |
| 104 | PET+ | 1.613 | 100 | 5 | Q4 | | | | Q3 | | | |
| 105 | PET+ | 1.613 | 100 | 5 | Q4 | | | | | | | |
| 106 | PET+ | 1.613 | 100 | 5 | | | Q4 | | | | | |
| 107 | PET+ | 1.613 | 100 | 5 | | | Q3 | Q2 | | Q4 | | |
| 108 | PET+ | 1.613 | 100 | 5 | | | Q3 | Q2 | | Q1 | | |
| 109 | PET+ | 1.613 | 100 | 5 | | | Q2 | | Q2 | Q1 | | |
| 110 | PET− | 1.613 | 100 | 5 | | | Q1 | Q2 | | | | Q1 |
| 111 | PET− | 1.613 | 100 | 5 | | | Q1 | Q2 | | | | |
| 112 | PET+ | 1.613 | 100 | 5 | | | Q1 | | | | Q3 | |
| 113 | PET− | 1.613 | 100 | 5 | | | Q1 | | | | | |
| 114 | PET+ | 1.613 | 100 | 5 | | | Q1 | | | | | |
| 115 | PET− | 1.613 | 100 | 5 | | F | | | Q4 | | | |
| 116 | PET− | 1.613 | 100 | 5 | | | | | Q4 | | | |
| 117 | PET− | 1.613 | 100 | 5 | | | | | | Q3 | | |
| 118 | PET+ | 1.613 | 100 | 5 | | | | | | Q2 | | |
| 119 | PET+ | 1.613 | 100 | 5 | | | | | | | Q4 | |
| 120 | PET+ | 1.613 | 100 | 5 | | | | | | | Q3 | |
| 121 | PET+ | 1.613 | 100 | 5 | | | | | | | Q2 | |
| 122 | PET+ | 1.613 | 100 | 5 | | | | | | | | Q2 |
| 123 | PET− | 1.613 | 100 | 5 | | | | | | | | Q2 |
| 124 | PET+ | 1.613 | 100 | 5 | | | | | | | | |
| 125 | PET+ | 1.613 | 100 | 5 | | | | | | | | |
| 126 | PET+ | 1.613 | 100 | 5 | Q1 | | | | | | | |
| 127 | PET+ | 1.613 | 100 | 5 | Q4 | | Q4 | | | Q4 | | Q4 |
| 128 | PET+ | 1.613 | 100 | 5 | | F | Q3 | Q2 | | | | |
| 129 | PET− | 1.613 | 100 | 5 | | | Q3 | | Q3 | | Q4 | |
| 130 | PET+ | 1.613 | 100 | 5 | | | Q2 | | | Q1 | | Q1 |
| 131 | PET+ | 1.613 | 100 | 5 | | | Q1 | | | Q1 | | Q1 |
| 132 | PET+ | 1.613 | 100 | 5 | | F | | Q4 | | | | |
| 133 | PET+ | 1.613 | 100 | 5 | | F | | Q3 | | Q2 | | |
| 134 | PET− | 1.613 | 100 | 5 | | F | | | Q4 | Q1 | | |
| 135 | PET− | 1.613 | 100 | 5 | | M | | | Q3 | | Q4 | |
| 136 | PET− | 1.29 | 100 | 4 | | | | Q4 | | Q1 | | |
| 137 | PET− | 1.29 | 100 | 4 | Q1 | | | | Q4 | | | |
| 138 | PET+ | 1.29 | 100 | 4 | Q1 | | | | | | | Q2 |
| 139 | PET+ | 1.29 | 100 | 4 | Q3 | | | | | Q4 | | Q3 |
| 140 | PET− | 1.29 | 100 | 4 | | | | | Q4 | | | Q1 |
| 141 | PET+ | 1.29 | 100 | 4 | | | | | | | | Q3 |
| 142 | PET+ | 1.29 | 100 | 4 | | | | | | | | Q1 |
| 143 | PET+ | 1.29 | 100 | 4 | Q3 | | | | | | Q4 | |
| 144 | PET+ | 1.29 | 100 | 4 | Q3 | F | | | | | | Q3 |
| 145 | PET+ | 0.968 | 100 | 3 | Q3 | | | Q1 | | | | |
| 146 | PET+ | 0.968 | 100 | 3 | | | | Q1 | Q1 | | | Q1 |

TABLE 12B

Association rules for the prediction of PET− or PET+ patients

| Rule | Class | Coverage (%) | Confidence (%) | Number Rule Applied | | Sex | miR-15b-3p | miR-20a-5p | miR-223-5p | miR-30e-5p | miR-335-5p | miR-342-3p |
|---|---|---|---|---|---|---|---|---|---|---|---|---|
| 1 | PET+ | 4.516 | 100 | 14 | Q4 | M | | | | | | |
| 2 | PET− | 4.194 | 100 | 13 | Q1 | M | Q4 | | | | | |
| 3 | PET+ | 4.194 | 100 | 13 | Q4 | M | | | Q1 | | | |
| 4 | PET− | 4.194 | 100 | 13 | | M | | | | | | |
| 5 | PET− | 3.871 | 100 | 12 | Q1 | M | | Q1 | | | | |
| 6 | PET− | 3.871 | 100 | 12 | Q2 | | | | Q3 | | | Q2 |
| 7 | PET+ | 3.871 | 100 | 12 | Q4 | M | | | | | | |
| 8 | PET+ | 3.871 | 100 | 12 | Q4 | M | | | | | | |
| 9 | PET+ | 3.871 | 100 | 12 | Q4 | M | | | | | | Q1 |

TABLE 12B-continued

Association rules for the prediction of PET− or PET+ patients

| Rule | Class | Coverage (%) | Confidence (%) | Number Rule Applied | | Sex | miR-15b-3p | miR-20a-5p | miR-223-5p | miR-30e-5p | miR-335-5p | miR-342-3p |
|---|---|---|---|---|---|---|---|---|---|---|---|---|
| 10 | PET− | 3.548 | 100 | 11 | Q1 | M | | | | | | |
| 11 | PET− | 3.548 | 100 | 11 | Q1 | M | | | | | | |
| 12 | PET− | 3.548 | 100 | 11 | Q2 | | Q2 | | Q3 | | | |
| 13 | PET+ | 3.548 | 100 | 11 | Q4 | | | | | | Q1 | |
| 14 | PET+ | 3.548 | 100 | 11 | Q4 | | | | | | | Q1 |
| 15 | PET− | 3.548 | 100 | 11 | | | | | | | | |
| 16 | PET− | 3.548 | 100 | 11 | | M | | Q2 | | | | |
| 17 | PET− | 3.226 | 100 | 10 | Q1 | | | | | | | |
| 18 | PET− | 3.226 | 100 | 10 | Q1 | | | | | | | |
| 19 | PET− | 3.226 | 100 | 10 | Q2 | | Q2 | | | | | |
| 20 | PET+ | 3.226 | 100 | 10 | Q4 | | Q1 | | | | | |
| 21 | PET+ | 3.226 | 100 | 10 | Q4 | | Q1 | | | | | Q1 |
| 22 | PET+ | 3.226 | 100 | 10 | Q4 | M | | | | Q1 | | |
| 23 | PET+ | 3.226 | 100 | 10 | Q4 | | | | | | Q1 | Q1 |
| 24 | PET− | 3.226 | 100 | 10 | | | | | | | | |
| 25 | PET− | 2.903 | 100 | 9 | Q1 | M | | | | | | Q4 |
| 26 | PET− | 2.903 | 100 | 9 | Q2 | | Q2 | | | | | |
| 27 | PET− | 2.903 | 100 | 9 | Q2 | M | | | | | | |
| 28 | PET− | 2.903 | 100 | 9 | Q2 | | | | Q1 | | | |
| 29 | PET+ | 2.903 | 100 | 9 | Q4 | | | | | | | Q1 |
| 30 | PET− | 2.903 | 100 | 9 | | M | | | | | | Q2 |
| 31 | PET− | 2.903 | 100 | 9 | | M | | | Q4 | | | |
| 32 | PET− | 2.581 | 100 | 8 | Q2 | M | | | | | | |
| 33 | PET− | 2.581 | 100 | 8 | Q2 | | | | Q3 | | | |
| 34 | PET− | 2.581 | 100 | 8 | Q2 | | | | | | | Q2 |
| 35 | PET+ | 2.581 | 100 | 8 | Q4 | M | | | | | | |
| 36 | PET+ | 2.581 | 100 | 8 | Q4 | | | | | | | |
| 37 | PET+ | 2.581 | 100 | 8 | Q4 | | | Q1 | | Q4 | | |
| 38 | PET− | 2.581 | 100 | 8 | | | | Q2 | | | | |
| 39 | PET− | 2.581 | 100 | 8 | | F | | | | | | |
| 40 | PET− | 2.581 | 100 | 8 | | | | | | | | |
| 41 | PET− | 2.581 | 100 | 8 | | | | Q3 | | | | |
| 42 | PET+ | 2.581 | 100 | 8 | | F | | | | Q1 | | |
| 43 | PET− | 2.581 | 100 | 8 | | | | | | | | |
| 44 | PET+ | 2.581 | 100 | 8 | | | | | | Q4 | Q4 | |
| 45 | PET− | 2.581 | 100 | 8 | | | | Q2 | | | | Q2 |
| 46 | PET+ | 2.581 | 100 | 8 | | | Q3 | | | Q1 | | |
| 47 | PET− | 2.581 | 100 | 8 | | M | | Q2 | | Q3 | | |
| 48 | PET+ | 2.581 | 100 | 8 | | F | | | | | | Q4 |
| 49 | PET+ | 2.581 | 100 | 8 | | F | Q3 | | | | | |
| 50 | PET− | 2.258 | 100 | 7 | Q1 | | | | | | | |
| 51 | PET− | 2.258 | 100 | 7 | Q1 | | | | | | | |
| 52 | PET− | 2.258 | 100 | 7 | Q2 | | | | | | | |
| 53 | PET− | 2.258 | 100 | 7 | Q2 | | | | | | | Q2 |
| 54 | PET− | 2.258 | 100 | 7 | Q2 | | | | | | | Q4 |
| 55 | PET− | 2.258 | 100 | 7 | Q2 | | | Q3 | Q4 | | | |
| 56 | PET− | 2.258 | 100 | 7 | Q3 | | | | Q2 | | | |
| 57 | PET− | 2.258 | 100 | 7 | | | | | | | | |
| 58 | PET− | 2.258 | 100 | 7 | | M | | | | | Q2 | |
| 59 | PET− | 2.258 | 100 | 7 | | F | | | | | | Q2 |
| 60 | PET− | 2.258 | 100 | 7 | | M | | | | Q3 | | |
| 61 | PET− | 2.258 | 100 | 7 | | | | Q3 | | | | |
| 62 | PET− | 2.258 | 100 | 7 | | | | | Q3 | | | |
| 63 | PET+ | 2.258 | 100 | 7 | | | Q3 | | | Q1 | | |
| 64 | PET+ | 2.258 | 100 | 7 | | | Q3 | | | | Q1 | |
| 65 | PET+ | 2.258 | 100 | 7 | | F | | | | | Q1 | |
| 66 | PET− | 2.258 | 100 | 7 | | | | | | Q2 | | |
| 67 | PET+ | 2.258 | 100 | 7 | | F | | | Q2 | | | |
| 68 | PET− | 2.258 | 100 | 7 | | | | | | Q1 | Q3 | |
| 69 | PET− | 2.258 | 100 | 7 | | | | Q2 | | Q4 | | |
| 70 | PET− | 2.258 | 100 | 7 | | M | | | | Q2 | | |
| 71 | PET+ | 2.258 | 100 | 7 | | | | Q1 | | Q4 | Q4 | |
| 72 | PET+ | 2.258 | 100 | 7 | | M | | | | | | Q2 |
| 73 | PET+ | 2.258 | 100 | 7 | | | Q4 | | Q4 | Q4 | | |
| 74 | PET+ | 2.258 | 100 | 7 | | F | | | Q2 | | | Q4 |
| 75 | PET− | 1.935 | 100 | 6 | Q1 | | | | | Q2 | | |
| 76 | PET− | 1.935 | 100 | 6 | Q2 | | | | | | | |
| 77 | PET− | 1.935 | 100 | 6 | Q2 | | | | | | Q3 | |
| 78 | PET− | 1.935 | 100 | 6 | Q2 | | | | | | | Q4 |
| 79 | PET− | 1.935 | 100 | 6 | Q2 | | | | | | | Q3 |
| 80 | PET− | 1.935 | 100 | 6 | Q2 | | | | | | | |
| 81 | PET+ | 1.935 | 100 | 6 | Q4 | | | | Q3 | | | |
| 82 | PET− | 1.935 | 100 | 6 | | | | | | | | Q4 |
| 83 | PET+ | 1.935 | 100 | 6 | | | | | | | Q1 | |

TABLE 12B-continued

Association rules for the prediction of PET− or PET+ patients

| Rule | Class | Coverage (%) | Confidence (%) | Number Rule Applied | | Sex | miR-15b-3p | miR-20a-5p | miR-223-5p | miR-30e-5p | miR-335-5p | miR-342-3p |
|---|---|---|---|---|---|---|---|---|---|---|---|---|
| 84 | PET+ | 1.935 | 100 | 6 | | F | | | | | | |
| 85 | PET+ | 1.935 | 100 | 6 | | | | | | | | |
| 86 | PET− | 1.935 | 100 | 6 | | | | Q4 | | | Q4 | |
| 87 | PET− | 1.935 | 100 | 6 | | | | | | | Q1 | Q2 |
| 88 | PET− | 1.935 | 100 | 6 | | | Q1 | | | | | |
| 89 | PET+ | 1.935 | 100 | 6 | | | | Q3 | | | Q3 | |
| 90 | PET+ | 1.935 | 100 | 6 | Q1 | | | | | | | Q3 |
| 91 | PET+ | 1.935 | 100 | 6 | Q1 | F | | | Q4 | Q4 | | |
| 92 | PET− | 1.935 | 100 | 6 | Q3 | M | | | Q2 | | | |
| 93 | PET− | 1.935 | 100 | 6 | | F | | Q3 | | | | |
| 94 | PET− | 1.935 | 100 | 6 | | M | Q2 | | | | | |
| 95 | PET+ | 1.935 | 100 | 6 | | F | Q4 | | | | | |
| 96 | PET+ | 1.613 | 100 | 5 | Q1 | | | | | | | |
| 97 | PET− | 1.613 | 100 | 5 | Q1 | | | | Q2 | | | |
| 98 | PET+ | 1.613 | 100 | 5 | Q1 | F | | | | | | |
| 99 | PET− | 1.613 | 100 | 5 | Q2 | | | | | | | |
| 100 | PET− | 1.613 | 100 | 5 | Q2 | | | | | | | |
| 101 | PET− | 1.613 | 100 | 5 | Q3 | M | | | | | | Q3 |
| 102 | PET+ | 1.613 | 100 | 5 | Q4 | | | | Q2 | | | |
| 103 | PET+ | 1.613 | 100 | 5 | Q4 | | Q2 | | | | | |
| 104 | PET+ | 1.613 | 100 | 5 | Q4 | | | | Q3 | | | |
| 105 | PET+ | 1.613 | 100 | 5 | Q4 | | Q4 | | | | Q2 | |
| 106 | PET+ | 1.613 | 100 | 5 | | | Q3 | | | | | Q3 |
| 107 | PET+ | 1.613 | 100 | 5 | | | | | | | | |
| 108 | PET+ | 1.613 | 100 | 5 | | | | | | | | |
| 109 | PET+ | 1.613 | 100 | 5 | | | | | | | | |
| 110 | PET− | 1.613 | 100 | 5 | | | | | | | | |
| 111 | PET− | 1.613 | 100 | 5 | | | | Q1 | | | | |
| 112 | PET+ | 1.613 | 100 | 5 | | | | Q1 | | | | |
| 113 | PET− | 1.613 | 100 | 5 | | | Q2 | | | | | Q1 |
| 114 | PET+ | 1.613 | 100 | 5 | | | | | | | Q4 | Q2 |
| 115 | PET− | 1.613 | 100 | 5 | | F | Q2 | | | | | |
| 116 | PET− | 1.613 | 100 | 5 | | | | | Q3 | | Q3 | |
| 117 | PET− | 1.613 | 100 | 5 | | | | | | | Q4 | Q3 |
| 118 | PET+ | 1.613 | 100 | 5 | | | | | Q4 | | Q1 | |
| 119 | PET+ | 1.613 | 100 | 5 | | | | | Q4 | | | Q1 |
| 120 | PET+ | 1.613 | 100 | 5 | | | | Q1 | | | Q4 | |
| 121 | PET+ | 1.613 | 100 | 5 | | | Q4 | | | Q4 | | |
| 122 | PET+ | 1.613 | 100 | 5 | | | | Q3 | | Q3 | | |
| 123 | PET− | 1.613 | 100 | 5 | | | | | Q4 | | | Q3 |
| 124 | PET+ | 1.613 | 100 | 5 | | | Q3 | | Q3 | | Q2 | |
| 125 | PET+ | 1.613 | 100 | 5 | | | | Q1 | Q3 | | | Q1 |
| 126 | PET+ | 1.613 | 100 | 5 | Q1 | | Q4 | | Q2 | | | Q4 |
| 127 | PET+ | 1.613 | 100 | 5 | Q4 | | | | | | | |
| 128 | PET+ | 1.613 | 100 | 5 | | F | | | | | | Q1 |
| 129 | PET− | 1.613 | 100 | 5 | | | | | | | Q4 | |
| 130 | PET+ | 1.613 | 100 | 5 | | | | Q2 | | | | |
| 131 | PET+ | 1.613 | 100 | 5 | | | | | | Q4 | | |
| 132 | PET+ | 1.613 | 100 | 5 | | F | Q3 | | | | | Q3 |
| 133 | PET+ | 1.613 | 100 | 5 | | F | | | Q2 | | | |
| 134 | PET− | 1.613 | 100 | 5 | | F | | | | | Q3 | |
| 135 | PET− | 1.613 | 100 | 5 | | M | | | | | Q4 | |
| 136 | PET− | 1.29 | 100 | 4 | | | | | | | | |
| 137 | PET− | 1.29 | 100 | 4 | Q1 | | | | Q3 | | | |
| 138 | PET+ | 1.29 | 100 | 4 | Q1 | | | | | | Q4 | |
| 139 | PET+ | 1.29 | 100 | 4 | Q3 | | | | | | | |
| 140 | PET− | 1.29 | 100 | 4 | | | | | | Q3 | | |
| 141 | PET+ | 1.29 | 100 | 4 | | | | Q2 | Q1 | | | |
| 142 | PET+ | 1.29 | 100 | 4 | | | Q1 | Q3 | | | | |
| 143 | PET+ | 1.29 | 100 | 4 | Q3 | | | Q3 | Q4 | | | |
| 144 | PET+ | 1.29 | 100 | 4 | Q3 | F | | | | | Q3 | |
| 145 | PET+ | 0.968 | 100 | 3 | Q3 | | Q1 | | | | Q1 | |
| 146 | PET+ | 0.968 | 100 | 3 | | | | Q2 | | | | |

TABLE 13

| Confusion Matrix On Training: | | |
|---|---|---|
| | Classified as | |
| Predicted as | PET− | PET+ |
| PET− | 171 | 0 |
| PET+ | 0 | 139 |

AUC: 100%

The invention claimed is:

1. A method of treating Parkinson's disease or a predisposition to Parkinson's disease in a human subject, said method comprising the steps of:

a) measuring the level of expression of each member of a panel of small non-coding RNAs, each member comprising a nucleotide sequence selected from the group consisting of SEQ ID Nos: 1, 3, 5-10, 13, and 14, in a sample from the subject, wherein the sample comprises exosomes, wherein the exosomes comprise the small non-encoding RNAs, and wherein the sample is blood, serum, or plasma;

b) comparing the level of expression of each of the small non-coding RNAs to a reference level of expression of the small non-coding RNAs, wherein a decreased level of expression of the small non-coding RNAs compared to the reference level is found and is indicative of Parkinson's disease or a predisposition to Parkinson's disease, wherein the reference level of expression is based on levels in healthy individuals; and c) treating the Parkinson's disease or the predisposition to Parkinson's disease by administering to the subject an anti-Parkinson's disease therapy selected from the group consisting of levodopa, COMT inhibitors, dopamine agonists, MAO-B inhibitors, and surgery.

2. The method according to claim 1, wherein the reference level of expression of the small non-coding RNA is a threshold level of expression, wherein the threshold level of expression is a cut-off value.

3. The method of claim 1, wherein the small non-coding RNAs are microRNA (miRNA).

4. The method of claim 1, further comprising a psychological, behavioural, physiological and/or genetic assessment of the subject.

5. The method according to claim 1, further comprising measuring the level of at least one small non-coding RNAs selected from the group consisting of SEQ ID NO: 22, SEQ ID NO: 79, SEQ ID NO: 71, SEQ ID NO: 72, ID NO: 73, SEQ ID NO: 74, SEQ ID NO: 75, SEQ ID NO: 61, SEQ ID NO: 76, SEQ ID NO: 77, and SEQ ID NO: 78, in a sample from the subject, and wherein an increased or decreased level of expression of at least one or non-coding RNA selected from the group consisting of SEQ ID NO: 22, SEQ ID NO: 79, SEQ ID NO: 71, SEQ ID NO: 72, ID NO: 73, SEQ ID NO: 74, SEQ ID NO: 75, SEQ ID NO: 61, SEQ ID NO: 76, SEQ ID NO: 77, and SEQ ID NO: 78, compared to the reference level(s) is indicative of Alzheimer's Disease or a predisposition to Alzheimer's Disease.

* * * * *

SEQUENCE LISTING

<160> NUMBER OF SEQ ID NOS: 79

<210> SEQ ID NO 1
<211> LENGTH: 21
<212> TYPE: RNA
<213> ORGANISM: Homo sapiens

<400> SEQUENCE: 1
agcuacaucu ggcuacuggg u 21

<210> SEQ ID NO 2
<211> LENGTH: 22
<212> TYPE: RNA
<213> ORGANISM: Homo sapiens

<400> SEQUENCE: 2
uguaaacauc cucgacugga ag 22

<210> SEQ ID NO 3
<211> LENGTH: 22
<212> TYPE: RNA
<213> ORGANISM: Homo sapiens

<400> SEQUENCE: 3
uggaguguga caaugguguu ug 22

<210> SEQ ID NO 4
<211> LENGTH: 22
<212> TYPE: RNA
<213> ORGANISM: Homo sapiens

<400> SEQUENCE: 4
ucccugagac ccuaacuugu ga 22

<210> SEQ ID NO 5
<211> LENGTH: 22
<212> TYPE: RNA
<213> ORGANISM: Homo sapiens

<400> SEQUENCE: 5
uuuggucccc uucaaccagc ug 22

<210> SEQ ID NO 6
<211> LENGTH: 22
<212> TYPE: RNA
<213> ORGANISM: Homo sapiens

<400> SEQUENCE: 6
ugagaacuga auuccauagg cu 22

<210> SEQ ID NO 7
<211> LENGTH: 23
<212> TYPE: RNA

<213> ORGANISM: Homo sapiens

<400> SEQUENCE: 7
aacauucaac gcugucggug agu 23

<210> SEQ ID NO 8
<211> LENGTH: 22
<212> TYPE: RNA
<213> ORGANISM: Homo sapiens

<400> SEQUENCE: 8
uauggcacug guagaauuca cu 22

<210> SEQ ID NO 9
<211> LENGTH: 21
<212> TYPE: RNA
<213> ORGANISM: Homo sapiens

<400> SEQUENCE: 9
cugaccuaug aauugacagc c 21

<210> SEQ ID NO 10
<211> LENGTH: 22
<212> TYPE: RNA
<213> ORGANISM: Homo sapiens

<400> SEQUENCE: 10
ugggucuuug cgggcgagau ga 22

<210> SEQ ID NO 11
<211> LENGTH: 22
<212> TYPE: RNA
<213> ORGANISM: Homo sapiens

<400> SEQUENCE: 11
auaagacgag caaaaagcuu gu 22

<210> SEQ ID NO 12
<211> LENGTH: 22
<212> TYPE: RNA
<213> ORGANISM: Homo sapiens

<400> SEQUENCE: 12
acagcaggca cagacaggca gu 22

<210> SEQ ID NO 13
<211> LENGTH: 21
<212> TYPE: RNA
<213> ORGANISM: Homo sapiens

<400> SEQUENCE: 13
aggcaagaug cuggcauagc u 21

<210> SEQ ID NO 14
<211> LENGTH: 22
<212> TYPE: RNA
<213> ORGANISM: Homo sapiens

<400> SEQUENCE: 14 uggcagugue uuagcugguu gu 22

<210> SEQ ID NO 15
<211> LENGTH: 24

<212> TYPE: RNA
<213> ORGANISM: Homo sapiens

<400> SEQUENCE: 15
aacaacaaaa ucacuagucu ucca 24

<210> SEQ ID NO 16
<211> LENGTH: 22
<212> TYPE: RNA
<213> ORGANISM: Homo sapiens

<400> SEQUENCE: 16
uuuguucguu cggcucgcgu ga 22

<210> SEQ ID NO 17
<211> LENGTH: 22
<212> TYPE: RNA
<213> ORGANISM: Homo sapiens

<400> SEQUENCE: 17
acuggacuug gagucagaag gc 22

<210> SEQ ID NO 18
<211> LENGTH: 22
<212> TYPE: RNA
<213> ORGANISM: Homo sapiens

<400> SEQUENCE: 18
gugacaucac auauacggca gc 22

<210> SEQ ID NO 19
<211> LENGTH: 22
<212> TYPE: RNA
<213> ORGANISM: Homo sapiens

<400> SEQUENCE: 19
cgucaacacu ugcugguuuc cu 22

<210> SEQ ID NO 20
<211> LENGTH: 24
<212> TYPE: RNA
<213> ORGANISM: Homo sapiens

<400> SEQUENCE: 20
uggaagacua gugauuuugu uguu 24

<210> SEQ ID NO 21
<211> LENGTH: 22
<212> TYPE: RNA
<213> ORGANISM: Homo sapiens

<400> SEQUENCE: 21
ugagaccucu ggguucugag cu 22

<210> SEQ ID NO 22
<211> LENGTH: 22
<212> TYPE: RNA
<213> ORGANISM: Homo sapiens

<400> SEQUENCE: 22
ccaccucccc ugcaaacguc ca 22

<210> SEQ ID NO 23

<211> LENGTH: 23
<212> TYPE: RNA
<213> ORGANISM: Homo sapiens

<400> SEQUENCE: 23
cccaguguuc agacuaccug uuc 23

<210> SEQ ID NO 24
<211> LENGTH: 22
<212> TYPE: RNA
<213> ORGANISM: Homo sapiens

<400> SEQUENCE: 24
uucaaguaau ccaggauagg cu 22

<210> SEQ ID NO 25
<211> LENGTH: 23
<212> TYPE: RNA
<213> ORGANISM: Homo sapiens

<400> SEQUENCE: 25
ucccuguccu ccaggagcuc acg 23

<210> SEQ ID NO 26
<211> LENGTH: 21
<212> TYPE: RNA
<213> ORGANISM: Homo sapiens

<400> SEQUENCE: 26
acaggagugg gggugggaca u 21

<210> SEQ ID NO 27
<211> LENGTH: 21
<212> TYPE: RNA
<213> ORGANISM: Homo sapiens

<400> SEQUENCE: 27
augucccacc cccacuccug u 21

<210> SEQ ID NO 28
<211> LENGTH: 22
<212> TYPE: RNA
<213> ORGANISM: Homo sapiens

<400> SEQUENCE: 28
acuccagccc cacagccuca gc 22

<210> SEQ ID NO 29
<211> LENGTH: 23
<212> TYPE: RNA
<213> ORGANISM: Mus musculus

<400> SEQUENCE: 29
caccaccucc ccugcaaacg ucc 23

<210> SEQ ID NO 30
<211> LENGTH: 22
<212> TYPE: RNA
<213> ORGANISM: Mus musculus

<400> SEQUENCE: 30
cagugcaaug uuaaaagggc au 22

-continued

<210> SEQ ID NO 31
<211> LENGTH: 22
<212> TYPE: RNA
<213> ORGANISM: Mus musculus

<400> SEQUENCE: 31
ucagugcauc acagaacuuu gu 22

<210> SEQ ID NO 32
<211> LENGTH: 21
<212> TYPE: RNA
<213> ORGANISM: Mus musculus

<400> SEQUENCE: 32
uauugcacuu gucccggccu g 21

<210> SEQ ID NO 33
<211> LENGTH: 23
<212> TYPE: RNA
<213> ORGANISM: Mus musculus

<400> SEQUENCE: 33
uguaguguuu ccuacuuuau gga 23

<210> SEQ ID NO 34
<211> LENGTH: 22
<212> TYPE: RNA
<213> ORGANISM: Mus musculus

<400> SEQUENCE: 34
uagcagcaca ucaugguuua ca 22

<210> SEQ ID NO 35
<211> LENGTH: 23
<212> TYPE: RNA
<213> ORGANISM: Mus musculus

<400> SEQUENCE: 35
aacauucaac gcugucggug agu 23

<210> SEQ ID NO 36
<211> LENGTH: 22
<212> TYPE: RNA
<213> ORGANISM: Mus musculus

<400> SEQUENCE: 36
uggaauguaa agaaguaugu au 22

<210> SEQ ID NO 37
<211> LENGTH: 23
<212> TYPE: RNA
<213> ORGANISM: Mus musculus

<400> SEQUENCE: 37
cguguauuug acaagcugag uug 23

<210> SEQ ID NO 38
<211> LENGTH: 23
<212> TYPE: RNA
<213> ORGANISM: Mus musculus

<400> SEQUENCE: 38
agcucggucu gaggccccuc agu 23

<210> SEQ ID NO 39
<211> LENGTH: 22
<212> TYPE: RNA
<213> ORGANISM: Mus musculus

<400> SEQUENCE: 39
ugagaacuga auuccauggg uu 22

<210> SEQ ID NO 40
<211> LENGTH: 22
<212> TYPE: RNA
<213> ORGANISM: Mus musculus

<400> SEQUENCE: 40
uagcagcacg uaaauauugg cg 22

<210> SEQ ID NO 41
<211> LENGTH: 22
<212> TYPE: RNA
<213> ORGANISM: Mus musculus

<400> SEQUENCE: 41
uccuucauuc caccggaguc ug 22

<210> SEQ ID NO 42
<211> LENGTH: 23
<212> TYPE: RNA
<213> ORGANISM: Mus musculus

<400> SEQUENCE: 42
agcuacaucu ggcuacuggg ucu 23

<210> SEQ ID NO 43
<211> LENGTH: 23
<212> TYPE: RNA
<213> ORGANISM: Mus musculus

<400> SEQUENCE: 43
uguaguguuu ccuacuuuau gga 23

<210> SEQ ID NO 44
<211> LENGTH: 22
<212> TYPE: RNA
<213> ORGANISM: Mus musculus

<400> SEQUENCE: 44
uagcagcaca ucaugguuua ca 22

<210> SEQ ID NO 45
<211> LENGTH: 22
<212> TYPE: RNA
<213> ORGANISM: Mus musculus

<400> SEQUENCE: 45
ugagaacuga auuccauggg uu 22

<210> SEQ ID NO 46
<211> LENGTH: 22
<212> TYPE: RNA
<213> ORGANISM: Mus musculus

<400> SEQUENCE: 46
uagcagcacg uaaauauugg cg 22

<210> SEQ ID NO 47
<211> LENGTH: 22
<212> TYPE: RNA
<213> ORGANISM: Mus musculus

<400> SEQUENCE: 47
uccuucauuc caccggaguc ug 22

<210> SEQ ID NO 48
<211> LENGTH: 23
<212> TYPE: RNA
<213> ORGANISM: Mus musculus

<400> SEQUENCE: 48
agcuacaucu ggcuacuggg ucu 23

<210> SEQ ID NO 49
<211> LENGTH: 23
<212> TYPE: RNA
<213> ORGANISM: Mus musculus

<400> SEQUENCE: 49
uacccuguag aaccgaauuu gug 23

<210> SEQ ID NO 50
<211> LENGTH: 22
<212> TYPE: RNA
<213> ORGANISM: Mus musculus

<400> SEQUENCE: 50
uuuggucccc uucaaccagc ug 22

<210> SEQ ID NO 51
<211> LENGTH: 21
<212> TYPE: RNA
<213> ORGANISM: Mus musculus

<400> SEQUENCE: 51
cauaaaguag aaagcacuac u 21

<210> SEQ ID NO 52
<211> LENGTH: 22
<212> TYPE: RNA
<213> ORGANISM: Mus musculus

<400> SEQUENCE: 52
gugaaauguu uaggaccacu ag 22

<210> SEQ ID NO 53
<211> LENGTH: 21
<212> TYPE: RNA
<213> ORGANISM: Mus musculus

<400> SEQUENCE: 53
augaccuaug auuugacaga c 21

<210> SEQ ID NO 54
<211> LENGTH: 23
<212> TYPE: RNA
<213> ORGANISM: Homo sapiens

<400> SEQUENCE: 54
uacccuguag aaccgaauuu gug 23

<210> SEQ ID NO 55
<211> LENGTH: 22
<212> TYPE: RNA
<213> ORGANISM: Homo sapiens

<400> SEQUENCE: 55
uuuggucccc uucaaccagc ug 22

<210> SEQ ID NO 56
<211> LENGTH: 21
<212> TYPE: RNA
<213> ORGANISM: Homo sapiens

<400> SEQUENCE: 56
cauaaaguag aaagcacuac u 21

<210> SEQ ID NO 57
<211> LENGTH: 22
<212> TYPE: RNA
<213> ORGANISM: Homo sapiens

<400> SEQUENCE: 57
gugaaauguu uaggaccacu ag 22

<210> SEQ ID NO 58
<211> LENGTH: 22
<212> TYPE: RNA
<213> ORGANISM: Homo sapiens

<400> SEQUENCE: 58
uggaauguaa agaaguaugu au 22

<210> SEQ ID NO 59
<211> LENGTH: 23
<212> TYPE: RNA
<213> ORGANISM: Homo sapiens

<400> SEQUENCE: 59
aacauucaac gcugucggug agu 23

<210> SEQ ID NO 60
<211> LENGTH: 23
<212> TYPE: RNA
<213> ORGANISM: Homo sapiens

<400> SEQUENCE: 60
agcucggucu gaggccccuc agu 23

<210> SEQ ID NO 61
<211> LENGTH: 21
<212> TYPE: RNA
<213> ORGANISM: Homo sapiens

<400> SEQUENCE: 61
uacaguacug ugauaacuga a 21

<210> SEQ ID NO 62
<211> LENGTH: 22
<212> TYPE: RNA
<213> ORGANISM: Homo sapiens

<400> SEQUENCE: 62
ugagaacuga auuccauggg uu 22

<210> SEQ ID NO 63
<211> LENGTH: 22
<212> TYPE: RNA
<213> ORGANISM: Homo sapiens

<400> SEQUENCE: 63
uagcagcacg uaaauauugg cg 22

<210> SEQ ID NO 64
<211> LENGTH: 22
<212> TYPE: RNA
<213> ORGANISM: Homo sapiens

<400> SEQUENCE: 64
uccuucauuc caccggaguc ug 22

<210> SEQ ID NO 65
<211> LENGTH: 21
<212> TYPE: RNA
<213> ORGANISM: Homo sapiens

<400> SEQUENCE: 65
agcuacaucu ggcuacuggg u 21

<210> SEQ ID NO 66
<211> LENGTH: 22
<212> TYPE: RNA
<213> ORGANISM: Homo sapiens

<400> SEQUENCE: 66
ccaccucccc ugcaaacguc ca 22

<210> SEQ ID NO 67
<211> LENGTH: 22
<212> TYPE: RNA
<213> ORGANISM: Homo sapiens

<400> SEQUENCE: 67
cagugcaaug uuaaaagggc au 22

<210> SEQ ID NO 68
<211> LENGTH: 22
<212> TYPE: RNA
<213> ORGANISM: Homo sapiens

<400> SEQUENCE: 68
ucagugcauc acagaacuuu gu 22

<210> SEQ ID NO 69
<211> LENGTH: 22
<212> TYPE: RNA
<213> ORGANISM: Homo sapiens

<400> SEQUENCE: 69
uauugcacuu gucccggccu gu 22

<210> SEQ ID NO 70
<211> LENGTH: 23
<212> TYPE: RNA
<213> ORGANISM: Mus musculus

<400> SEQUENCE: 70
uguaguguuu ccuacuuuau gga 23

<210> SEQ ID NO 71
<211> LENGTH: 22
<212> TYPE: RNA
<213> ORGANISM: Mus musculus

<400> SEQUENCE: 71
cgaaucauua uuugcugcuc ua 22

<210> SEQ ID NO 72
<211> LENGTH: 22
<212> TYPE: RNA
<213> ORGANISM: Mus musculus

<400> SEQUENCE: 72
uagcagcaca uaaugguuug ug 22

<210> SEQ ID NO 73
<211> LENGTH: 21
<212> TYPE: RNA
<213> ORGANISM: Mus musculus

<400> SEQUENCE: 73
ugagaugaag cacuguagcu c 21

<210> SEQ ID NO 74
<211> LENGTH: 23
<212> TYPE: RNA
<213> ORGANISM: Mus musculus

<400> SEQUENCE: 74
ucaagagcaa uaacgaaaaa ugu 23

<210> SEQ ID NO 75
<211> LENGTH: 21
<212> TYPE: RNA
<213> ORGANISM: Mus musculus

<400> SEQUENCE: 75
uaaagugcug acagugcaga u 21

<210> SEQ ID NO 76
<211> LENGTH: 23
<212> TYPE: RNA
<213> ORGANISM: Homo sapiens

<400> SEQUENCE: 76
aaaagugcuu acagugcagg uag 23

<210> SEQ ID NO 77
<211> LENGTH: 23
<212> TYPE: RNA
<213> ORGANISM: Homo sapiens

<400> SEQUENCE: 77
uaaagugcuu auagugcagg uag 23

<210> SEQ ID NO 78
<211> LENGTH: 22
<212> TYPE: RNA
<213> ORGANISM: Homo sapiens -continued

```
<400> SEQUENCE: 78

uguaaacauc cuugacugga ag                                            22


<210> SEQ ID NO 79
<211> LENGTH: 23
<212> TYPE: RNA
<213> ORGANISM: Homo sapiens

<400> SEQUENCE: 79

ucucacacag aaaucgcacc cgu                                           23
```